US009771385B2

(12) United States Patent
Ishai et al.

(10) Patent No.: US 9,771,385 B2
(45) Date of Patent: Sep. 26, 2017

(54) OXIDIZED LIPIDS

(71) Applicant: Vascular Biogenics Ltd., Or Yehuda (IL)

(72) Inventors: Eti Kovalevski Ishai, Netania (IL); Itzhak Mendel, Rehovot (IL); Yaniv Salem, Kyriat Ono (IL); Niva Yacov, Tel Aviv (IL); Eyal Breitbart, Hashmonaim (IL)

(73) Assignee: Vascular Biogenics Ltd., Or Yehuda (IL)

( * ) Notice: Subject to any disclaimer, the term of this patent is extended or adjusted under 35 U.S.C. 154(b) by 0 days.

(21) Appl. No.: 14/952,827

(22) Filed: Nov. 25, 2015

(65) Prior Publication Data

US 2016/0304544 A1 Oct. 20, 2016

Related U.S. Application Data

(60) Provisional application No. 62/085,153, filed on Nov. 26, 2014.

(51) Int. Cl.
 *C07F 9/58* (2006.01)

(52) U.S. Cl.
 CPC .................................. *C07F 9/581* (2013.01)

(58) Field of Classification Search
 CPC ....................................................... C07F 9/581
 USPC .......................................................... 546/22
 See application file for complete search history.

(56) References Cited

U.S. PATENT DOCUMENTS

| | | | |
|---|---|---|---|
| 4,329,302 A | 5/1982 | Hanahan et al. |
| 4,450,877 A | 5/1984 | Walker et al. |
| 4,543,258 A | 9/1985 | Urata et al. |
| 4,614,796 A | 9/1986 | Kawamata et al. |
| 4,622,180 A | 11/1986 | Paltauf et al. |
| 4,778,912 A | 10/1988 | Inoue et al. |
| 4,827,011 A | 5/1989 | Wissner et al. |
| 4,978,670 A | 12/1990 | Rector et al. |
| 5,053,402 A | 10/1991 | Masaki et al. |
| 5,061,626 A | 10/1991 | Baldo et al. |
| 5,091,527 A | 2/1992 | Junius et al. |
| 5,561,052 A | 10/1996 | Koike |
| 5,614,548 A | 3/1997 | Piantadosi et al. |
| 5,660,855 A | 8/1997 | Malé-Brune |
| 5,962,437 A | 10/1999 | Kucera et al. |
| 5,985,292 A | 11/1999 | Fourneron et al. |
| 6,017,513 A | 1/2000 | Betbeder et al. |
| 6,261,597 B1 | 7/2001 | Kurtz |
| 6,348,583 B1 | 2/2002 | Segev |
| 6,414,168 B1 | 7/2002 | Crivello et al. |
| 6,838,452 B2 | 1/2005 | Harats et al. |
| 7,186,704 B2 | 3/2007 | Harats et al. |
| 7,504,388 B2 | 3/2009 | Harats et al. |
| 7,517,858 B1 | 4/2009 | Hostetier et al. |
| 7,625,882 B2 | 12/2009 | Harats et al. |
| 7,807,847 B2 | 10/2010 | Halperin et al. |
| 7,893,291 B2 | 2/2011 | Harats et al. |
| 7,902,176 B2 | 3/2011 | Harats et al. |
| 7,973,023 B2 | 7/2011 | Harats et al. |
| 8,084,209 B2 | 12/2011 | Medina et al. |
| 8,124,800 B2 | 2/2012 | Halperin et al. |
| 8,158,611 B2 | 4/2012 | Harats et al. |
| 8,501,715 B2 | 8/2013 | Harats et al. |
| 8,563,534 B2 | 10/2013 | Harats et al. |
| 8,569,529 B2 | 10/2013 | Halperin et al. |
| 8,759,557 B2 | 6/2014 | Halperin et al. |
| 8,802,875 B2 | 8/2014 | Halperin et al. |
| 8,999,960 B2 | 4/2015 | Breitbart et al. |
| 9,006,217 B2 | 4/2015 | Halperin et al. |
| 9,206,206 B2 | 12/2015 | Breitbart et al. |
| 9,254,297 B2 | 2/2016 | Sher et al. |
| 2003/0225035 A1 | 12/2003 | Harats et al. |
| 2006/0140936 A1 | 6/2006 | Goldenberg et al. |
| 2006/0194765 A1 | 8/2006 | Garcia et al. |
| 2007/0020691 A1 | 1/2007 | Kanter et al. |
| 2007/0099868 A1 | 5/2007 | Harats et al. |
| 2007/0264206 A1 | 11/2007 | Boga et al. |
| 2008/0261865 A1 | 10/2008 | Harats et al. |
| 2009/0074720 A1 | 3/2009 | Sabbadini |
| 2009/0149541 A1 | 6/2009 | Stark et al. |
| 2009/0197242 A1 | 8/2009 | Kaddurah-Daouk et al. |
| 2010/0048515 A1 | 2/2010 | Harats et al. |
| 2011/0189212 A1 | 8/2011 | Harats et al. |
| 2011/0195937 A1 | 8/2011 | Breitbart et al. |
| 2011/0207703 A1 | 8/2011 | Kovalevski-Ishai et al. |
| 2012/0130108 A1 | 5/2012 | Halperin et al. |

(Continued)

FOREIGN PATENT DOCUMENTS

| | | |
|---|---|---|
| AU | 2004243695 A1 | 12/2004 |
| CA | 1102354 | 6/1981 |

(Continued)

OTHER PUBLICATIONS

Berchtold, R., "Synthesis of Carboxyphospholipids," *Chem. Phys. Lipids* 18(1):55-60, Elsevier, Netherlands (1981).
Bochkov, V.N., "Inflammatory Profile of Oxidized Phospholipids," *Journal of Thrombosis and Haemastosis*, 97:348-354, Schattauer GmbH, Germany (2007).
Boullier, A., et al., "The Binding of Oxidized Low Density Lipoprotein to Mouse CD36 Is Mediated in Part by Oxidized Phospholipids That Are Associated With Both the Lipid and Protein Moieties of the Lipoprotein," *Journal of Biological Chemistry*, 275(13):9163-9169, The American Society for Biochemistry and Molecular Biology, Inc., United States (2000).
Chen, X., et al., "Polyunsaturated Phospholipids Promote the Oxidation and Fragmentation of γ-Hydroxyalkenals: Formation and Reactions of Oxidatively Truncated Ether Phospholipids," *Journal of Lipid Research*, 49:832-846, American Society for Biochemistry and Molecular Biology, United States (2008).

(Continued)

*Primary Examiner* — Susanna Moore
(74) *Attorney, Agent, or Firm* — Sterne, Kessler, Goldstein & Fox P.L.L.C.

(57) ABSTRACT

The present invention is directed to oxidized lipids and pharmaceutical compositions comprising the same. The present invention is also directed to methods of making an oxidized lipid of the invention and to methods of treating or preventing fibrosis or inflammatory diseases or disorders comprising an oxidized lipid of the invention.

37 Claims, 37 Drawing Sheets

(56) References Cited

U.S. PATENT DOCUMENTS

| | | | |
|---|---|---|---|
| 2012/0329757 A1 | 12/2012 | Harats et al. | |
| 2012/0329758 A1 | 12/2012 | Cohen et al. | |
| 2013/0079540 A1 | 3/2013 | Halperin et al. | |
| 2013/0172294 A1 | 7/2013 | Cohen et al. | |
| 2013/0203707 A1 | 8/2013 | Kovalevski-Ishai et al. | |
| 2013/0209555 A1 | 8/2013 | Sher et al. | |
| 2013/0225525 A1 | 8/2013 | Cohen et al. | |
| 2013/0237720 A1 | 9/2013 | Halperin et al. | |
| 2015/0216882 A1 | 8/2015 | Halperin et al. | |
| 2015/0320773 A1 | 11/2015 | Mendel et al. | |
| 2016/0008381 A1 | 1/2016 | Cohen et al. | |
| 2016/0038518 A1 | 2/2016 | Sher et al. | |
| 2016/0220590 A1 | 8/2016 | Sher et al. | |

FOREIGN PATENT DOCUMENTS

| | | |
|---|---|---|
| CH | 642 665 A5 | 4/1984 |
| EP | 0 121 088 A1 | 10/1984 |
| EP | 0 142 333 A2 | 5/1985 |
| EP | 0 184 905 A1 | 6/1986 |
| EP | 0 225 129 A1 | 6/1987 |
| EP | 0 331 167 A2 | 9/1989 |
| ES | 2 019 552 A6 | 6/1991 |
| GB | 2 130 206 A | 5/1984 |
| JP | 50004040 A | 1/1975 |
| JP | 54-41807 | 4/1979 |
| JP | 58154512 | 9/1983 |
| JP | 59-93022 | 5/1984 |
| JP | 59-175445 | 10/1984 |
| JP | 60-104066 A | 6/1985 |
| JP | 62-228088 | 11/1986 |
| JP | 62-000094 A | 1/1987 |
| JP | 62-030714 A | 2/1987 |
| JP | 63-054386 A | 3/1988 |
| JP | 63-135395 A | 6/1988 |
| JP | 01-258691 A | 10/1989 |
| JP | 02-006493 | 1/1990 |
| JP | 02-048585 A | 2/1990 |
| JP | 03-258740 | 11/1991 |
| JP | 04-021691 | 1/1992 |
| JP | 05-339387 | 12/1993 |
| JP | 07-258261 A | 10/1995 |
| JP | 08-059545 | 3/1996 |
| JP | 08-208548 | 8/1996 |
| JP | 11-116563 A | 4/1999 |
| JP | 2003-515550 A | 5/2003 |
| JP | 2004-537498 A | 12/2004 |
| JP | 2005-505499 | 2/2005 |
| JP | 2005-507952 A | 3/2005 |
| JP | 2008-037763 A | 2/2008 |
| SU | 1400511 A3 | 5/1988 |
| WO | WO 87/05904 A1 | 10/1987 |
| WO | WO 95/23592 | 9/1995 |
| WO | WO 01/39744 A2 | 6/2001 |
| WO | WO 01/75168 A1 | 10/2001 |
| WO | WO 02/41827 A2 | 5/2002 |
| WO | WO 02/087465 A2 | 11/2002 |
| WO | WO 03/040073 A1 | 5/2003 |
| WO | WO 2004/106486 A2 | 12/2004 |
| WO | WO 2006/006161 A2 | 1/2006 |
| WO | WO 2008/084472 A2 | 7/2008 |
| WO | WO 2010/041242 A2 | 4/2010 |
| WO | WO 2010/052718 A1 | 5/2010 |
| WO | WO 2011/083464 A1 | 7/2011 |
| WO | WO 2011/083465 A1 | 7/2011 |
| WO | WO 2011/083466 A1 | 7/2011 |
| WO | WO 2011/083467 A1 | 7/2011 |
| WO | WO 2011/083469 A1 | 7/2011 |
| WO | WO 2013/033642 A1 | 3/2013 |
| WO | WO 2013/088245 | 6/2013 |
| WO | WO 2013/121300 | 8/2013 |
| WO | WO 2016/084023 | 6/2016 |
| WO | WO 2016/084024 | 6/2016 |

OTHER PUBLICATIONS

Cooney, S., et al., "Combining site specificities of rabbit antibodies to platelet-activating factor (PAF)," *Mol Immunol.* 27(5):405-12, Pergamon Press, Great Britain (1990).

Davies, S., et al. "Oxidized Alkyl Phospholipids Are Specific, High Affinity Peroxisome Proliferator—Activated Receptor γ Ligands and Agonists," *Journal of Biological Chemistry* 276(19):16015-16023, The American Society for Biochemistry and Molecular Biology, Inc., United States (2001).

Deigner, H-P. and Dresel, H.A., "Effect of platelet activating factor on the kinetics of LDL oxidation in vitro," *FEBS Lett.* 317(3):202-6, Elsevier Science, Netherlands (1993).

George, J., et al. "Hyperimmunization of Apo-E-Deficient Mice with Homologous Malondialdehyde Low-Density Lipoprotein Suppresses early Atherogenesis," *Atherosclerosis* 138:147-152, Elsevier Science, Ireland (1998).

Hoff, H.F., et al., "Phospholipid Hydroxyalkenals: Biological and Chemical Properties of Specific Oxidized Lipids Present in Atherosclerotic Lesions," *Arterioscler. Thromb. Vasc. Biol.* 23:275-282, The American Heart Association, United States (2003).

Itabe, H., et al. "Oxidized Phosphatidylcholines That Modify Proteins," *Journal of Biological Chemistry* 271(52):33208-33217, The American Society for Biochemistry and Molecular Biology, United States (1996).

Itabe, H., et al., "Preparation of redioactive aldehyde-containing phosphatidylcholine," *Anal. Biochem.* 285(1):151-5, Academic Press, United States (2000).

Kamido, H., et al., "Lipid ester-bound aldehydes among copper-catalyzed peroxidation products of human plasma lipoproteins," *J. Lipid Res.* 36(9):1876-1886, American Society for Biochemistry and Molecular Biology, United States (1995).

Karasawa, K., et al., "Antibodies to synthetic platelet-activating factor (1-0-alkyl-2-0-acetyl-sn-glycero-3—phosphocholine) analogues with substituents at the sn-2 position," *J. Biochem.* 110(5):683-7, Oxford University Press, England (1991).

Kern, H., "Stimulation of monocytes and platelets by short-chain phosphatidylcholines with and without terminal carboxyl group," *Biochem. Biophys. Acta* 1394(1):33-42, Elsevier, Netherlands (1998).

Leitinger, N., et al. "Structurally Similar Oxidized Phospholipids Differentially Regulate Endothelial Binding of Monocytes and Neutrophils," *Proc. Natl. Acad. Sci.* 96(21):12010-12015, National Academy of Sciences, United States (1999).

MacPherson, J.L., et al., "Production and characterization of antibodies to platelet-activating factor," *J. Lipid. Mediat.* 5(1):49-59, Elsevier Science Publishers, Netherlands (1992).

Mendel, I., et al., "A Lecinoxoid, an oxidized phospholipid small molecule, constrains CNS autoimmune disease," *J. Neuroimmunol.* 226:126-35, Elsevier B.V., Netherlands (2010).

Nitta, T., et al., "Phospholipase $A_2$ Activity of $Fc_{\gamma 2b}$Receptors of Thioglycollate-Elicited Murine Peritoneal Macrophages," *J. Leuk. Biol.* 36(4):493-504, Wiley-Liss, United States (1984).

"The Nomenclature of Lipids," *Journal of Lipid Research* 8:523-528, American Society for Biochemistry and Molecular Biology, United States (1967).

Ota, Y., "Complexes of apoA-1 with phosphatidylcholine suppress dysregulation of arterial tone by oxidized LDL," *Am. J. Physiol.* 273(3), Part 2:H1215-22, The American Physiological Society, United States (1997).

Podrez, E.A., et al., "A Novel Family of Atherogenic Oxidized Phospholipids Promotes Macrophage Foam Cell Formation Via the Scavenger Receptor CD36 and Is Enriched in Atherosclerotic Lesions," *J. Biol. Chem.* 277(41): 38517-38523, The American Society for Biochemistry and Molecular Biology, Inc., United States (2002).

Podrez, E.A., et al., "Identification of a Novel Family of Oxidized Phospholipids That Serve as Ligands for the Macrophage Scavenger Receptor CD36," *J. Biol. Chem.* 277(41): 38503-38516, The American Society for Biochemistry and Molecular Biology, Inc., United States (2002).

Pontsler, A.V., et al., "Cyclooxygenase-2 is induced in monocytes by peroxisome proliferator activated receptor gamma and oxidized alkyl phospholipids from oxidized low density lipoprotein," *J. Biol.*

(56) References Cited

OTHER PUBLICATIONS

Chem. 277(15):13029-36, The American Society for Biochemistry and Molecular Biology, United States (2002).
Shaw, P.X., et al., "Natural antibodies with the T15 idiotype may act in atherosclerosis, apoptotic clearance, and protective immunity," *J. Clin. Invest.* 105(12):1731-1740, American Society for Clinical Investigation, United States (2000).
Smal, M.A., et al., "Production of antibodies to platelet activating factor," *Mol. Immunol.* 26(8):711-19, Pergamon Press, England (1989).
"Study to Assess VB-201 in Patients with Psoriasis," accessed at: http://clinicaltrialsfeeds.org/clinical-trials/show/NCT01001468, on Oct. 2, 2012.
Subbanagounder, G., et al. "Evidence That Phospholipid Oxidation Products and/or Platelet-Activating Factor Play an Important Role in Early Atherogenesis: In Vitro and In Vivo Inhibition by WEB 2086," *Circulation Research* 85:311-318, American Heart Association, United States (1999).
Subbanagounder, G., et al. "Determinants of Bioactivity of Oxidized Phospholipids: Specific Oxidized Fatty Acyl Groups at the SN-2 Position," *Arteriosclerosis Thromb. Vasc. Biol.* 2248-2254, American Heart Association, United States (2000).
Sun, M., et al., "Novel bioactive phospholipids: practical total syntheses of products from the oxidation of arachidonic and linoleic esters of 2-lysophosphatidylcholine," *J. Org. Chem.* 67(11):3575-84, American Chemical Society, United States (2002).
Tokumura, A., et al. "Cardiovascular Effects of Lysophosphatidic Acid and Its Structural Analogs in Rats," *The Journal of Pharmacology and Experimental Therapeutics* 219:219-224, The American Society of Pharmacology and Experimental Therapeutics, United States (1981).
Wang, C.J. and Tai, H.H., "A facile synthesis of an aldehydic analog of platelet activating factor and its use in the production of specific antibodies," *Chem. Phys. Lipids* 55(3):265-73, Elsevier Science Ireland Ltd., Ireland (1990).
Watson et al. "Structural Identification by Mass Spectrometry of Oxidized Phospholipids in Minimally Oxidized Low Density Lipoprotein That Induce Monocyte/Endothelial Interactions and Evidence for their Presence in Vivo," *J. Biol. Chem.* 272(21):13597-13607, The American Society for Biochemistry and Molecular Biology, Inc., United States (1997).
English language abstract of CH642665 A5, espacenet database, Worldwide, published Apr. 30, 1984.
English language abstract of JP 60-104066, espacenet database, Worldwide, published Jun. 8, 1985.
English language abstract of JP 62-000094 A, espacenet database, Worldwide, published Jan. 6, 1987.
English language abstract of JP 62-030714 A, espacenet database, Worldwide, published Feb. 9, 1987.
English language abstract of JP 63-054386 A, espacenet database, Worldwide, published Mar. 8, 1988.
English language abstract of JP 63-135395 A, espacenet database, Worldwide, published Jun. 7, 1988.
English language abstract of ES 2 019 552 A6, espacenet database, Worldwide, published Jun. 16, 1991.
English language abstract of JP 11-116563 A, espacenet database, Worldwide, published Apr. 27, 1999.
International Search Report and Written Opinion dated Aug. 24, 2006 from the International Searching Authority Re.: Application No. PCT/IL05/00735.
International Search Report and Written Opinion dated Mar. 13, 2009 from the International Searching Authority Re.: Application No. PCT/IL08/000013.
International Search Report and Written Opinion dated Apr. 18, 2011 from the International Searching Authority Re.: Application No. PCT/IL11/00008.
International Search Report and Written Opinion dated Apr. 18, 2011 from the International Searching Authority Re.: Application No. PCT/IL11/00010.
International Search Report and Written Opinion dated Apr. 18, 2011 from the International Searching Authority Re.: Application No. PCT/IL11/00012.
International Search Report and Written Opinion dated Jul. 11, 2002 and Aug. 12, 2003, respectively, from the International Searching Authority Re.: Application No. PCT/IL01/01080.
International Search Report and Written Opinion dated Nov. 23, 2004 from the International Searching Authority Re.: Application No. PCT/IL2004/000453.
International Search Report and Written Opinion dated Mar. 24, 2010 from the International Searching Authority Re.: Application No. PCT/IL2009/001049.
International Search Report and Written Opinion dated Apr. 6, 2010 from the International Searching Authority Re.: Application No. PCT/IL09/00949.
International Preliminary Report on Patentability dated Jan. 9, 2007 from the International Bureau of WIPO Re.: Application No. PCT/IL05/00735.
International Preliminary Report on Patentability dated Oct. 20, 2009 from the International Bureau of WIPO Re.: Application No. PCT/IL08/000013.
International Preliminary Report on Patentability dated Apr. 12, 2011 from the International Bureau of WIPO Re.: Application No. PCT/IL2009/000949.
International Preliminary Report on Patentability dated Apr. 9, 2005 from the International Bureau of WIPO Re.: Application No. PCT/IL2004/000453.
International Preliminary Report on Patentability dated May 10, 2011 from the International Bureau of WIPO Re.: Application No. PCT/IL2009/001049.
International Preliminary Report on Patentability dated Jan. 6, 2005 from the International Preliminary Examining Authority Re.: Application No. PCT/IL01/01080.
International Preliminary Report on Patentability dated Jul. 10, 2012 from the International Bureau of WIPO Re.: Application No. PCT/IL11/00012.
International Preliminary Report on Patentability dated Jul. 10, 2012 from the International Bureau of WIPO Re.: Application No. PCT/IL11/00010.
International Preliminary Report on Patentability dated Jul. 10, 2012 from the International Bureau of WIPO Re.: Application No. PCT/IL11/00008.
European Search Report and European Search Opinion dated Feb. 3, 2012 from the European Patent Office Re.: Application No. 11189562.9.
Supplementary Partial European Search Report and European Search Opinion dated Nov. 30, 2009 from the European Patent Office Re.: Application No. 05 75 8938.4.
Supplementary Partial European Search Report dated Mar. 25, 2011 from the European Patent Office Re.: Application No. 08 70 0247.3.
Supplementary European Search Report dated Aug. 3, 2009 from the European Patent Office Re.: Application No. 01997274.4.
Supplementary Partial European Search Report dated Aug. 5, 2009 from the European Patent Office Re.: Application No. 04735088.9.
Supplementary European Search Report and European Search Opinion dated Mar. 9, 2012 from the European Patent Office Re.: Application No. 09824498.1.
Supplementary European Search Report and European Search Opinion dated Oct. 16, 2012 from the European Patent Office Re.: Application No. 12 178 298.1.
Notice of Allowance dated Jun. 10, 2010 from the US Patent and Trademark Office Re.: U.S. Appl. No. 11/650,973.
Office Action dated Dec. 1, 2009 from the US Patent and Trademark Office Re.: U.S. Appl. No. 11/650,973.
Office Action dated May 14, 2009 from the US Patent and Trademark Office Re.: U.S. Appl. No. 11/650,973.
Office Action dated Aug. 19, 2008 from the US Patent and Trademark Office Re.: U.S. Appl. No. 11/650,973.
Notice of Allowance dated Oct. 26, 2011 from the US Patent and Trademark Office Re.: U.S. Appl. No. 12/861,921.
Office Action dated Mar. 17, 2011 from the US Patent and Trademark Office Re.: U.S. Appl. No. 12/861,921.

(56) References Cited

OTHER PUBLICATIONS

Notice of Allowance dated Jan. 24, 2011 from the US Patent and Trademark Office Re.: U.S. Appl. No. 12/588,371.
Office Action dated Aug. 23, 2010 from the US Patent and Trademark Office Re.: U.S. Appl. No. 12/588,371.
Office Action dated May 28, 2010 from the US Patent and Trademark Office Re.: U.S. Appl. No. 12/588,371.
Notice of Allowance dated Nov. 3, 2010 from the US Patent and Trademark Office Re.: U.S. Appl. No. 10/567,543.
Office Action dated Jun. 15, 2010 from the US Patent and Trademark Office Re.: U.S. Appl. No. 10/567,543.
Office Action dated Mar. 9, 2010 from the US Patent and Trademark Office Re.: U.S. Appl. No. 10/567,543.
Notice of Allowance dated May 25, 2006 from the US Patent and Trademark Office Re.: U.S. Appl. No. 10/718,596.
Final Office Action dated Mar. 2, 2006 from the US Patent and Trademark Office Re.: U.S. Appl. No. 10/718,596.
Office Action dated Jul. 15, 2005 from the US Patent and Trademark Office Re.: U.S. Appl. No. 10/718,596.
Corrected Notice of Allowance dated Jul. 23, 2009 from the US Patent and Trademark Office Re.: U.S. Appl. No. 11/528,657.
Notice of Allowance dated Jun. 30, 2009 from the US Patent and Trademark Office Re.: U.S. Appl. No. 11/528,657.
Office Action dated Nov. 25, 2008 from the US Patent and Trademark Office Re.: U.S. Appl. No. 11/528,657.
Notice of Allowance dated Nov. 3, 2008 from the US Patent and Trademark Office Re.: U.S. Appl. No. 11/183,884.
Office Action dated Apr. 16, 2008 from the US Patent and Trademark Office Re.: U.S. Appl. No. 11/183,884.
Office Action dated Dec. 7, 2007 from the US Patent and Trademark Office Re.: U.S. Appl. No. 11/183,884.
Notice of Allowance dated Oct. 18, 2010 from the US Patent and Trademark Office Re.: U.S. Appl. No. 12/371,930.
Office Action dated Feb. 24, 2010 from the US Patent and Trademark office Re.: U.S. Appl. No. 12/371,930.
Office Action dated May 27, 2010 from the US Patent and Trademark Office Re.: U.S. Appl. No. 12/371,930.
Notice of Allowance dated Dec. 15, 2011 from the US Patent and Trademark Office Re.: U.S. Appl. No. 12/985,365.
Notice of Allowance dated Dec. 12, 2011 from the US Patent and Trademark Office Re.: U.S. Appl. No. 12/985,365.
Office Action dated Aug. 5, 2011 from the US Patent and Trademark Office Re.: U.S. Appl. No. 12/985,365.
Notice of Allowance dated Jul. 2, 2004 from the US Patent and Trademark Office Re.: U.S. Appl. No. 10/445,347.
Office Action dated Jan. 7, 2004 from the US Patent and Trademark Office Re.: U.S. Appl. No. 10/445,347.
Office Action dated Nov. 14, 2003 from the US Patent and Trademark Office Re.: U.S. Appl. No. 10/445,347.
Office Action dated Jun. 12, 2012 from the US Patent and Trademark Office Re.: U.S. Appl. No. 13/358,573.
Notice of Allowance dated Oct. 31, 2012 from the US Patent and Trademark Office Re.: U.S. Appl. No. 13/085,542.
Office Action dated Mar. 16, 2012 from the US Patent and Trademark Office Re.: U.S. Appl. No. 13/085,542.
International Search Report dated Sep. 1, 2011 from the International Searching Authority Re: Application No. PCT/IL11/00007.
International Search Report dated May 20, 2011 from the International Searching Authority Re: Application No. PCT/IL11/00009.
International Preliminary Report on Patentability dated Jul. 10, 2012 from the International Bureau of WIPO Re: Application No. PCT/IL2011/000007.
International Preliminary Report on Patentability dated Jul. 10, 2012 from the International Bureau of WIPO Re: Application No. PCT/IL2011/000009.
International Search Report dated Nov. 13, 2012 from the European Patent Office Re: Application No. PCT/US2012/053533.
Paimela, L., et al., "Clinical significance of antibodies against oxidised low density lipoprotein in early RA," *Ann. Rheum. Dis.* 55(8):558-559, H.K. Lewis, England (1996).

Onorato, J.M., et al., "Immunohistochemical and ELISA assays for Biomarkers of Oxidative Stress in Aging and Disease," *Ann. N. Y. Acad. Sci.* 854:277-290, Blackwell, United States (1998).
Sawai, T., et al., "The effect of phospholipids and fatty acids on tight-junction permeability and bacterial translocation," *Pediatr. Surg. Int.* 17(4):269-274, Springer-Verlag, Germany (2001).
Noguchi, S., et al., "Effect of Extracellular Phosphatidylinositol on C-*MYC* Gene-Expressed Human Renal Cancer Cell Line," *Biochem. Biophys. Res. Commun.* 182(2):644-650, Academic Press, United States (1992).
Lombardin, P., et al., "Study of thixotropic bases for the filling of hard capsules," *S.T.P Pharma Sciences* 10(6):429-437, Editions de Santé, France (2000).
Notice of Allowance dated Mar. 8, 2013 From the U.S. Patent and Trademark Office Re: U.S. Appl. No. 13/085,542, filed Apr. 13, 2011.
Office Action dated Mar. 25, 2013 from the U.S. Patent and Trademark Office Re: U.S. Appl. No. 13/672,811, filed Nov. 9, 2012.
Office Action dated Mar. 15, 2013 from the US Patent and Trademark Office Re: U.S. Appl. No. 13/122,766, filed Apr. 6, 2011.
U.S. Appl. No. 13/792,633, filed Mar. 11, 2013, inventors Sher, N., et al. (now published).
U.S. Appl. No. 13/709,198, filed Dec. 10, 2012, inventors Halperin, G. and Kovalevski-Ishai, E. (now patented).
U.S. Appl. No. 13/796,654, filed Mar. 12, 2013, inventors Halperin, G. and Kovalevski-Ishai, E. (now patented).
U.S. Appl. No. 13/833,940, filed Mar. 15, 2013, inventors Halperin, G. and Kovalevski-Ishai, E. (now published).
U.S. Appl. No. 13/828,883, filed Mar. 14, 2013 inventors Kovalevski-Ishai, E., et al. (now published).
U.S. Appl. No. 13/828,643, filed Mar. 14, 2013 inventors Cohen Y., et al. (now published).
Bochkov, V.N., et. al., "Protective role of phospholipid oxidation products in endotoxin induced tissue damage," *Nature*, 419:77-81, Nature Publishing Group, England (Sep. 2002).
Office Action dated Jan. 16, 2013 from the US Patent and Trademark Office Re: U.S. Appl. No. 13/431,262, filed Mar. 27, 2012.
Notice of Allowance dated Jun. 12, 2013 from the US Patent and Trademark Office Re: U.S. Appl. No. 13/431,262, filed Mar. 27, 2012.
English language abstract for JP50004040 A, Derwent World Patents Index, Dialog File No. 351, Accession No. 849902, Accessed on Mar. 25, 2013.
Langan, R.C., et al., "Ulcerative colitis: diagnosis and treatment," *Am. Fam. Physician* 76(9): 1323-30, American Academy of Family Physicians, United States (2007).
Anand, S.S. and Yusuf, S., "C-reactive protein is a bystander of cardiovascular disease," *Eur. Heart. J.* 31(17):2092-2097, Oxford University Press, England (2010).
Office Action dated Apr. 10, 2013 from the US Patent and Trademark Office Re: U.S. Appl. No. 13/520,713, filed Jul. 5, 2012.
"Guidance for Industry: Estimating the Maximum Safe Starting Dose in Initial Clinical Trials for Therapeutics in Adult Health Volunteers," U.S. Department of Health and Human Services, Food and Drug Administration, Center for Drug Evaluation and Research, pp. 1-27 (Jul. 2005).
Office Action dated Aug. 30, 2013 from the US Patent and Trademark Office Re: U.S. Appl. No. 13/828,643, filed Mar. 14, 2013.
Office Action dated Aug. 7, 2013 from the US Patent and Trademark Office Re: U.S. Appl. No. 13/520,713, § 371(c) date: Jul. 5, 2012.
Office Action dated Aug. 22, 2013 from the US Patent and Trademark Office Re: U.S. Appl. No. 13/709,198, filed Dec. 10, 2012.
Office Action dated Aug. 22, 2013 from the US Patent and Trademark Office Re: U.S. Appl. No. 13/796,654, filed Mar. 12, 2013.
Office Action dated Sep. 16, 2013 from the US Patent and Trademark Office Re: U.S. Appl. No. 13/833,940, filed Mar. 15, 2013.
Bhattacharyya, S., et al., "Toll-Like Receptor 4 Signaling Augments Transforming Growth Factor-β Responses: A Novel Mechanism for Maintaining and Amplifying Fibrosis Scleroderma," *The American Journal of Pathology* 182(1):192-205, Elsevier Inc., United States (2013).

(56) References Cited

OTHER PUBLICATIONS

Csak, T., et al., "Deficiency in myeloid differentiation factor-2 and toll-like receptor 4 expression attenuates nonalcoholic steatohepatitis and fibrosis in mice," *Am J Physiol Gastrointest Liver Physiol* 300:G433-G441, American Physiological Society, United States (2011).
Franklin, C., et al., "Design, Synthesis, and Evaluation of Water-Soluble Phospholipid Analogues as Inhibitors of Phospholipase C from *Bacillus cereus*," *Journal of Organic Chemistry* 68(19):7298-7307, American Chemical Society, United States (2003), Caplus AN 2003:643618.
Herre, J., et al., "Allergens as Immunomodulatory Proteins: The Cat Dander Protein Fel d 1 Enhances TLR Activation by Lipid Ligands," *J Immunol* 191:1529-1535, American Association of Immunologists, Inc., United States (2013).
Kwok, S-K., et al., "TLR2 litigation induces the production of IL-23/IL-17 via IL-6, STAT3 and NF-kB pathway in patients with primary Sjogren's syndrome," *Arthritis Research & Therapy* 14(R64):1-13, BioMed Central, England (2012).
Lartigue, A., et al., "Critical Role of TLR2 and TLR4 in Autoantibody Production and Glomerulonephritis in *lpr* Mutation-Induced Mouse Lupus," *J Immunol* 183:6207-6216, American Association of Immunologists, Inc., United States (2009).
Li, J., et al., "Toll-like receptors as therapeutic targets for autoimmune connective tissue diseases," *Pharmacology & Therapeutics* 138:441-451, Pergamon Press, England (2013).
Millien, V.O., et al., "Cleavage of Fibrinogen by Proteinases Elicits Allergic Responses Through Toll-Like Receptor 4," *Science* 341(6147):792-796, American Association for the Advancement of Science, United States (2013).
Miura, K., et al., "TLR2 and palmitic acid cooperatively contribute to the development of nonalcoholic steatohepatitis through inflammasome activation," *Hepatology* 57(2):577-589, Wiley, United States (2013).
Wen, Z., et al., "Autoantibody Induction by DNA-Containing Immune Complexes Requires HMGB1 with the TLR2/MicroRNA-155 Pathaway," *J Immunol* 190:5411-5422, American Association for the Advancement of Science, United States (2013).
Office Action dated Mar. 7, 2014, in U.S. Appl. No. 13/833,940, Halperin, G. and Kovalevski-Ishai, E., filed Mar. 15, 2013.
Office Action dated Jul. 16, 2014, in U.S. Appl. No. 13/833,940, Halperin, G. and Kovalevski-Ishai, E., filed Mar. 15, 2013.
Office Action dated Apr. 23, 2014, in U.S. Appl. No. 13/122,766, Breitbart, E., et al., § 371(c) date: Apr. 6, 2011.
Office Action dated Mar. 11, 2014, in U.S. Appl. No. 13/520,713, Cohen, Y., et al., § 371(c) date: Jul. 5, 2012.
Office Action dated Feb. 25, 2014, in U.S. Appl. No. 13/828,643, Cohen, Y., et al., filed Mar. 14, 2013.
Office Action dated Jun. 16, 2014, in U.S. Appl. No. 13/520,719, Cohen, Y., et al., filed Mar. 7, 2013.
International Preliminary Report on Patentability for International Application No. PCT/IB2012/002930, International Bureau of WIPO, Geneva, Switzerland, dated Jun. 17, 2014.
Vascular Biogenics Ltd., operating as VBL Therapeutics, "Study to Assess VB-201 in Patients with Psoriasis," ClinicalTrials.gov, accessed at https://clinicaltrials.gov/ct2/show/NCT01001468?term=VB-201&rank=1, accessed on Aug. 28, 2014, 4 pages.
Vascular Biogenics Ltd., operating as VBL Therapeutics, "A Study to Evaluate the Efficacy and Safety of VB-201 in Patients with Psoriasis," ClinicalTrials.gov, accessed at https://clinicaltrials.gov/ct2/show/NCT01837420?term=VB-201&rank=2, accessed on Aug. 28, 2014, 4 pages.
Vascular Biogenics Ltd., operating as VBL Therapeutics, "Study to Assess the Safety and Efficacy of Multiple Doses of VB-201 on Biomarkers," ClinicalTrials.gov, accessed at https://clinicaltrials.gov/ct2/show/NCT01159730?term=VB-201&rank=3, accessed on Aug. 28, 2014, 2 pages.
Vascular Biogenics Ltd., operating as VBL Therapeutics, "A Study to Evaluate the Efficacy and Safety of VB-201 in Patients with Ulcerative Colitis," ClinicalTrials.gov, accessed at https://clinicaltrials.gov/ct2/show/NCT01839214?term=VB-201&rank=4, accessed on Aug. 28, 2014, 4 pages.
International Search Report and Written Opinion of the International Search Authority, or the Declaration for Int'l Appl. No. PCT/IB12/02930, dated May 21, 2013, U.S. International Searching Authority, Alexandria, Virginia.
International Preliminary Report on Patentability for Int'l Appl. No. PCT/IB12/02930, dated Jun. 26, 2014, International Bureau of WIPO, Geneva, Switzerland.
Final Office Action dated Aug. 26, 2014, in U.S. Appl. No. 13/520,713, Cohen, Y., et al., § 371(c) date: Jul. 5, 2012.
Final Office Action dated Aug. 13, 2014, in U.S. Appl. No. 13/828,643, Cohen, Y., et al., filed Mar. 14, 2013.
Feige, E., et al., "Modified phospholipids as anti-inflammatory compounds," *Curr. Opin. Lipidol.* 21:525-529, Wolters Kluwer Health/Lippincott Williams & Wilkins (2010).
Silva, M.M., et al., "Systemic Inflammatory Reaction After Silicone Breast Implant," *Aesth. Plast. Surg.* 35:789-794, Springer (2011).
Mendel, I., et al., "VB-201, an oxidized phospholipid small molecule, inhibits CD14—and Toll-like receptor-2-dependent innate cell activation and constrains atherosclerosis," *Clin. Exp. Immunol.* 175:126-137, British Society for Immunology (2013).
Office Action dated Mar. 1, 2016, in U.S. Appl. No. 14/364,705, Mendel, I., et al., filed Jun. 12, 2014.
Rivera, C.A., et al., "Toll-like receptor-4-signaling and Kupffer cells play pivotal roles in the pathogenesis of non-alcoholic steatohepatitis," *J. Hepatol.* 47:571-579, Elsevier (2007).
Pidkovka, N., et al., "POVPC induces the smooth muscle cells inflammatory phenotype," *FASEB J.* 21:599.1, FASEB (2007).
Reagan-Shaw, S., et al., "Dose translation from animal to human studies revisited," *FASEB J.* 22:659-661, FASEB (2007).
Final Office Action dated Mar. 30, 2015, in U.S. Appl. No. 13/520,719, Cohen, Y., et al., filed Mar. 7, 2013.
Final Office Action dated Jan. 15, 2016, in U.S. Appl. No. 13/520,719, Cohen, Y., et al., filed Mar. 7, 2013.
English language abstract of JP58154512, published Sep. 14, 1983.
Ali, M.H., et al., "The role of lipid geometry in designing liposomes for the solubilisation of poorly water soluble drugs," *Int. J. Pharmaceut.* 453.1:225-232 (2013).
International Search Report and Written Opinion for International Application No. PCT/IB2015/059134, U.S. Patent and Trademark Office, United States, dated Mar. 11, 2016, 9 pages.

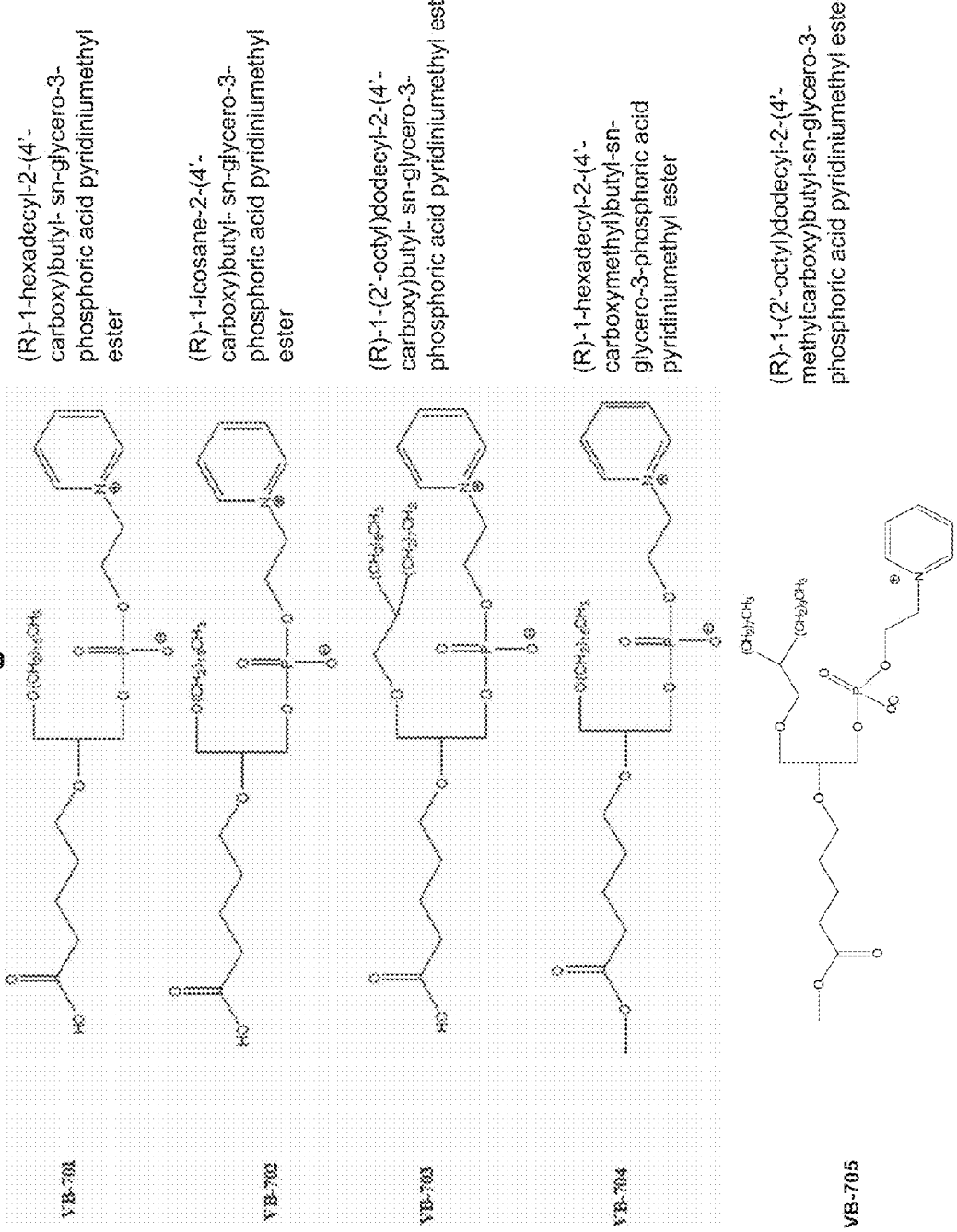

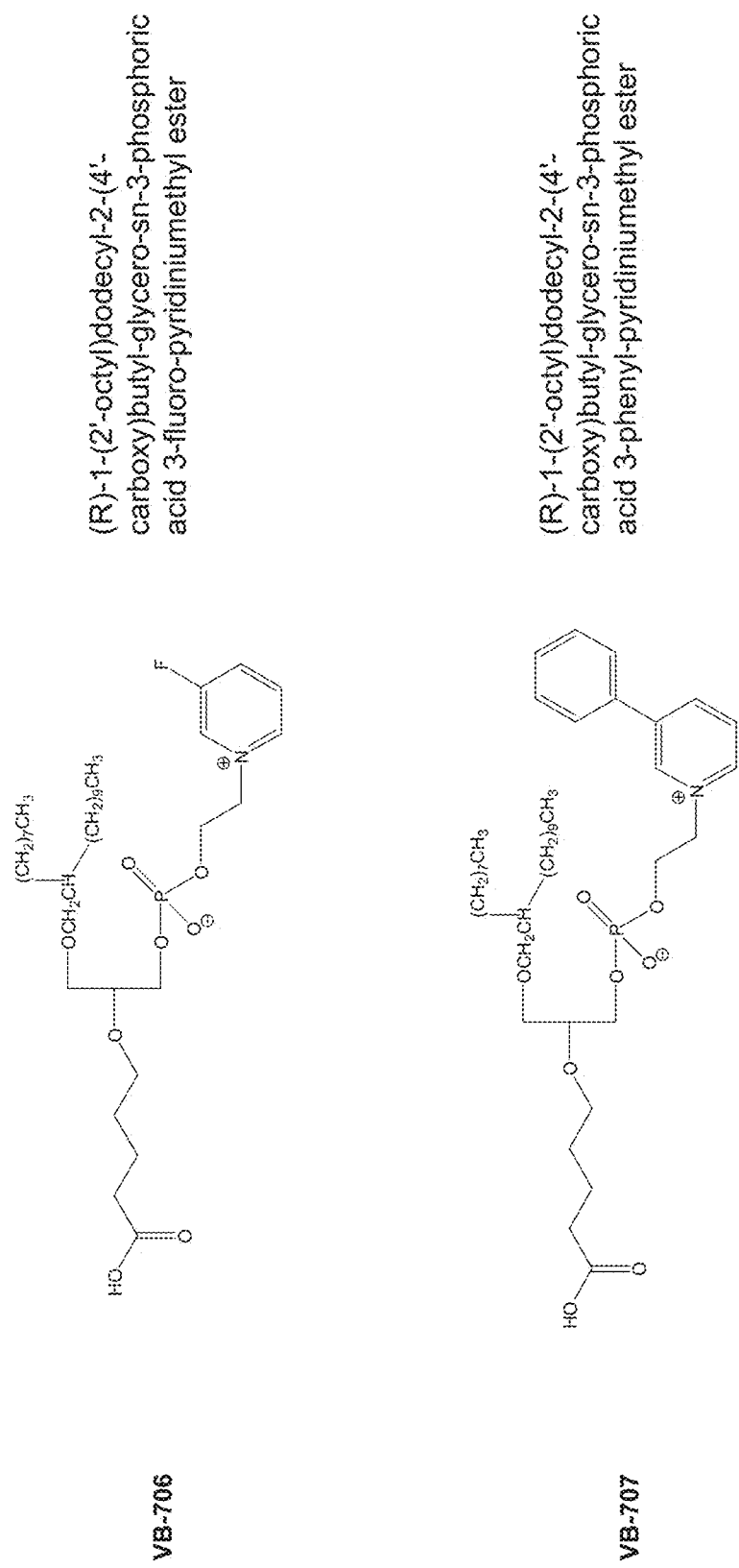

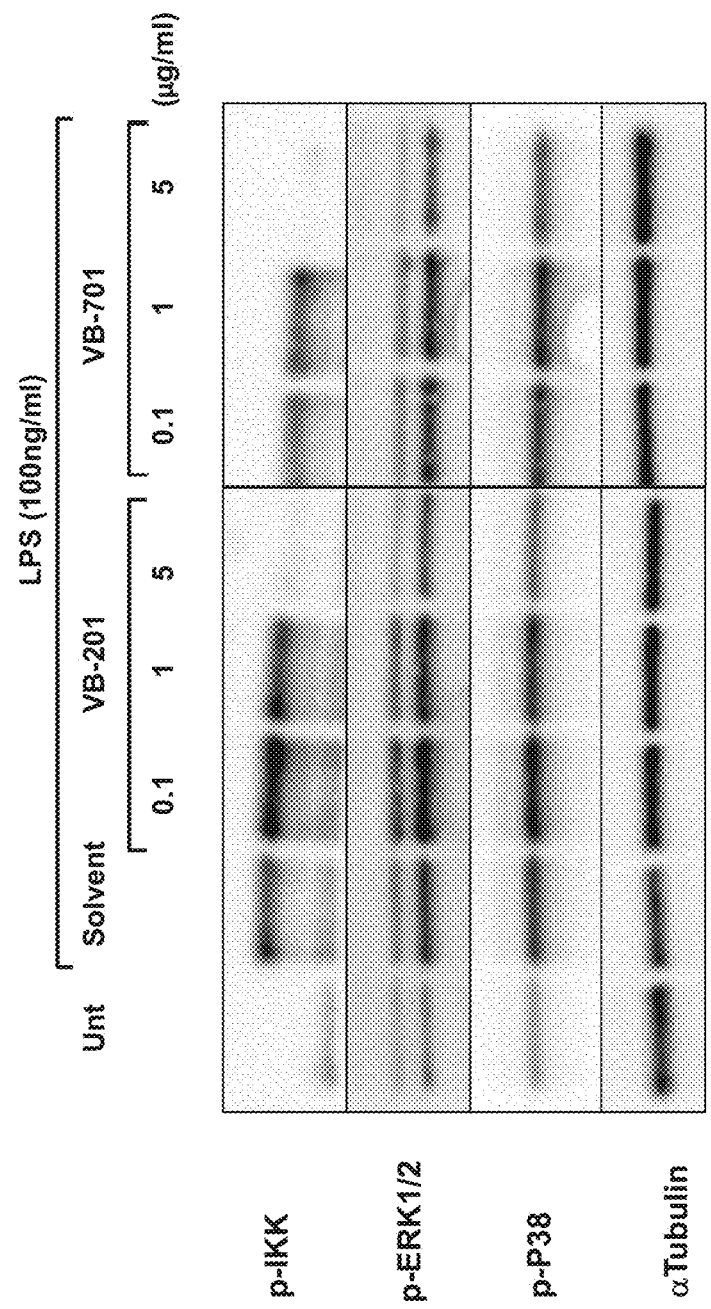

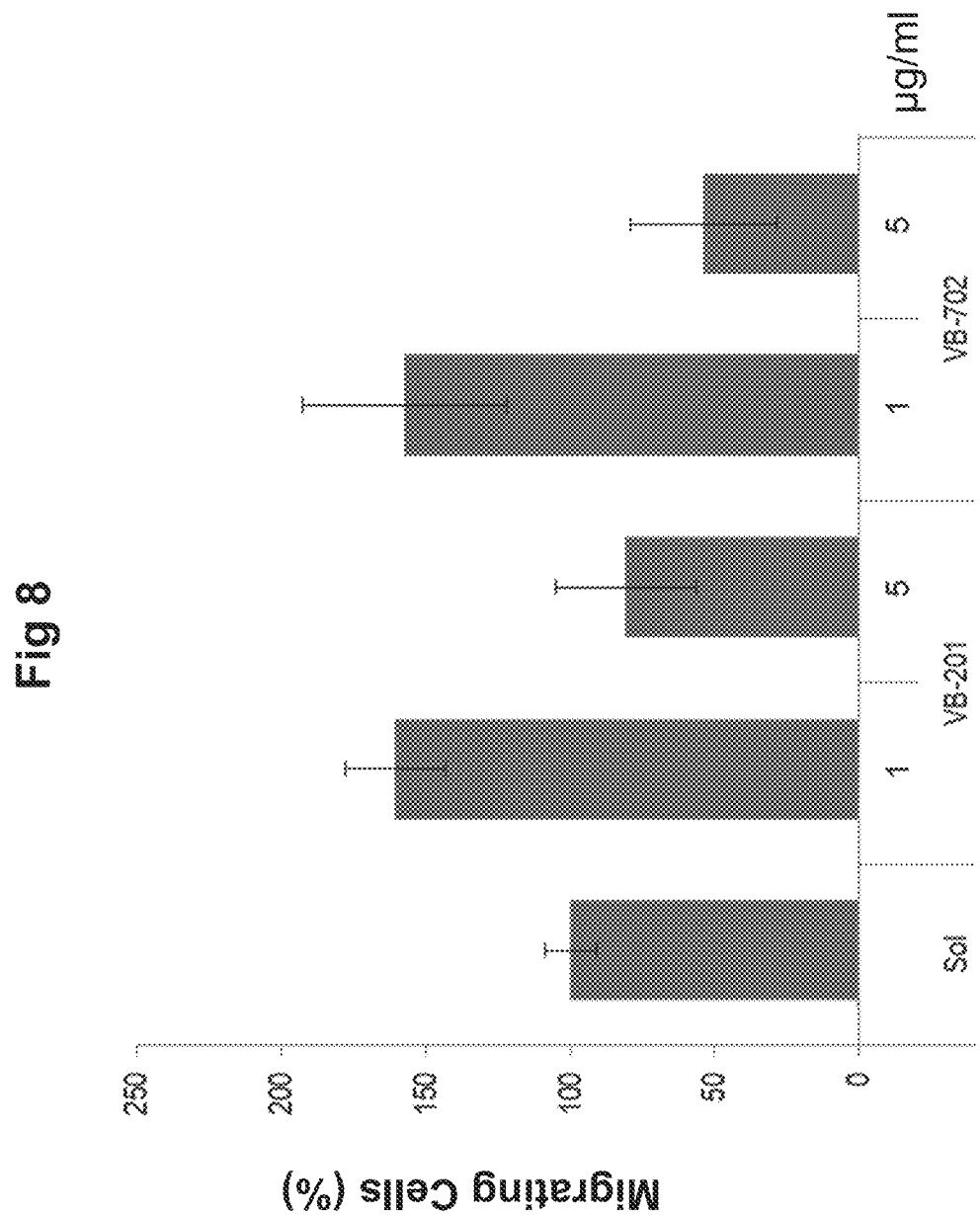

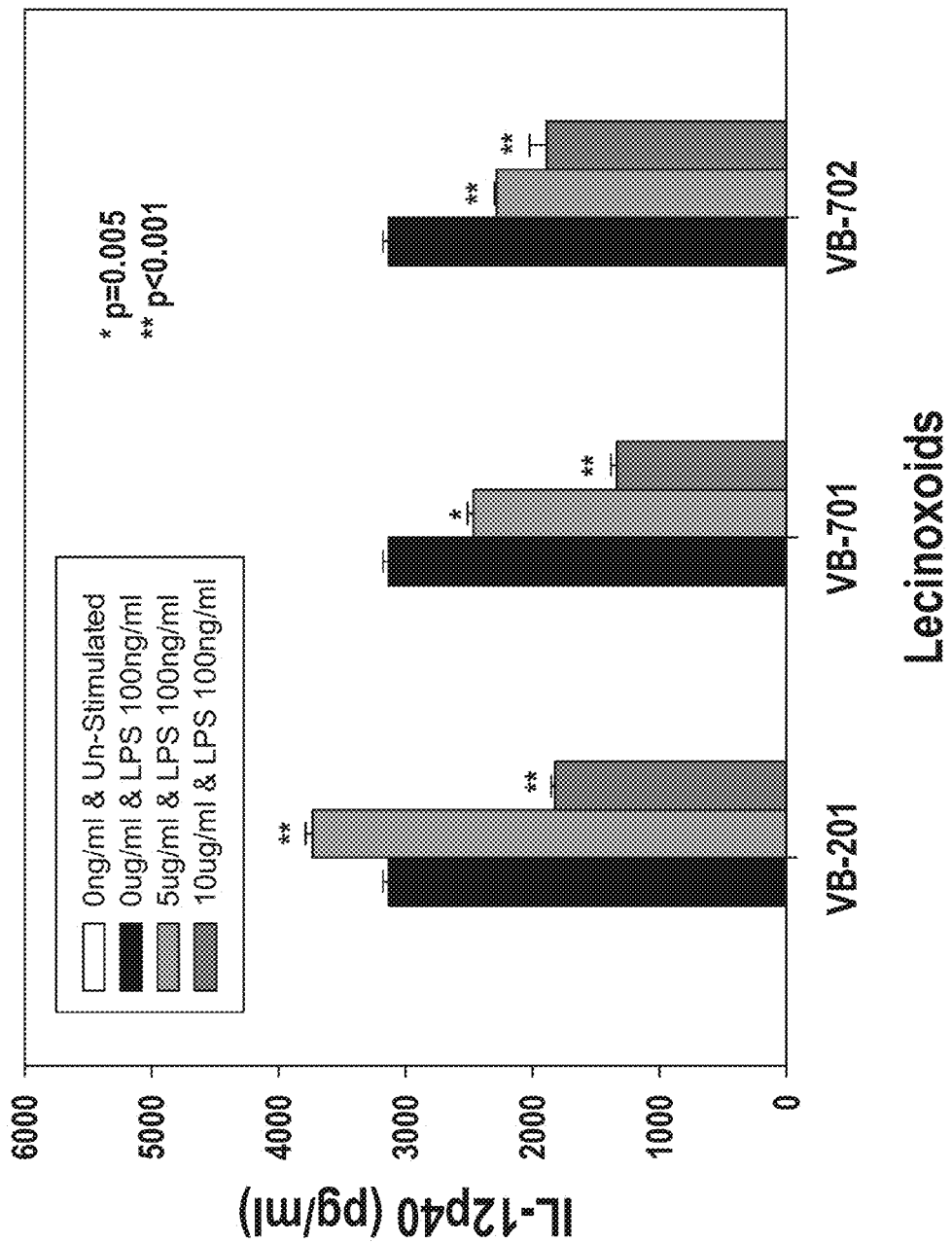

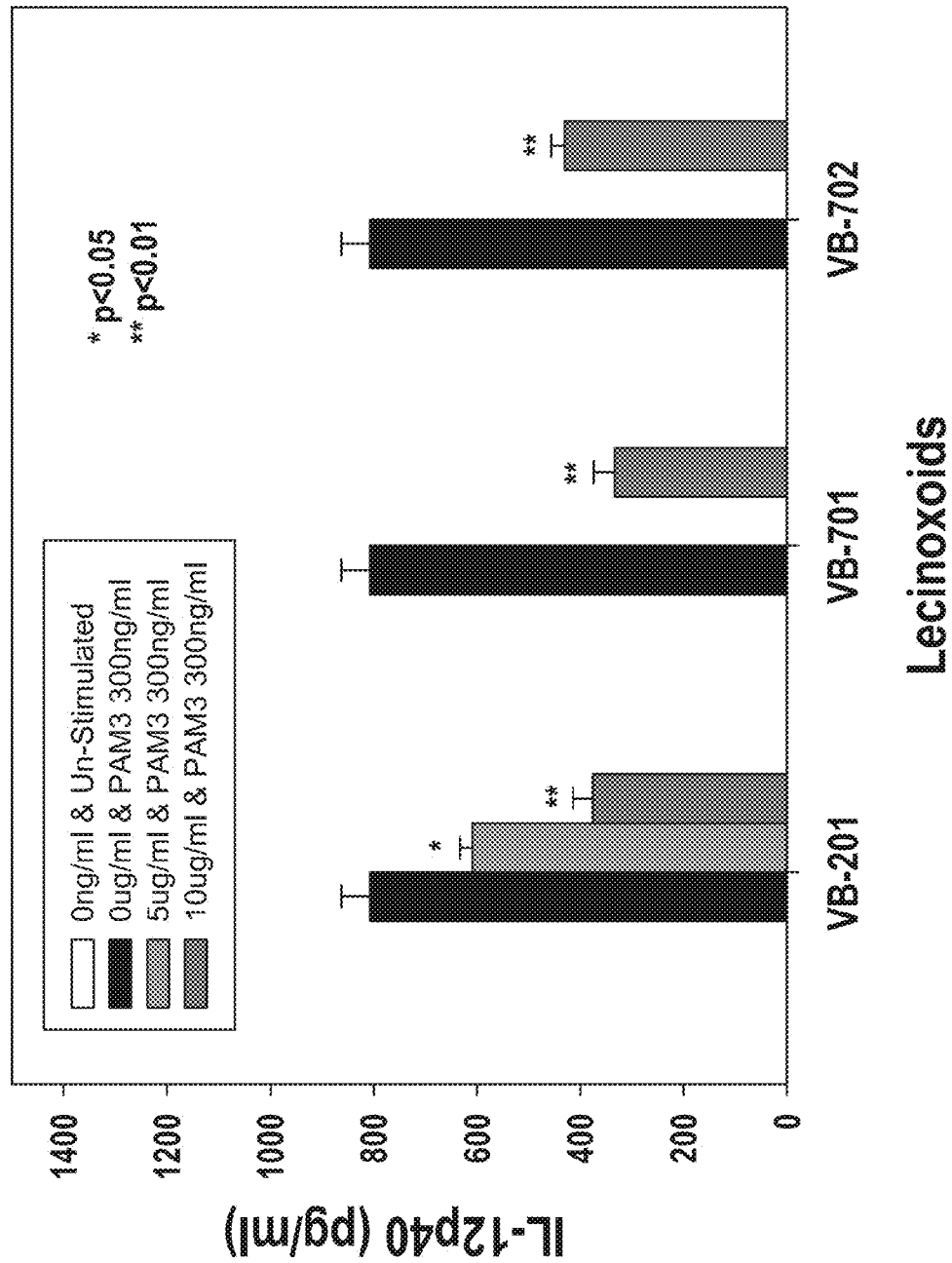

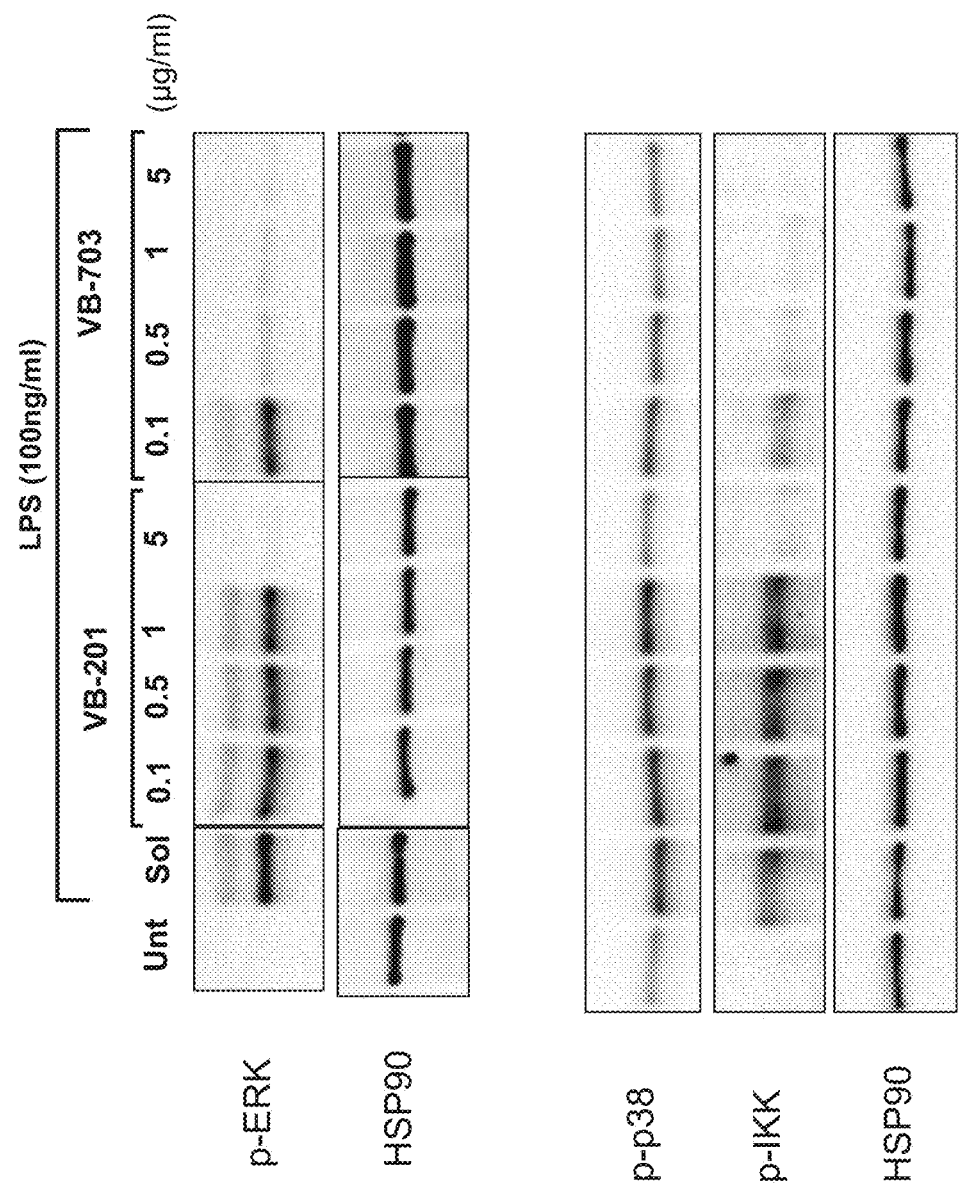

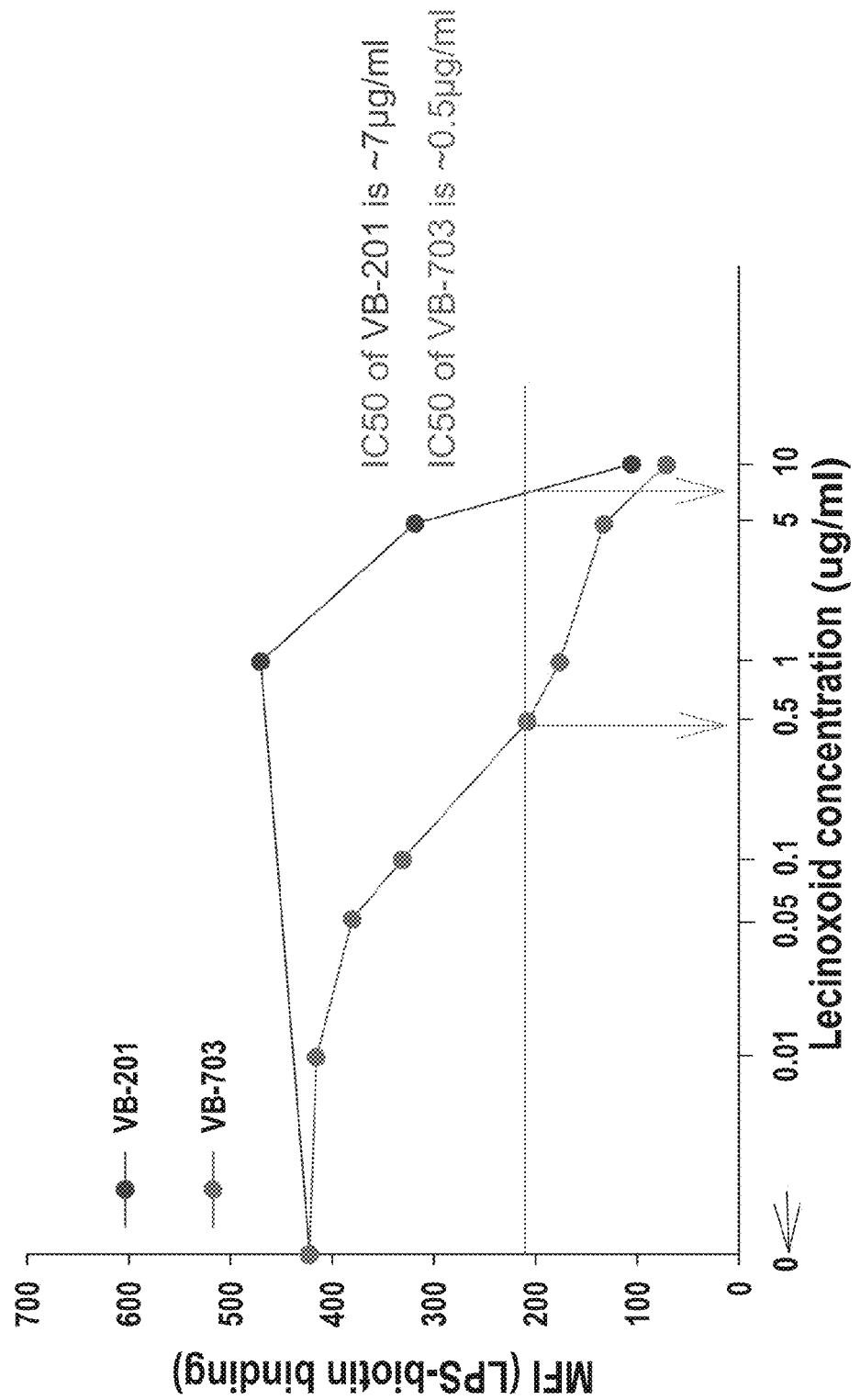

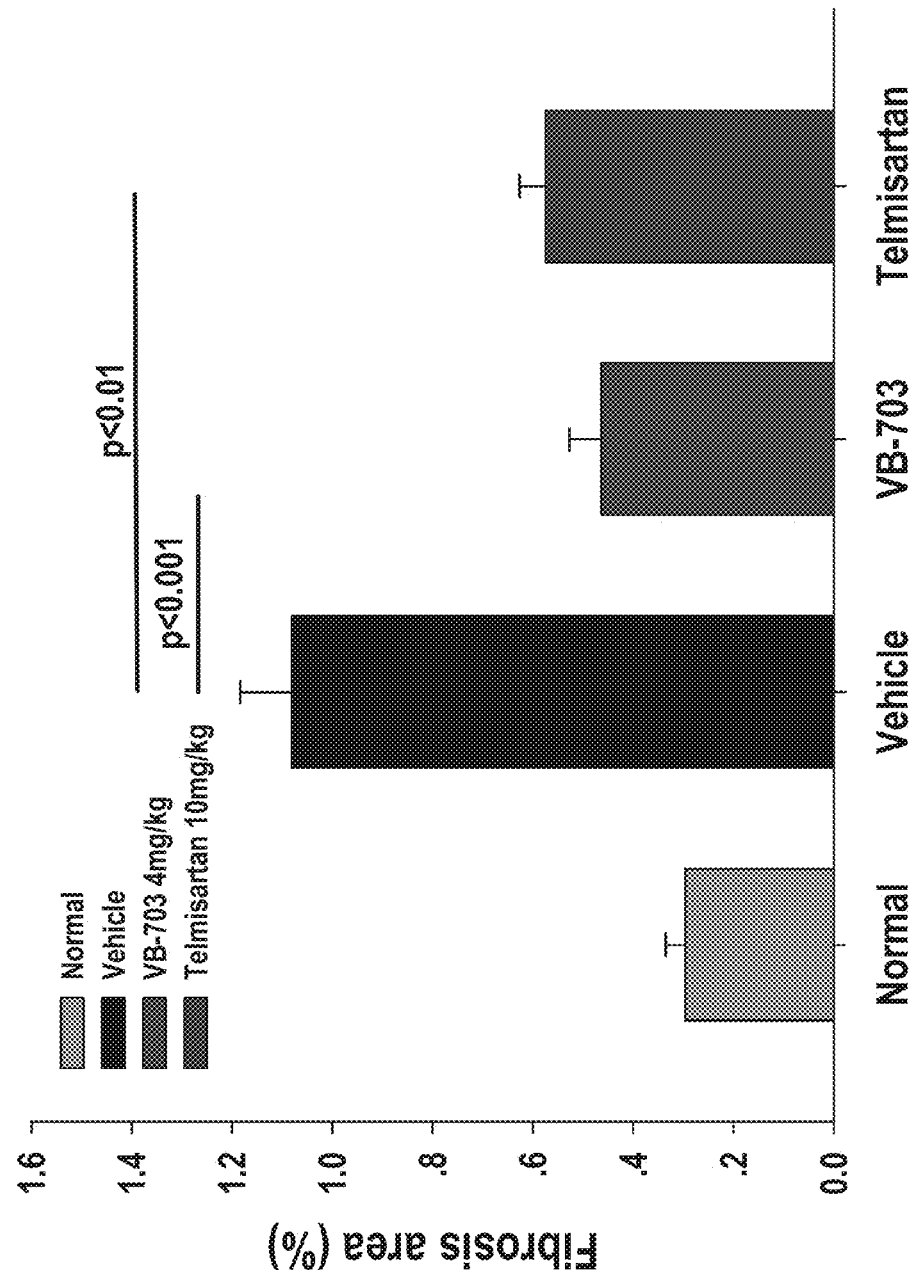

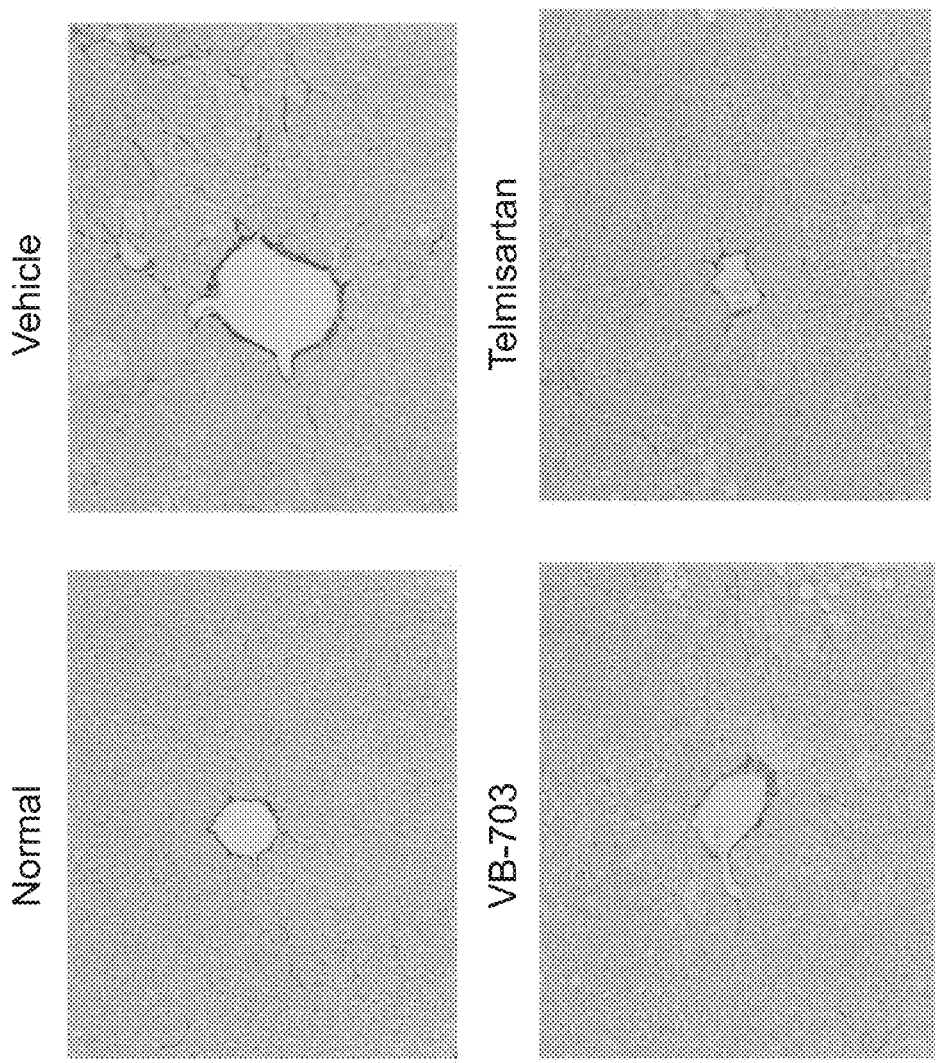

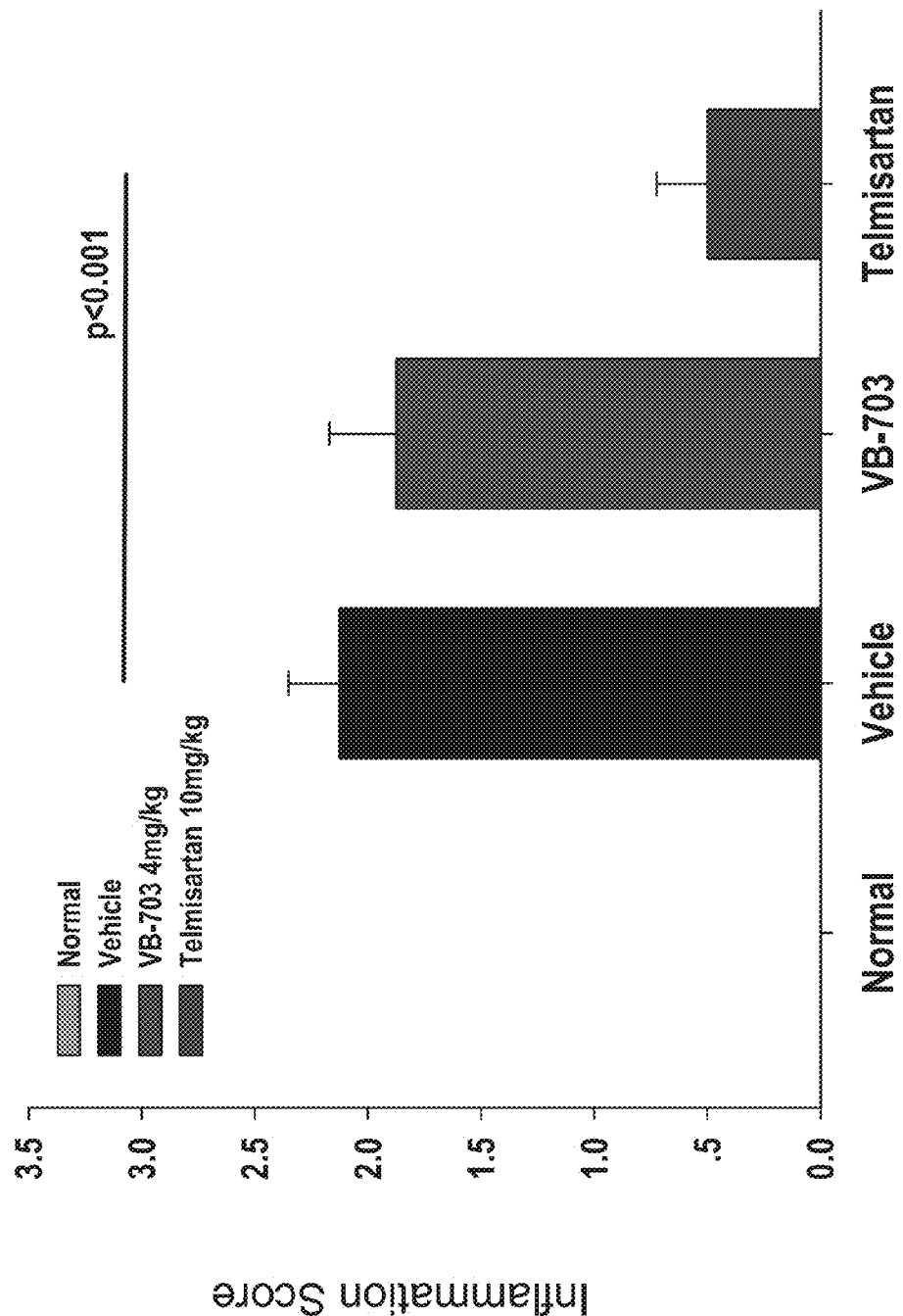

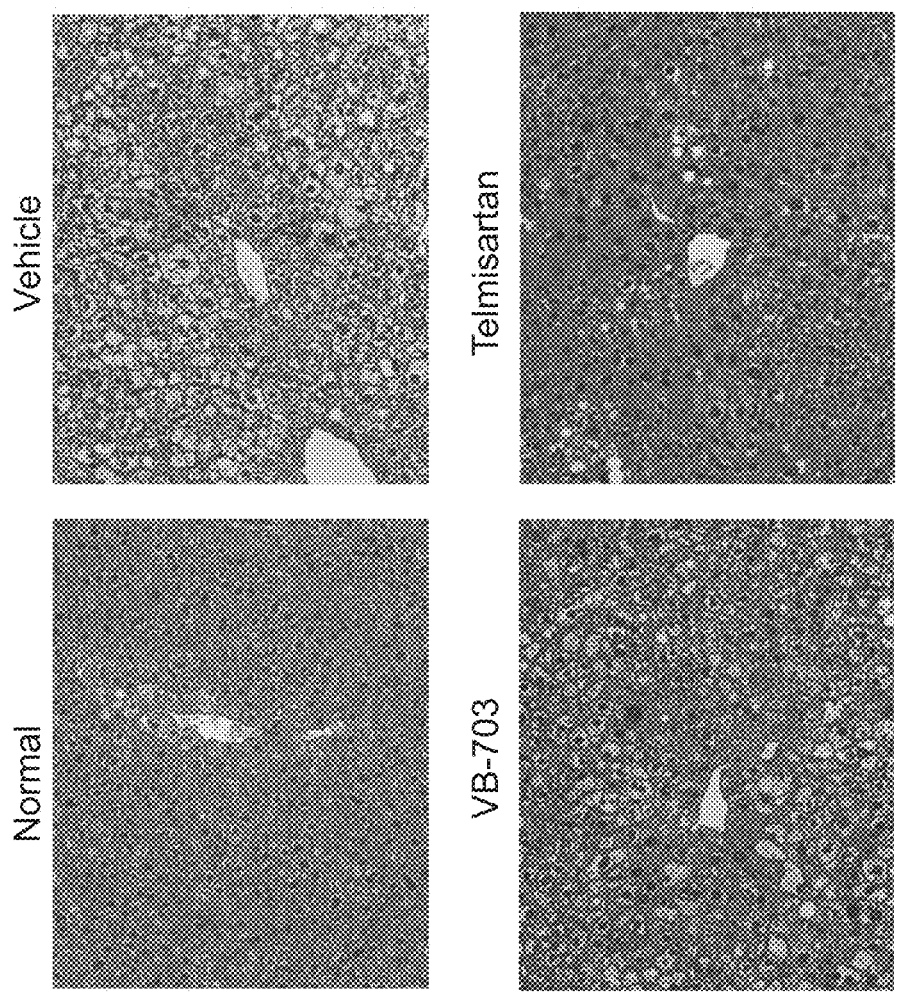

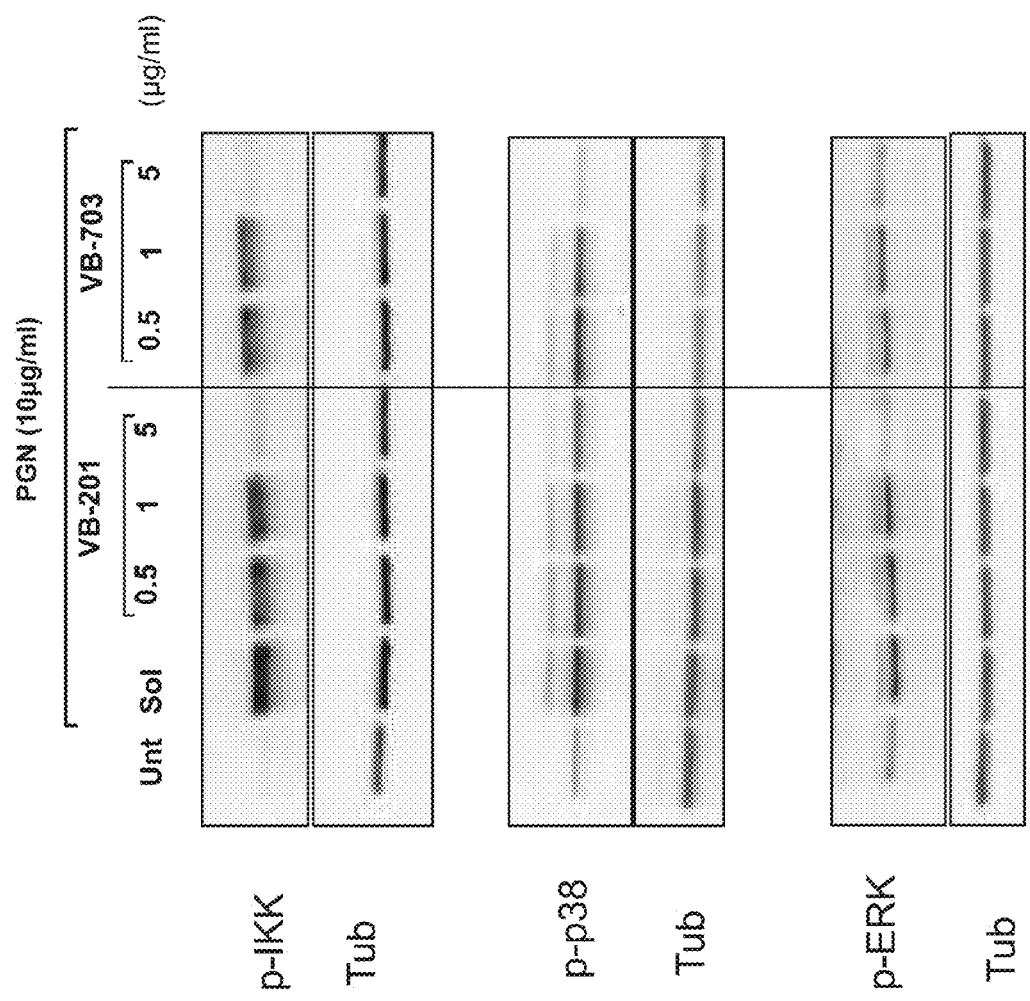

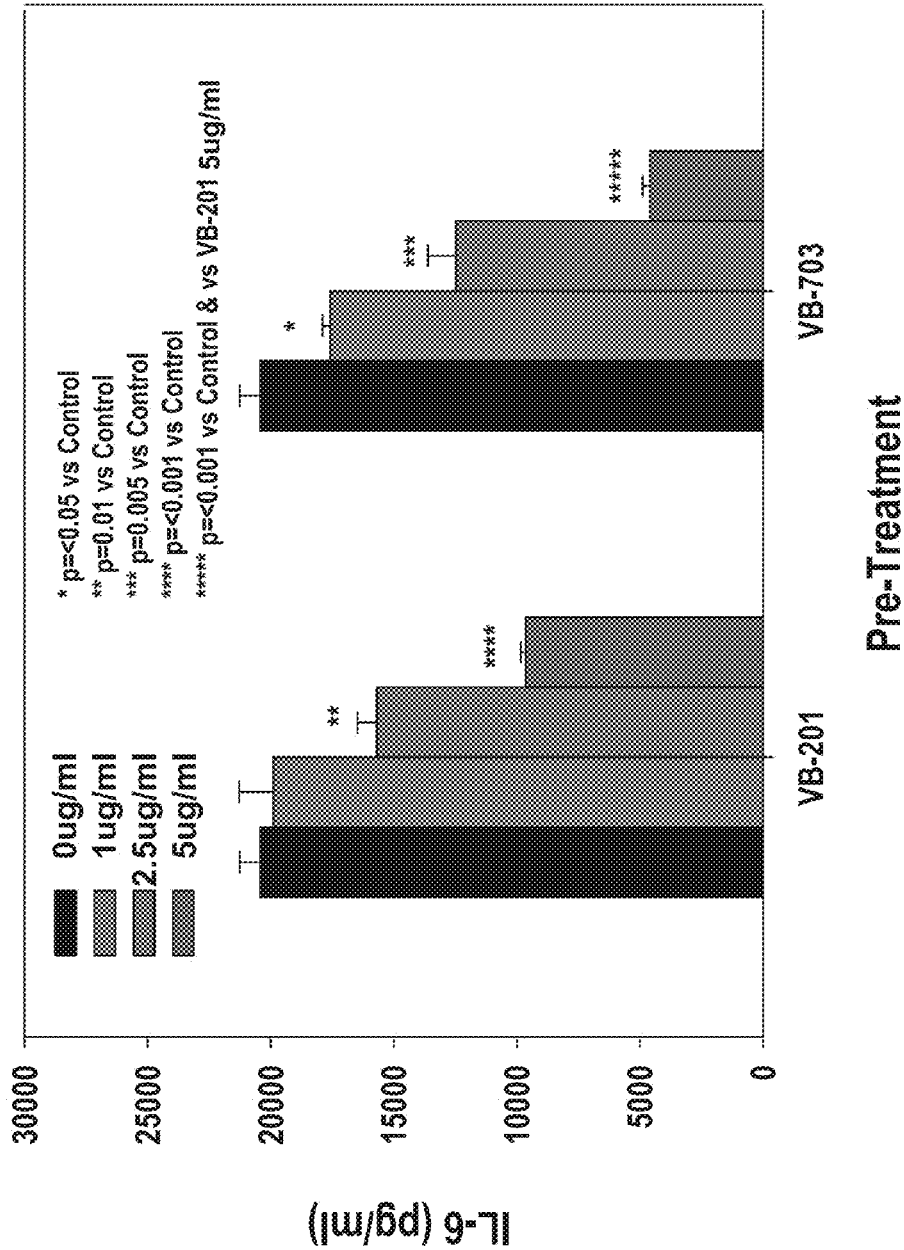

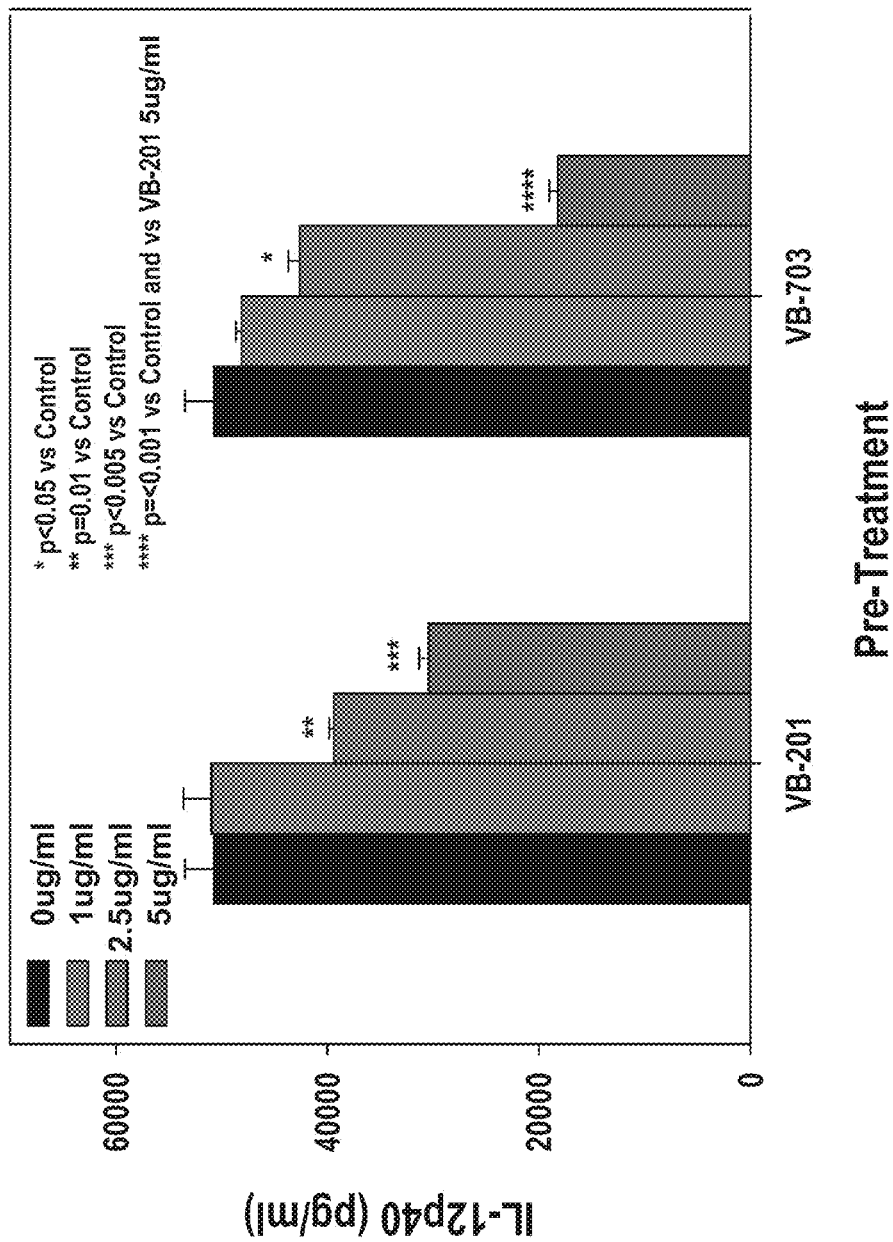

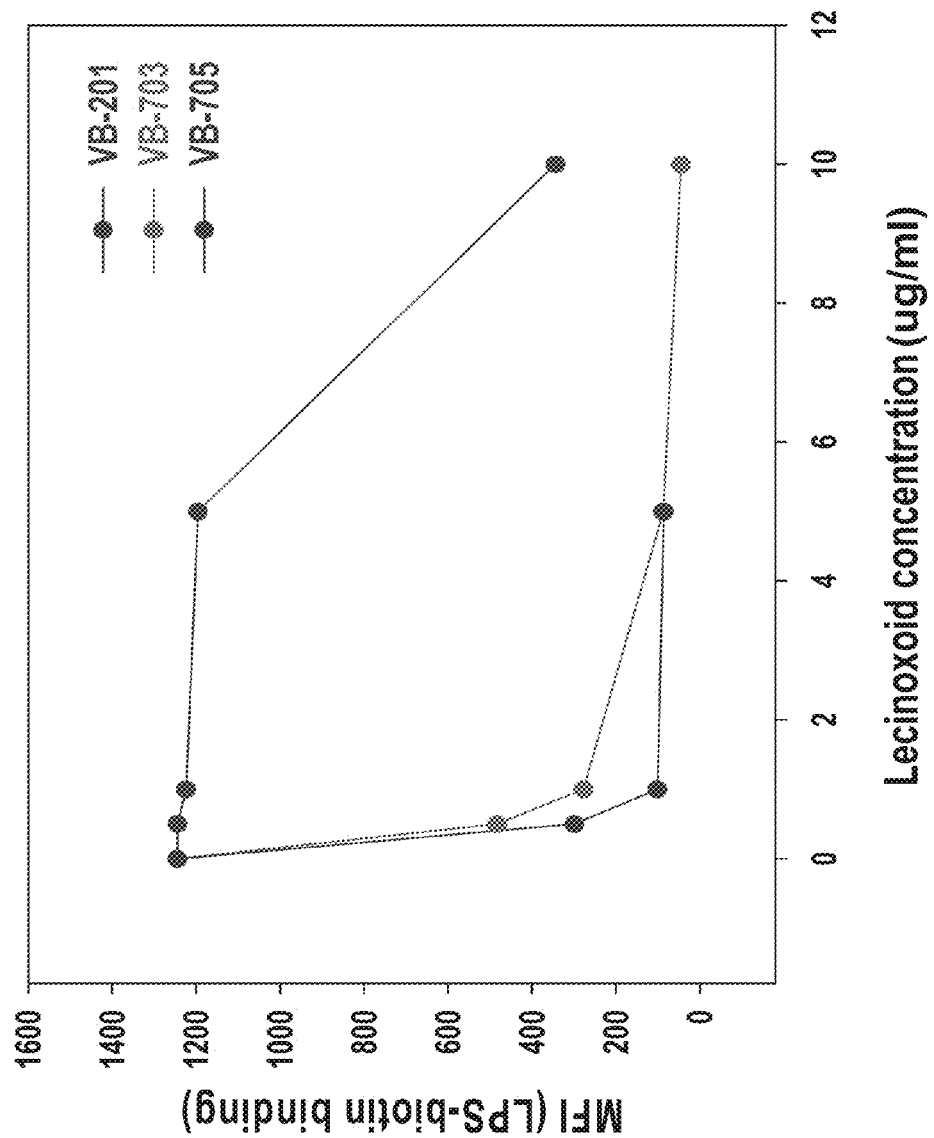

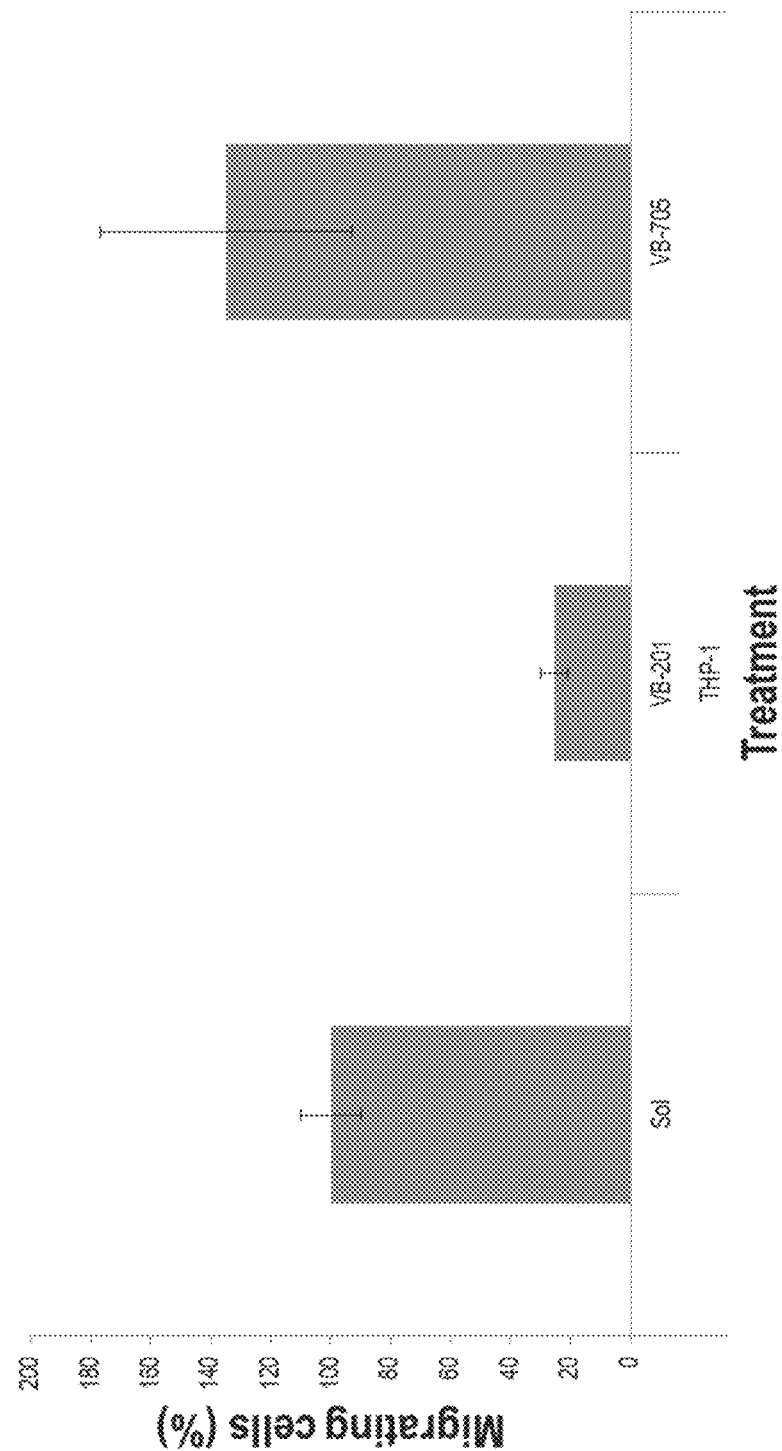

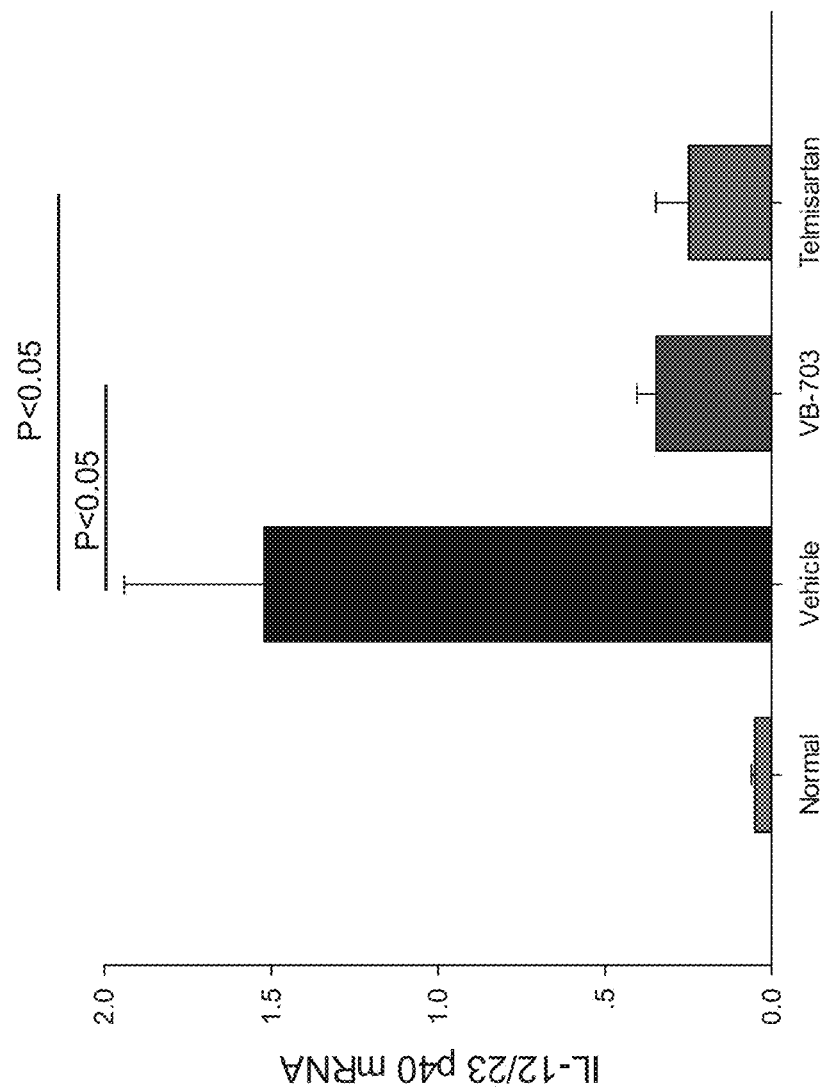

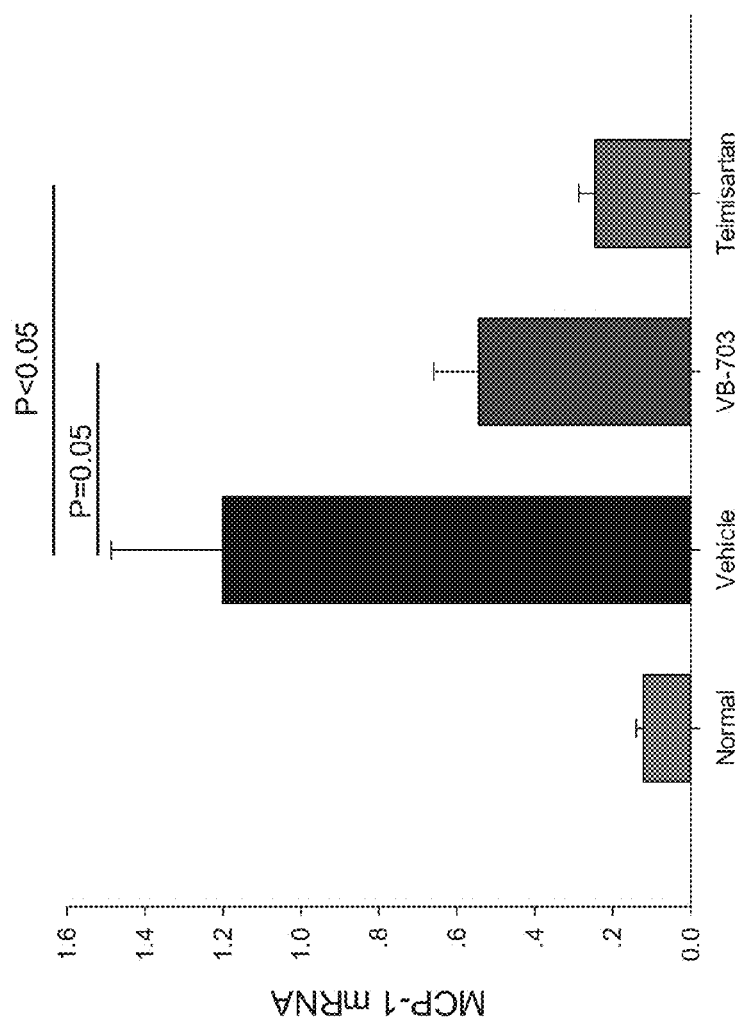

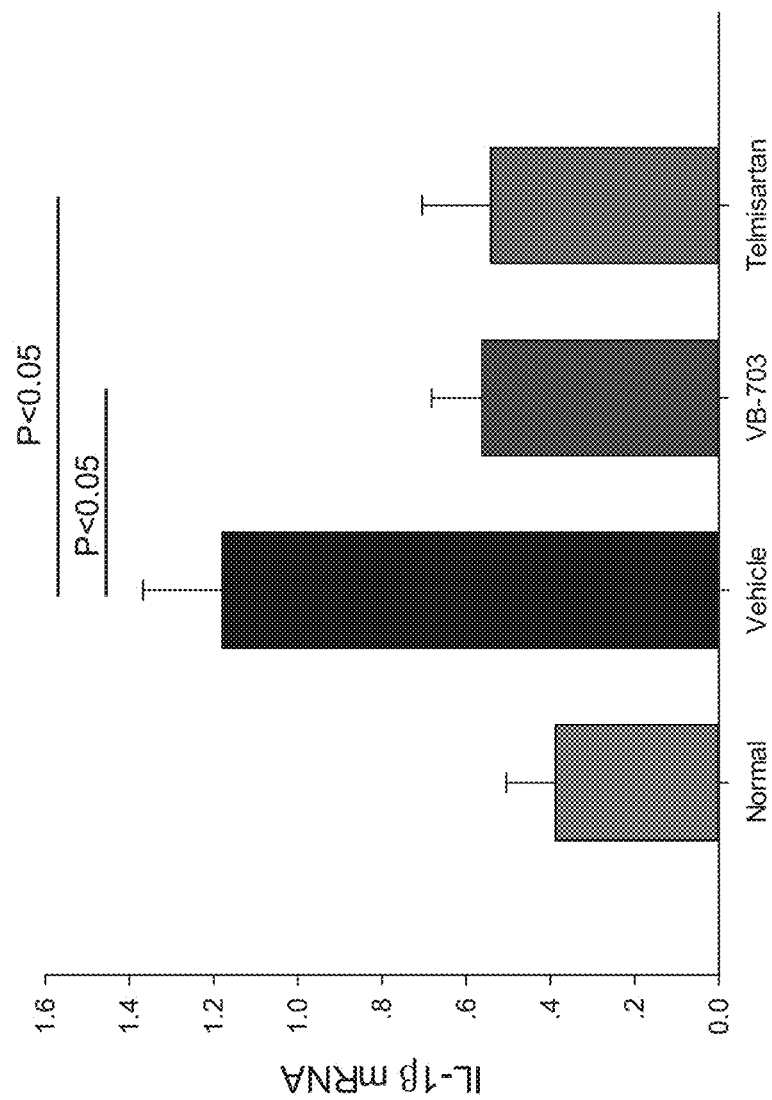

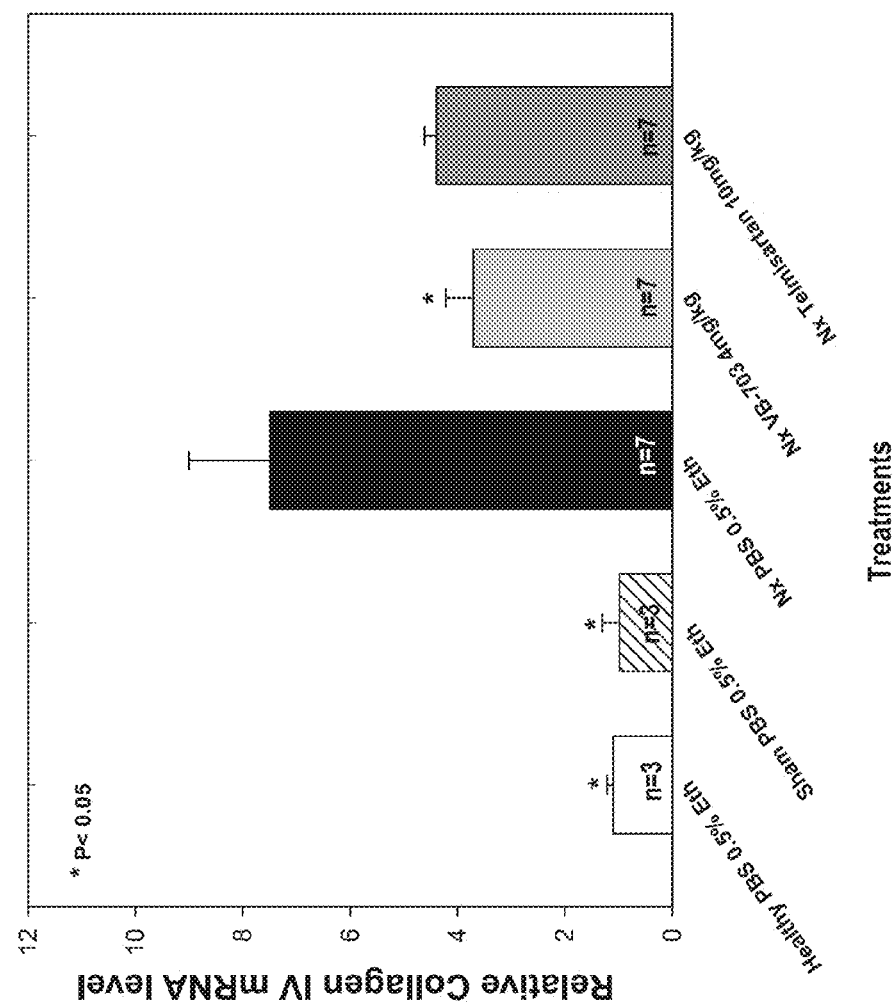

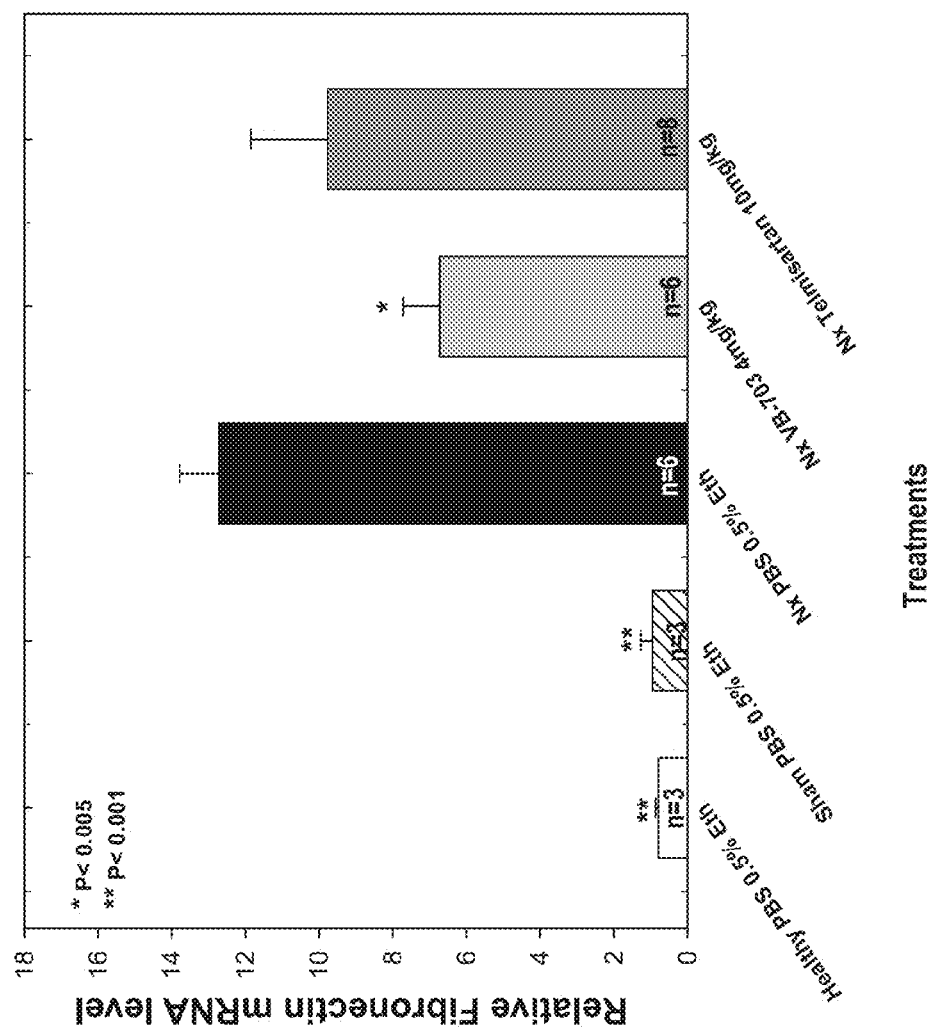

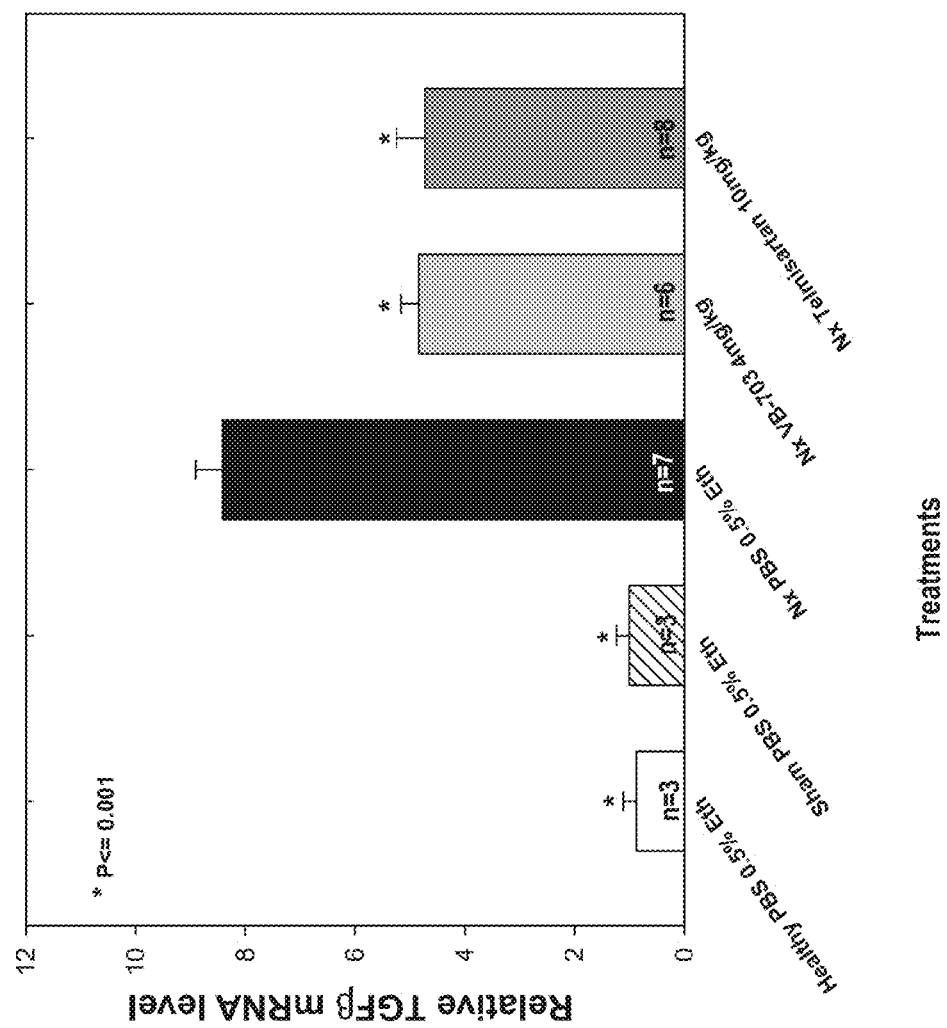

OXIDIZED LIPIDS

CROSS-REFERENCE TO RELATED APPLICATIONS

This application claims priority benefit to U.S. Provisional Appl. No. 62/085,153 filed Nov. 26, 2014, the contents of which are hereby incorporated by reference in their entirety.

FIELD OF THE INVENTION

The present invention, in some embodiments thereof, relates to oxidized lipid compounds and pharmaceutical compositions comprising the same. The invention also relates to methods of making such compounds and compositions, and methods of treating or preventing fibrosis or inflammatory diseases or disorders with such compounds and compositions.

BACKGROUND OF THE INVENTION

Fibrosis is the formation of excess fibrous connective tissue in an organ or tissue, typically as the result of inflammation or damage. Fibrosis encompasses the pathological state of excess deposition of fibrous tissue, as well as the process of connective tissue deposition in healing. Fibrosis is similar to the process of scarring, in that both involve stimulated cells (e.g., fibroblasts) laying down connective tissue, including collagen and glycosaminoglycans.

Fibrosis can be considered as a scarring process in response to chronic diseases where excessive extracellular matrix (ECM) deposition leads to irreversible tissue damage and failure or disturbance of proper organ function. The pathophysiology of fibrosis has generally been studied in the context of the particular organ or tissue affected, including lung, kidney, liver, heart and skin. Loss of metabolic homeostasis and chronic low-grade inflammation may play a role in the pathogenesis of fibrosis. Fibrogenesis is a dynamic process and occurs in four phases: i) initiation, due to injury of the organ/tissue; ii) inflammation and activation of effector cells; iii) enhanced synthesis of ECM; and iv) deposition of ECM with progression to end-organ failure.

Fibrosis can occur in many tissues within the body. Examples include pulmonary fibrosis (lungs), idiopathic pulmonary fibrosis (lungs), cystic fibrosis (lungs), progressive massive fibrosis (lungs), liver fibrosis, cirrhosis (liver), steatohepatitis (fatty liver disease), nonalcoholic fatty liver disease (NAFLD), nonalcoholic steatohepatitis (NASH), endomyocardial fibrosis (heart), myocardial infarction (heart), atrial fibrosis (heart), medastinal fibrosis (soft tissue of mediastinum), myelofibrosis (bone marrow), retroperitoneal fibrosis (soft tissue of the retroperitoneum), nephrogenic systemic fibrosis (skin), keloid (skin), Crohn's disease (intestine), scleroderma/systemic sclerosis (skin, lungs), arthrofibrosis (knee, shoulder, other joints), Peyronie's disease (penis), Dupuytren's contracture (hands, fingers), adhesive capsulitis (shoulder), kidney fibrosis, and focal and segmental glomerulosclerosis (kidney).

One of the major complications of insulin resistance and metabolic syndrome is nonalcoholic fatty liver disease (NAFLD), which can progress from fatty liver to liver inflammation (NASH) and liver fibrosis. It is believed that due to intestinal barrier leakage, accompanied by overgrowth and changes in the composition of gut flora, bacterial components travel through the portal vein into the liver, where they encounter toll like receptors (TLRs).

TLRs are a family of receptors imperative for the innate immune response against microbial invasion. TLRs can be divided into two major subgroups based on their cellular localization. Plasma membrane expressed TLRs include TLR1, TLR2, TLR4, TLR5, and TLR6, whereas the intracellular TLRs include TLR3, TLR7, TLR8, and TLR9. The interaction between TLRs with their cognate agonists instigates a cascade of cues which include recruitment of the adaptor molecules MyD88/TRIF and downstream phosphorylation of MAPK kinases and NF-κB. These events culminate in the secretion of proinflammatory cytokines, including IL-12/23, IL-6 and TNF-α. TLR2 forms a heterodimer with TLR1 which recognizes bacterial triacylated lipopeptides, and a heterodimer with TLR6 which recognizes bacterial diacylated lipopeptides. TLR4 coupled to MD2 in complex with lipopolysaccharide-binding protein (LBP) and the co-receptor CD14 bind lipopolysaccharide (LPS) from gram negative bacteria.

Liver resident kupffer and hepatic stellate cells (HSC) express TLR2 which recognize triacylated lipopeptides from Gram-negative bacteria and *mycoplasma* and diacylated lipopeptides from Gram-negative bacteria and *mycoplasma* and TLR4 and its co-receptor CD14 which recognize lipopolysaccharide (LPS) from gram-negative bacteria. Both TLR2 and TLR4 can also bind to danger associated molecular patterns released from injured tissues. These TLR2 and TLR4 complexes mediate the production of pro-inflammatory cytokines and fibrogenic response by kupffer and stellate cells. Pre-clinical studies showed that nonalcoholic steatohepatitis and liver fibrosis are inhibited in TLR2 and TLR4 deficient mice, indicating its role in disease pathogenesis. In humans, LPS plasma levels are elevated in NAFLD patients and alterations in TLR4 and CD14 genes are associated with risks of developing nonalcoholic steatohepatitis and fibrogenesis.

Monocytes are key players in the immune system, with critical roles in innate and adaptive immunity, immune surveillance and particle scavenging. Whereas a subset of monocytes is "resident" and recruited to tissues independently of inflammatory stimuli to assist in steady-state surveillance, wound-healing and resolution of inflammation, the absolute majority (80-90%) of human circulating monocytes is classified as "inflammatory". These monocytes can sense inflammatory stimuli and quickly migrate through the vascular or lymphatic endothelium to the periphery, where they can differentiate into macrophages and dendritic cells (DCs) which cooperate with additional cell subsets (such as Th1-cells) to promote inflammation. While playing a necessary role in host defense, monocytes were nonetheless identified as critical mediators of several inflammatory diseases, including atherosclerosis, rheumatoid arthritis (RA) and multiple sclerosis (MS). Suppressing the accumulation of unwanted monocytes/macrophages in a chronically inflamed tissue has therapeutic potential, and migration inhibitors have accordingly demonstrated promising anti-inflammatory results in animal models and clinical trials.

Renal fibrosis (kidney fibrosis) is a wound healing/scarring response following kidney injury that occurs in many forms of chronic kidney disease (CKD). Following kidney injury, resident fibroblasts are activated by various pro-inflammatory and pro-fibrotic stimuli. Activated fibroblasts, also called myofibroblasts, produce excessive ECM proteins that accumulate in the interstitium, and therefore are considered a mediator of renal fibrosis. Regardless of the primary insult leading to renal fibrosis, chronic inflammation appears to be a process heralding renal fibrogenesis. Elevated levels of inflammatory markers were associated with an increased risk of developing CKD. Induction of various pro-inflammatory cytokines interleukin (IL)-6, IL-8, IL-10, chemokine (C—C motif) ligand 2 (CCL2), tumor necrosis factor-α (TNF-α) and adhesion molecules (intercellular adhesion molecule-1 and vascular cell adhesion molecule-1) attracted the transmigration of macrophages and T cells from the circulation to the interstitium, thereby further enhancing the inflammatory state. Evidence suggests that TLRs and macrophages are associated with the pathogenesis of renal fibrosis.

Fibrosis or inflammatory diseases or disorders can cause severe morbidity and deleterious effects on patients' daily function, activity of daily living (ADL) and quality of life, and can lead to a poor prognosis. For example, idiopathic pulmonary fibrosis (IPF) is a chronic intractable disease associated with worsening and debilitating shortness of breath. IPF patients become oxygen dependent, and have an average median survival time of three years and a five year survival rate of 20% to 40% after diagnosis. Therefore, the development of new therapies for fibrosis and inflammatory diseases or disorders is needed.

SUMMARY OF THE INVENTION

In some embodiments, the present invention provides oxidized lipid compounds according to Formula 1,

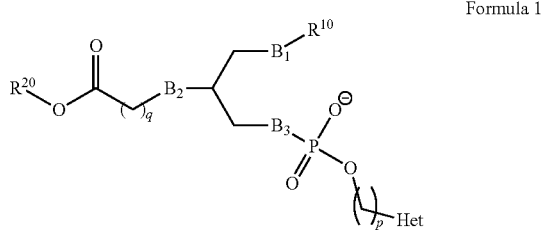

Formula 1 or a stereoisomer, a stereoisomeric mixture, or a salt thereof, wherein each of $B_1$, $B_2$, and $B_3$ is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy, and oxo;

wherein $R^{10}$ is a $C_{2-28}$ alkyl optionally substituted by one to five $R^{11}$ substituents, wherein each $R^{11}$ is independently selected from the group consisting of alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy, and amino;

wherein p is an integer selected from 1-10;
wherein q is an integer selected from 1-26;
wherein $R^{20}$ is selected from the group consisting of hydrogen, alkyl, alkenyl, alkynyl, cycloalkyl, aryl, and heteroaryl; and
wherein Het is a heteroalicyclic ring or a heteroaryl.

Suitable $B_1$, $B_2$, and $B_3$ for Formula 1 are defined herein. In some embodiments, $B_1$ is O. In some embodiments, $B_2$ is O. In some embodiments, $B_3$ is O. In some embodiments, at least two of $B_1$, $B_2$, and $B_3$ are O, e.g., $B_1$, $B_2$ are O and $B_3$ is O or S; $B_1$, $B_3$ are O and $B_2$ is O or S; or $B_2$, $B_3$ are O and $B_1$ is O or S. In some embodiments, $B_1$ is S. In some embodiments, $B_2$ is S. In some embodiments, $B_3$ is S. In some embodiments, at least two of $B_1$, $B_2$, and $B_3$ are S, e.g., $B_1$, $B_2$ are S and $B_3$ is O or S; $B_1$, $B_3$ are S and $B_2$ is O or S; or $B_2$, $B_3$ are S and $B_1$ is O or S. In some embodiments, all of $B_1$, $B_2$, and $B_3$ are O. In some embodiments, all of $B_1$, $B_2$, and $B_3$ are S.

Suitable $R^{10}$ for Formula 1 are defined herein. In some embodiments, $R^{10}$ is a $C_{2-28}$ alkyl. In some embodiments, $R^{10}$ is a straight chain $C_{2-28}$ alkyl, e.g., an alkyl chain having 4, 5, 6, 7, 8, 9, 10, 11, 12, 13, 14, 15, 16, 17, 18, 19, 20, 21, 22, 23, 24, 25, 26, 27, or 28 carbons, substituted or unsubstituted. In some embodiments, $R^{10}$ is a straight chain $C_{2-28}$ alkyl, e.g., an alkyl chain having 4, 5, 6, 7, 8, 9, 10, 11, 12, 13, 14, 15, 16, 17, 18, 19, 20, 21, 22, 23, 24, 25, 26, 27, or 28 carbons, substituted by one to five $R^{11}$ substituents, wherein each $R^{11}$ is independently as defined herein, e.g., a halogen (e.g., F) or an alkyl (e.g., a $C_{1-10}$ alkyl). In some embodiments, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl. In some embodiments, $R^{10}$ is hexadecyl. In some embodiments, $R^{10}$ is (2'-octyl)dodecyl. In some embodiments, $R^{10}$ is eicosanyl.

Suitable $R^{20}$ for Formula 1 are defined herein. In some embodiments, $R^{20}$ is a hydrogen or an alkyl. In some embodiments, $R^{20}$ is hydrogen. In some embodiments, $R^{20}$ is an alkyl, e.g., a $C_{1-4}$ alkyl (e.g., methyl, ethyl, propyl, isopropyl, n-butyl, sec-butyl, iso-butyl, or tert-butyl). In some embodiments, $R^{20}$ is methyl.

Suitable values for p and q in Formula 1 are defined herein. In some embodiments, q is an integer of 1-10, e.g., 1, 2, 3, 4, 5, 6, 7, 8, 9, or 10. In some embodiments, q is 4. In some embodiments, p is an integer of 1-7, e.g., 1, 2, 3, 4, 5, 6, or 7. In some embodiments, p is 2.

Suitable Het for Formula 1 are defined herein. In some embodiments, Het is a heteroaryl. In some embodiments, Het is a monocyclic heteroaryl. In some embodiments, Het is a nitrogen containing heteroaryl (e.g., monocyclic heteroaryl). In some embodiments, Het is a monocyclic heteroaryl containing 1, 2, 3, or 4 nitrogen atoms. In some embodiments, Het is a 6-member ring monocyclic heteroaryl, e.g., pyridine, pyrimidine, pyridazine, pyrazine, triazine, etc. In some embodiments, Het is a 5-member ring monocyclic heteroaryl, e.g., imidazole, thiazole, isothiazole, oxazole, isoxazole, oxidiazole, pyrazole, triazole, etc. In some embodiments, Het is a bicyclic heteroaryl containing, e.g., 1-nitrogen atoms, e.g., quinoline, isoquinoline, quinazoline, thienopyridine, thienopyrimidine, pyrrolopyridine, imidazopyridine, etc. In any of the embodiments described herein, Het can be a nitrogen containing heteroaryl, wherein a nitrogen atom of the heteroaryl is directly connected to the alkylene chain, i.e., —$(CH_2)_p$— in Formula 1 to form a cation. In some embodiments, Het is pyridine, wherein the nitrogen atom of the pyridine is directly connected to the alkylene chain, i.e., —$(CH_2)_p$— in Formula 1 to form a pyridinium salt (e.g., an internal salt or an external salt as described herein). In some embodiments, Het is an unsubstituted pyridine, wherein the nitrogen atom of the pyridine is directly connected to the alkylene chain, i.e., —$(CH_2)_p$— in Formula 1. In some embodiments, Het is a substituted pyridine, wherein the nitrogen atom of the pyridine is directly connected to the alkylene chain, i.e., —$(CH_2)_p$— in Formula 1, wherein the pyridine is substituted by one to five (e.g., 1, 2, 3, 4, or 5) $R^{12}$ substituents, wherein each $R^{12}$ is independently as defined herein, e.g., a halogen (e.g., F, Cl), a $C_{6-10}$ aryl (e.g., phenyl), a heteroaryl, or an alkyl (e.g., a $C_{1-10}$ alkyl, e.g., a $C_{1-4}$ alkyl (e.g., methyl, ethyl, propyl, isopropyl, n-butyl, sec-butyl, iso-butyl, tert-butyl)). In some embodiments, Het is a substituted pyridine and the pyridine is substituted by one $R^{12}$ substituent at the 2-, 3-, or 4-position of the pyridine, wherein $R^{12}$ is as defined herein, for example, a halogen (e.g., F, Cl), a phenyl, or a methyl. In some embodiments, Het is 3-fluoro-pyridine or 3-phenyl-pyridine.

In some embodiments, an oxidized lipid of the invention is a compound having a structure according to Formula 2:

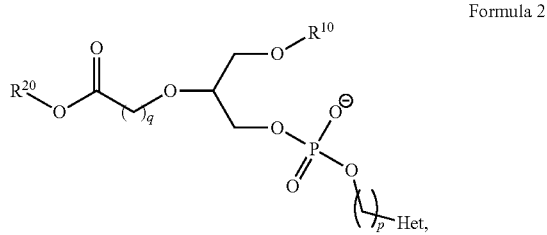

Formula 2 or a stereoisomer, a stereoisomeric mixture, or a salt thereof. Suitable $R^{10}$, $R^{20}$, p, q, and Het are those as defined herein for Formula 1.

In some embodiments according to Formula 2, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl; $R^{20}$ is hydrogen or an alkyl, e.g., a $C_{1-4}$ alkyl (e.g., methyl, ethyl, propyl, isopropyl, n-butyl, sec-butyl, iso-butyl, or tert-butyl); q is an integer of 1-10, e.g., 1, 2, 3, 4, 5, 6, 7, 8, 9, or 10; p is an integer of 1-7, e.g., 1, 2, 3, 4, 5, 6, or 7; and Het is an unsubstituted pyridine, wherein the nitrogen atom of the pyridine is directly connected to the alkylene chain, i.e., —$(CH_2)_p$— in Formula 1, or Het is a substituted pyridine, wherein the nitrogen atom of the pyridine is directly connected to the alkylene chain, i.e., —$(CH_2)_p$— in Formula 1, wherein the pyridine is substituted by one to five (e.g., 1, 2, 3, 4, or 5) $R^{12}$ substituents, wherein each $R^{12}$ is independently as defined herein, e.g., a halogen (e.g., F, Cl), a $C_{6-10}$ aryl (e.g., phenyl), a heteroaryl (e.g., monocyclic heteroaryl), or an alkyl (e.g., a $C_{1-10}$ alkyl, e.g., a $C_{1-4}$ alkyl (e.g., methyl, ethyl, propyl, isopropyl, n-butyl, sec-butyl, iso-butyl, tert-butyl)). In some embodiments, Het is a substituted pyridine and the pyridine is substituted by one $R^{12}$ substituent at the 2-, 3-, or 4-position of the pyridine, wherein $R^{12}$ is as defined herein, for example, a halogen (e.g., F, Cl), a phenyl, or a methyl. In some embodiments, Het is 3-fluoro-pyridine or 3-phenyl-pyridine.

In some embodiments, an oxidized lipid of the invention is a compound having a structure according to Formula 3:

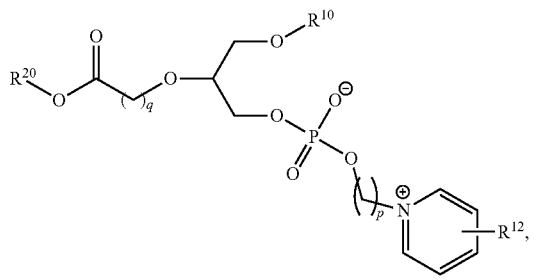

Formula 3 or a stereoisomer, a stereoisomeric mixture, or a salt thereof, wherein $R^{10}$, $R^{11}$, $R^{12}$, $R^{20}$, p, and q are as defined herein for Formula 1.

In some embodiments according to Formula 3, $R^{10}$ is selected from the group consisting of hexadecyl, eicosanyl and (2'-octyl)dodecyl; $R^{20}$ is hydrogen or a $C_{1-4}$ alkyl (e.g., methyl, ethyl, propyl, isopropyl, n-butyl, sec-butyl, iso-butyl, or tert-butyl); q is an integer of 2-6, e.g., 2, 3, 4, 5, or 6; p is an integer of 2-5, e.g., 2, 3, 4, or 5; and the pyridine is substituted by 0 to 3 (e.g., 0, 1, 2, or 3) $R^{12}$ substituents, wherein each $R^{12}$ is independently as defined herein, e.g., a halogen (e.g., F, Cl), a $C_{6-10}$ aryl (e.g., phenyl), a heteroaryl, or a $C_{1-4}$ alkyl (e.g., methyl, ethyl, propyl, isopropyl, n-butyl, sec-butyl, iso-butyl, tert-butyl). In some embodiments, $R^{10}$ is selected from the group consisting of hexadecyl, eicosanyl and (2'-octyl)dodecyl; $R^{20}$ is hydrogen or methyl; q is 2, 3, 4, 5, or 6; p is 2, 3, 4, or 5; and the pyridine is substituted by 0 to 3 (e.g., 0, 1, 2, or 3) $R^{12}$ substituents, wherein each $R^{12}$ is independently a halogen (e.g., F, Cl), a $C_{6-10}$ aryl (e.g., phenyl), a heteroaryl, or a $C_{1-4}$ alkyl (e.g., methyl, ethyl, propyl, isopropyl, n-butyl, sec-butyl, iso-butyl, tert-butyl). In some embodiments, $R^{10}$ is selected from the group consisting of hexadecyl, eicosanyl and (2'-octyl)dodecyl; $R^{20}$ is hydrogen or methyl; q is 4; p is 2; and the pyridine is substituted by 0, 1, or 2 $R^{12}$ substituents, wherein each $R^{12}$ is independently a halogen (e.g., F, CO, a phenyl, or a methyl. In some embodiments, the pyridine is substituted by one $R^{11}$ substituent at the 2-, 3-, or 4-position of the pyridine, wherein $R^{11}$ is as defined herein, for example, a halogen (e.g., F, Cl), a phenyl, or a methyl. In some embodiments, the pyridine ring is substituted by one $R^{12}$ substituent, wherein the one $R^{12}$ substituent is fluorine or phenyl. In some embodiments, the pyridine ring is 3-fluoro-pyridine or 3-phenyl-pyridine.

In some embodiments, an oxidized lipid of the invention is a compound having a structure according to Formula 4:

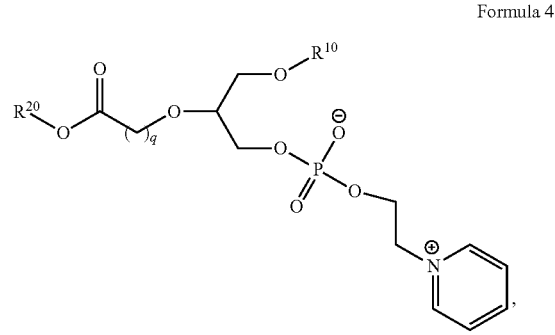

Formula 4 or a stereoisomer, a stereoisomeric mixture, or a salt thereof. Suitable $R^{10}$, $R^{20}$, and q are those as defined herein for Formula 1.

In some embodiments according to Formula 4, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl. In some embodiments, $R^{10}$ is hexadecyl. In some embodiments, $R^{10}$ is (2'-octyl)dodecyl. In some embodiments, $R^{10}$ is eicosanyl.

In some embodiments, $R^{20}$ is a hydrogen or an alkyl. In some embodiments, $R^{20}$ is hydrogen. In some embodiments, $R^{20}$ is an alkyl, e.g., a $C_{1-4}$ alkyl (e.g., methyl, ethyl, propyl, isopropyl, n-butyl, sec-butyl, iso-butyl, or tert-butyl). In some embodiments, $R^{20}$ is methyl.

In some embodiments, q is an integer of 1-10, e.g., 1, 2, 3, 4, 5, 6, 7, 8, 9, or 10. In some embodiments, q is 4.

In some embodiments, $R^{10}$ is selected from the group consisting of hexadecyl, eicosanyl and (2'-octyl)dodecyl; $R^{20}$ is hydrogen or a $C_{1-4}$ alkyl (e.g., methyl, ethyl, propyl, isopropyl, n-butyl, sec-butyl, iso-butyl, or tert-butyl); and q is an integer of 2-6, e.g., 2, 3, 4, 5, or 6. In some embodiments, $R^{10}$ is selected from the group consisting of hexadecyl, eicosanyl and (2'-octyl)dodecyl; $R^{20}$ is hydrogen; and q is an integer of 2-6, e.g., 2, 3, 4, 5, or 6. In some embodiments, $R^{10}$ is selected from the group consisting of hexadecyl, eicosanyl and (2'-octyl)dodecyl; $R^{20}$ is methyl; and q is an integer of 2-6, e.g., 2, 3, 4, 5, or 6.

In some embodiments, an oxidized lipid of the invention is a compound having a structure according to Formula 5:

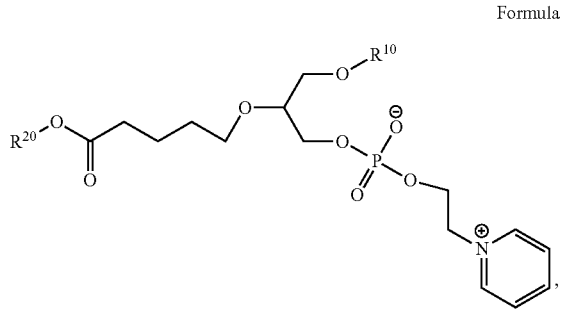

Formula 5 or a stereoisomer, a stereoisomeric mixture, or a salt thereof, wherein $R^{10}$ and $R^{20}$ are as defined herein for Formula 1.

In some embodiments according to Formula 5, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl. In some embodiments, $R^{10}$ is hexadecyl. In some embodiments, $R^{10}$ is (2'-octyl) dodecyl. In some embodiments, $R^{10}$ is eicosanyl.

In some embodiments, $R^{20}$ is a hydrogen or an alkyl. In some embodiments, $R^{20}$ is hydrogen. In some embodiments, $R^{20}$ is an alkyl, e.g., a $C_{1-4}$ alkyl (e.g., methyl, ethyl, propyl, isopropyl, n-butyl, sec-butyl, iso-butyl, or tert-butyl). In some embodiments, $R^{20}$ is methyl.

In some embodiments, an oxidized lipid of the invention is a compound having a structure of:

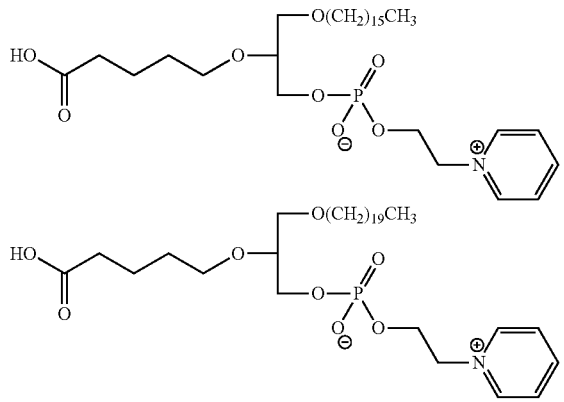

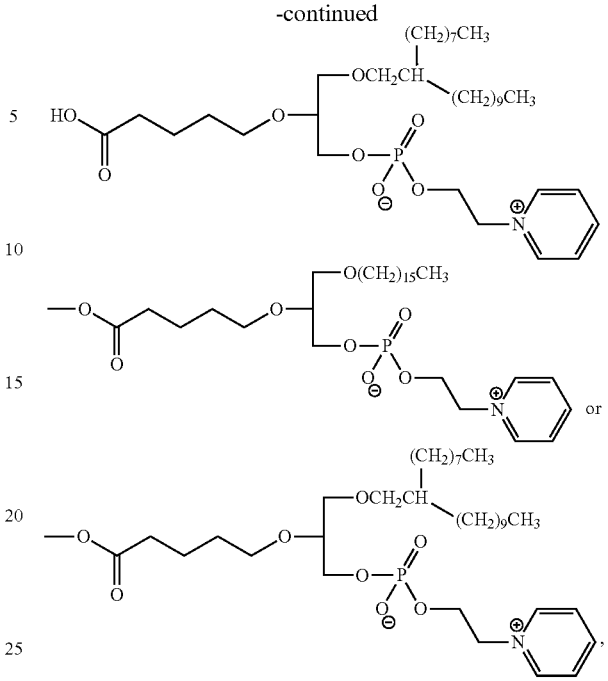

or a stereoisomer, a stereoisomeric mixture, or a salt thereof.

In some embodiments, the invention provides a compound selected from the group consisting of (R)-1-hexadecyl-2-(4'-carboxy)butyl-sn-glycero-3-phosphoric acid pyridiniumethyl ester (VB-701); (R)-1-eicosanyl-2-(4'-carboxy) butyl-sn-glycero-3-phosphoric acid pyridiniumethyl ester (VB-702); (R)-1-(2'-octyl)dodecyl-2-(4'-carboxy)butyl-sn-glycero-3-phosphoric acid pyridiniumethyl ester (VB-703); (R)-1-hexadecyl-2-(4'-carboxymethyl)butyl-sn-glycero-3-phosphoric acid pyridiniumethyl ester (VB-704); and (R)-1-(2'-octyl)dodecyl-2-(4'-carboxymethyl)butyl-sn-glycero-3-phosphoric acid pyridiniumethyl ester (VB-705). The prefix "(R)-" refers to the configuration of the C-2 carbon of the glycerol backbone.

In some embodiments, the invention provides an oxidized lipid having a structure of:

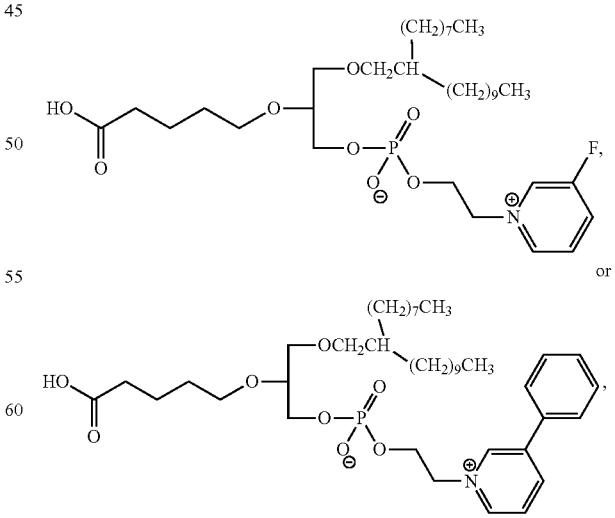

or a stereoisomer, a stereoisomeric mixture, or a salt thereof.

In some embodiments, the invention provides a compound selected from the group consisting of (R)-1-(2'-octyl)dodecyl-2-(4'-carboxy)butyl-glycero-sn-3-phosphoric acid 3-fluoro-pyridiniumethyl ester (VB-706) and (R)-1-(2'-octyl)dodecyl-2-(4'-carboxy)butyl-glycero-sn-3-phosphoric acid 3-phenyl-pyridiniumethyl ester (VB-707). The prefix "(R)-" refers to the configuration of the C-2 carbon of the glycerol backbone.

In still other embodiments, the present invention provides pharmaceutical compositions comprising an oxidized lipid of the invention, methods of making an oxidized lipid of the invention, and methods of preventing or treating fibrosis or an inflammatory disease or disorder with an oxidized lipid or composition of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

FIG. 1A shows the structures of the VB-701, VB-702, VB-703, VB-704 and VB-705 oxidized lipid compounds. FIG. 1B shows the structures of the VB-706 and VB-707 oxidized lipid compounds.

FIG. 2 shows VB-701 inhibits lipopolysaccharide (LPS) (TLR4)-induced signaling in human monocytes (primary CD14+).

FIG. 8 shows VB-702 inhibits chemokine-induced migration of human monocytes (primary CD14+).

FIGS. 9A-9B show VB-701 and VB-702 inhibit IL-12p40 levels in human monocytes (primary CD14+) that are LPS (TLR4)-stimulated (FIG. 9A) and Pam3CSK4 (TLR2)-stimulated (FIG. 9B).

FIGS. 10A-10B show the effect of VB-703 and VB-201 on LPS-induced signaling in human monocytes (primary CD14+) and LPS binding inhibition assay. Human primary monocytes were pretreated with VB-201 or VB-703 at the indicated concentrations followed by activation with LPS. Samples were analyzed by western blotting for inhibition of phosphorylation (FIG. 10A). Heat shock protein HSP90 was used for loading control. FIG. 10B shows results from samples incubated with VB-201 or VB-703 at the indicated concentrations for 20 minutes before biotin-LPS (100 ng/ml) was added for an additional 15 minutes. Results are the mean fluorescence intensity (MFI) of triplicates.

FIGS. 11A-11B show the effect of VB-703 on liver fibrosis. NASH was induced by injection of mice with 200 µg streptozotocin (STZ) two days after birth and by feeding a high fat diet (HFD) from 4 weeks of age. Mice were then either treated with vehicle (negative control), VB-703 (4 mg/kg), or telmisartan (10 mg/kg; positive control) at six weeks of age for three weeks. Normal mice (not NASH-induced) were also used as a control. Mice were sacrificed at nine weeks of age. Staining of liver histological samples with Sirius red was used to determine the extent of fibrosis. FIG. 11A shows the mean fibrosis area following treatment (% from analyzed liver section; Mean±S.E; Normal-n=5, Vehicle-n=8, Telmisartan-n=6). FIG. 11B shows representative Sirius red staining of liver samples following treatment (200× magnification).

FIGS. 12A-12B show the effect of VB-703 on liver inflammation. Mice were treated and evaluated as explained in the examples. FIG. 12A shows the mean liver inflammation score following treatment (Mean S.E; Normal-n=5, Vehicle-n=8, VB-703-n=8, Telmisartan-n=6). FIG. 12B shows representative H&E staining of liver samples following treatment (200× magnification).

FIG. 13 shows VB-703 inhibits PGN (TLR2)-induced signaling in human monocytes (THP-1 cell line).

FIG. 14 shows VB-703 inhibits IL-6 secretion in LPS (TLR4)-induced signaling in monocyte derived dendritic cells.

FIG. 15 shows VB-703 inhibits IL-12p40 secretion in LPS (TLR4)-induced signaling in monocyte derived dendritic cells.

FIG. 19 shows VB-703 and VB-705 inhibit LPS binding in human monocytes (primary CD14+).

FIG. 20 shows VB-705 does not inhibit SDF1-induced cell migration in human monocytes (THP-1 cell line).

FIG. 21A-21C present bar graphs showing the expression levels of two pro-inflammatory cytokines, IL-12/23p40 (FIG. 21A) and IL-1β (FIG. 21C), and the chemokine, MCP-1 (FIG. 21B), in livers taken from NASH-induced mice. These data show that the expression of IL-12/23p40, MCP-1, and IL-1β were significantly inhibited in livers taken from NASH-induced mice that were treated with VB-703.

FIGS. 26A-26C present bar graphs showing the effect of VB-703 on pro-fibrotic markers. Collagen IV (FIG. 26A), fibronectin (FIG. 26B) and TGF-β (FIG. 26C) related expression in the kidney were evaluated in healthy rats (white bar), sham operated rats (white bar with stripes), nephrectomized rats treated with solvent control (0.5% ethanol/PBS) (black bar), nephrectomized rats VB-703 4 mg/kg treated (light gray bar), or nephrectomized rats telmisartan 10 mg/kg treated (dark gray bar) at 8 weeks. Abbreviations are: Nx, nephrectomized; Eth, ethanol. The p-values in FIGS. 26A-26C represent statistically-significant differences from nephrectomized rats treated with PBS.

DETAILED DESCRIPTION OF THE INVENTION

Figure 3:
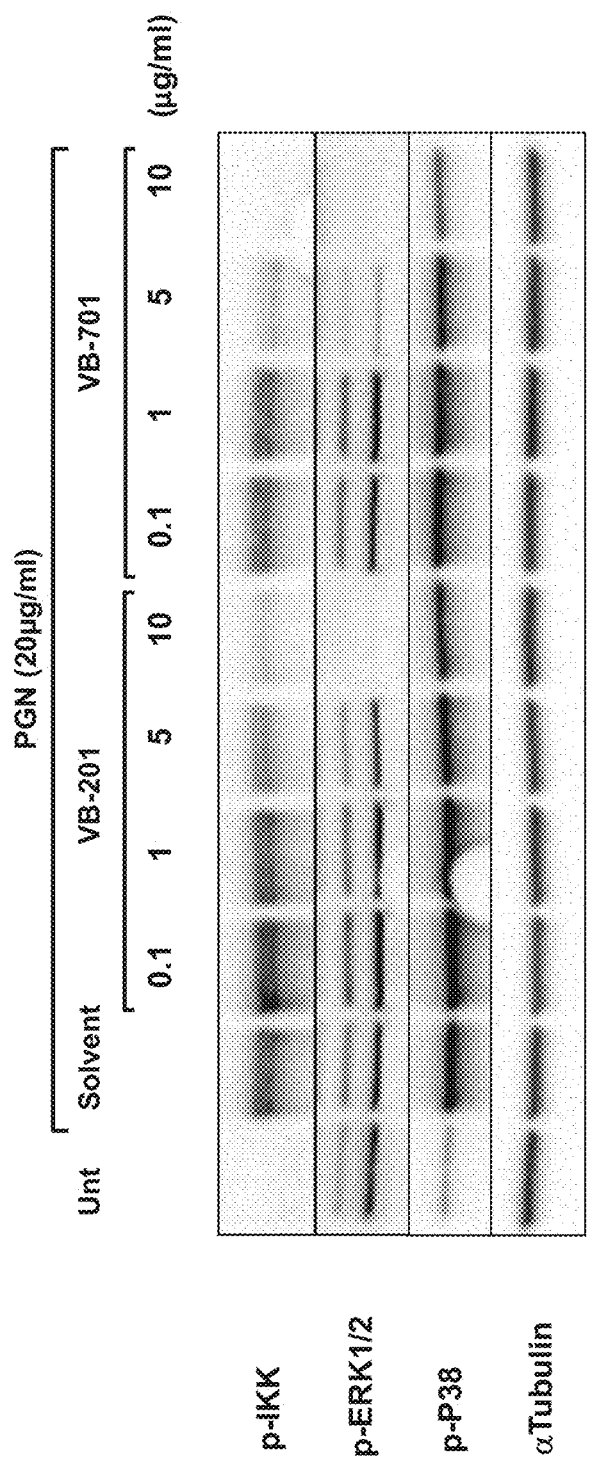
FIG. 3 shows VB-701 inhibits PGN (TLR2)-induced signaling in human monocytes (THP-1 cell line).

Before explaining embodiments of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

General Definitions

The terms "comprises", "comprising", "includes", "including", "having", and their conjugates mean "including but not limited to."

The word "optionally" is used herein to mean "is provided in some embodiments and not provided in other embodiments." Any particular embodiment of the invention can include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. Whether or not modified by the term "about", the claims include equivalents of the recited quantities. In one embodiment, the term "about" means within 10% of the reported numerical value.

The term "therapeutically effective amount," as used herein, refers to that amount of a given therapeutic agent sufficient to result in amelioration of one or more symptoms of a disorder or condition, or prevent appearance or advancement of a disorder or condition, or cause regression of or cure from the disorder or condition. In some embodiments, a therapeutically effective amount of the compound described herein is about 5 mg to about 160 mg of the compound per day.

As used herein throughout, the term "alkyl" refers to a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. In some embodiments, the alkyl is a lower alkyl having 1 to 4 carbon atoms. The alkyl group can be substituted (e.g., with 1 to 5 substituent groups) or unsubstituted. In any of the embodiments described herein, the alkyl can be unsubstituted. In any of the embodiments described herein, the alkyl can also be substituted by one to five substituent groups, wherein the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group can be substituted (e.g., with 1 to 5 substituent groups) or unsubstituted. In any of the embodiments described herein, the cycloalkyl can be unsubstituted. In any of the embodiments described herein, the cycloalkyl can also be substituted by one to five substituent groups, wherein the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an aliphatic hydrocarbon group which contains at least two carbon atoms and at least one carbon-carbon double bond, which can be straight or branched. An alkenyl group can be substituted or unsubstituted.

An "alkynyl" group refers to an aliphatic hydrocarbon group which contains at least two carbon atoms and at least one carbon-carbon triple bond. An alkynyl group can be substituted or unsubstituted.

An "aryl" group refers to an all-carbon monocyclic or fused-ring polycyclic (i.e., rings which share adjacent pairs of carbon atoms) groups having a completely conjugated pi-electron system. In any of the embodiments described herein, aryl groups can have 6 to 14 carbons, e.g., 6 to 10 carbons. Examples, without limitation, of aryl groups are phenyl, naphthalenyl and anthracenyl. The aryl group can be substituted (e.g., with 1 to 5 substituent groups) or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. In any of the embodiments described herein, the aryl group can be a phenyl group, optionally substituted, for example, by one to five substituent such as halogens (e.g., fluorine or chlorine), alkyl groups (e.g., a $C_{1-4}$ alkyl), or halogen substituted alkyls (e.g., trifluoromethyl).

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. In any of the embodiments described herein, heteroaryl groups can have 5 to 14 ring atoms, e.g., 5 to 10 ring atoms (e.g., 5 or 6 ring atoms). Examples, without limitation, of heteroaryl groups include pyrrole, furan, thiophene, imidazole, oxazole, thiazole, pyrazole, pyridine, pyrimidine, quinoline, isoquinoline and purine. The heteroaryl group can be substituted (e.g., with 1 to 5 substituent groups) or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more heteroatoms such as nitrogen, oxygen and sulfur. The rings may also have one or more double bonds. However, the rings do not have a completely conjugated pi-electron system. In any of the embodiments described herein, heteroalicyclic groups can have 3 to 10 ring atoms, e.g., 5 to 10 ring atoms (e.g., 5 or 6 ring atoms). The heteroalicyclic can be substituted (e.g., with 1 to 5 substituent groups) or unsubstituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

An "alkoxy" group refers to both an —O-alkyl and an —O-cycloalkyl group, wherein the alkyl or cycloalkyl can be any of those as defined herein.

An "aryloxy" group refers to both an —O-aryl and an —O-heteroaryl group, wherein the aryl or heteroaryl can be any of those as defined herein.

A "thiohydroxy" group refers to a —SH group.

A "thioalkoxy" group refers to both an —S-alkyl group, and an —S-cycloalkyl group, wherein the alkyl or cycloalkyl can be any of those as defined herein.

A "thioaryloxy" group refers to both an —S-aryl and an —S-heteroaryl group, wherein the aryl or heteroaryl can be any of those as defined herein.

A "carbonyl" group refers to a —C(=O)—R group, wherein R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, wherein R is hydrogen.

A "thiocarbonyl" group refers to a —C(=S)—R group, wherein R is as defined herein.

A "C-carboxy" group refers to a —C(=O)—O—R groups, wherein R is as defined herein.

An "O-carboxy" group refers to an RC(=O)—O— group, wherein R is as defined herein.

An "oxo" group refers to a =O group.

A "carboxylic acid" group refers to a C-carboxyl group in which R is hydrogen.

A "halo" group or "halogen" refers to fluorine, chlorine, bromine or iodine.

A "trihalomethyl" group refers to a —$CX_3$ group wherein X is a halo group as defined herein, e.g., a $CF_3$ group.

A "sulfinyl" group refers to an —S(=O)—R group, wherein R is as defined herein.

A "sulfonyl" group refers to an —$S(=O)_2$—R group, wherein R is as defined herein.

An "S-sulfonamido" group refers to a —$S(=O)_2$—$NR_2$ group, with each of R as is defined herein.

An "N-sulfonamido" group refers to an $RS(=O)_2$—NR group, wherein each of R is as defined herein.

An "O-carbamyl" group refers to an —OC(=O)—$NR_2$ group, wherein each of R is as defined herein.

An "N-carbamyl" group refers to an ROC(=O)—NR— group, wherein each of R is as defined herein.

An "O-thiocarbamyl" group refers to an —OC(=S)—$NR_2$ group, wherein each of R is as defined herein.

An "N-thiocarbamyl" group refers to an ROC(=S)NR— group, wherein each of R is as defined herein.

An "amino" group refers to an —$NR_2$ group wherein each of R is as defined herein.

A "C-amido" group refers to a —C(=O)—$NR_2$ group, wherein each of R is as defined herein.

An "N-amido" group refers to an RC(=O)—NR— group, wherein each of R is as defined herein.

An "urea" group refers to an —NRC(=O)—$NR_2$ group, wherein each of R is as defined herein.

A "guanidino" group refers to an —RNC(=N)—$NR_2$ group, wherein each of R is as defined herein.

A "guanyl" group refers to an $R_2NC(=N)$— group, wherein each of R is as defined herein.

The term "phosphonyl" or "phosphonate" describes a —P(=O)(OR)$_2$ group, with R as defined herein.

The term "phosphate" describes an —O—P(=O)(OR)$_2$ group, with each of R as defined herein.

A "phosphoric acid" is a phosphate group wherein each of R is hydrogen.

The term "phosphinyl" describes a —PR$_2$ group, with each of R as defined herein.

The term "thiourea" describes a —NR—C(=S)—NR— group, with each of R as defined herein.

The term "saccharide" refers to one or more sugar units, either an open-chain sugar unit or a cyclic sugar unit (e.g., pyranose- or furanose-based units), and encompasses any monosaccharide, disaccharide and oligosaccharide, unless otherwise indicated.

The term "stereoisomer" includes geometric isomers, such as E or Z isomers, enantiomers, diastereomers, and the like.

The term "stereoisomeric mixture" includes any mixture in any ratio of stereoisomers defined herein. In some embodiments, a stereoisomeric mixture includes a racemic mixture. In some embodiments, a stereoisomeric mixture includes an enantiomerically enriched mixture. In some embodiments, a stereoisomeric mixture includes a mixture of diastereomers in any ratio.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer.

The term "salt" includes both internal salt or external salt. In some embodiments, the salt is an internal salt, i.e., a zwitterion structure. In some embodiments, the salt is an external salt. In some embodiments, the external salt is a pharmaceutically acceptable salt having a suitable counter ion. Suitable counterions for pharmaceutical use are known in the art.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Oxidized Lipids

The present invention is directed, in part, to oxidized lipid compounds.

In some embodiments, an oxidized lipid of the invention is a compound according to Formula 1:

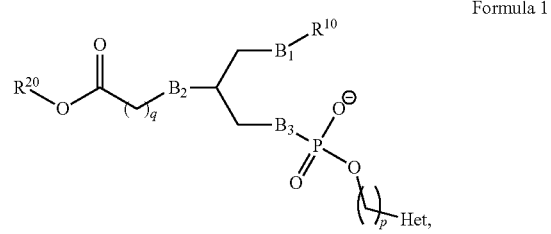

Formula 1 wherein each of $B_1$, $B_2$, and $B_3$ is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy and oxo;

wherein $R^{10}$ is a $C_{2-28}$ alkyl optionally substituted by one to five $R^{11}$ substituents, wherein each $R^{11}$ is independently selected from the group consisting of alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy, and amino;

wherein p is an integer selected from 1-10;

wherein q is an integer selected from 1-26;

wherein $R^{20}$ is selected from the group consisting of hydrogen, alkyl, alkenyl, alkynyl, cycloalkyl, aryl, and heteroaryl; and wherein Het is a heteroalicyclic ring or a heteroaryl. In other embodiments, the oxidized lipid is a compound according to Formula 1, or a stereoisomer, a stereoisomeric mixture, or a salt thereof. In some embodiments, the oxidized lipid having a structure according to Formula 1 has a zwittionic structure. In some embodiments, the oxidized lipid is an external salt (e.g., a pharmaceutically acceptable salt) of the compound having a structure according to Formula 1. In some embodiments, the compound according to Formula 1 has a structure according to Formula 1a or Formula 1b:

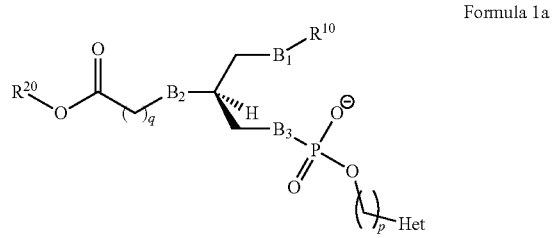

Formula 1a

-continued

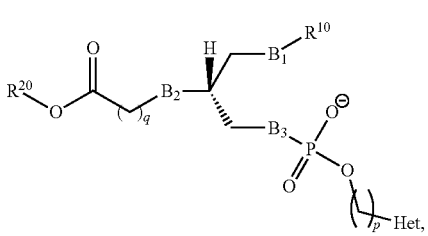

Formula 1b or a salt thereof.

In some embodiments, the compound has a structure according to Formula 1a, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In some embodiments, the compound has a structure according to Formula 1b, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

Suitable $B_1$, $B_2$, and $B_3$ for Formula 1 are defined herein. In some embodiments, $B_1$ is O. In some embodiments, $B_2$ is O. In some embodiments, $B_3$ is O. In some embodiments, at least two of $B_1$, $B_2$, and $B_3$ are O, e.g., $B_1$, $B_2$ are O and $B_3$ is O or S; $B_1$, $B_3$ are O and $B_2$ is O or S; or $B_2$, $B_3$ are O and $B_1$ is O or S. In some embodiments, $B_1$ is S. In some embodiments, $B_2$ is S. In some embodiments, $B_3$ is S. In some embodiments, at least two of $B_1$, $B_2$, and $B_3$ are S, e.g., $B_1$, $B_2$ are S and $B_3$ is O or S; $B_1$, $B_3$ are S and $B_2$ is O or S; or $B_2$, $B_3$ are S and $B_1$ is O or S. In some embodiments, all of $B_1$, $B_2$, and $B_3$ are O. In some embodiments, all of $B_1$, $B_2$, and $B_3$ are S.

Suitable $R^{10}$ for Formula 1 are defined herein. In some embodiments, $R^{10}$ is a $C_{2-28}$ alkyl. In some embodiments, $R^{10}$ is a straight chain $C_{2-28}$ alkyl, e.g., an alkyl chain having 4, 5, 6, 7, 8, 9, 10, 11, 12, 13, 14, 15, 16, 17, 18, 19, 20, 21, 22, 23, 24, 25, 26, 27, or 28 carbons, substituted or unsubstituted. In some embodiments, $R^{10}$ is a straight chain $C_{2-28}$ alkyl, e.g., an alkyl chain having 4, 5, 6, 7, 8, 9, 10, 11, 12, 13, 14, 15, 16, 17, 18, 19, 20, 21, 22, 23, 24, 25, 26, 27, or 28 carbons, substituted by one to five $R^{11}$ substituents, wherein each $R^{11}$ is independently as defined herein, e.g., a halogen (e.g., F) or an alkyl (e.g., a $C_{1-10}$ alkyl). In some embodiments, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl. In some embodiments, $R^{10}$ is hexadecyl. In some embodiments, $R^{10}$ is (2'-octyl)dodecyl. In some embodiments, $R^{10}$ is eicosanyl.

Suitable $R^{20}$ for Formula 1 are defined herein. In some embodiments, $R^{20}$ is a hydrogen or an alkyl. In some embodiments, $R^{20}$ is hydrogen. In some embodiments, $R^{20}$ is an alkyl, e.g., a $C_{1-4}$ alkyl (e.g., methyl, ethyl, propyl, isopropyl, n-butyl, sec-butyl, iso-butyl, or tert-butyl). In some embodiments, $R^{20}$ is methyl.

Suitable values for p and q in Formula 1 are defined herein. In some embodiments, q is an integer of 1-10, e.g., 1, 2, 3, 4, 5, 6, 7, 8, 9, or 10. In some embodiments, q is 4. In some embodiments, p is an integer of 1-7, e.g., 1, 2, 3, 4, 5, 6, or 7. In some embodiments, p is 2.

Suitable Het for Formula 1 are defined herein. In some embodiments, Het is a heteroaryl. In some embodiments, Het is a monocyclic heteroaryl. In some embodiments, Het is a nitrogen containing heteroaryl (e.g., monocyclic heteroaryl). In some embodiments, Het is a monocyclic heteroaryl containing 1, 2, 3, or 4 nitrogen atoms. In some embodiments, Het is a 6-member ring monocyclic heteroaryl, e.g., pyridine, pyrimidine, pyridazine, pyrazine, triazine, etc. In some embodiments, Het is a 5-member ring monocyclic heteroaryl, e.g., imidazole, thiazole, isothiazole, oxazole, isoxazole, oxidiazole, pyrazole, triazole, etc. In some embodiments, Het is a bicyclic heteroaryl containing nitrogen atoms, e.g., 1-3 nitrogen atoms, e.g., quinoline, isoquinoline, quinazoline, thienopyridine, thienopyrimidine, pyrrolopyridine, imidazopyridine, etc. In any of the embodiments described herein, Het can be a nitrogen containing heteroaryl, wherein a nitrogen atom of the heteroaryl is directly connected to the alkylene chain, i.e., —$(CH_2)_p$— in Formula 1 to form a cation. In some embodiments, Het is pyridine, wherein the nitrogen atom of the pyridine is directly connected to the alkylene chain, i.e., —$(CH_2)_p$— in Formula 1 form a pyridinium salt (e.g., an internal salt or an external salt as described herein). In some embodiments, Het is an unsubstituted pyridine, wherein the nitrogen atom of the pyridine is directly connected to the alkylene chain, i.e., —$(CH_2)_p$— in Formula 1. In some embodiments, Het is a substituted pyridine, wherein the nitrogen atom of the pyridine is directly connected to the alkylene chain, i.e., —$(CH_2)_p$— in Formula 1, wherein the pyridine is substituted by one to five (e.g., 1, 2, 3, 4, or 5) $R^{12}$ substituents, wherein each $R^{12}$ is independently selected from the group consisting of alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy, and amino as defined herein. In some embodiments, each $R^{12}$ is independently, e.g., a halogen (e.g., F, Cl), a $C_{6-10}$ aryl (e.g., phenyl), a heteroaryl, or an alkyl (e.g., a $C_{1-10}$ alkyl, e.g., a $C_{1-4}$ alkyl (e.g., methyl, ethyl, propyl, isopropyl, n-butyl, sec-butyl, iso-butyl, ten-butyl)). In some embodiments, Het is a substituted pyridine and the pyridine is substituted by one $R^{12}$ substituent at the 2-, 3-, or 4-position of the pyridine, wherein $R^{12}$ is as defined herein, for example, a halogen (e.g., F, Cl), a phenyl, or a methyl.

In some embodiments, an oxidized lipid of the invention is a compound having a structure according to Formula 2:

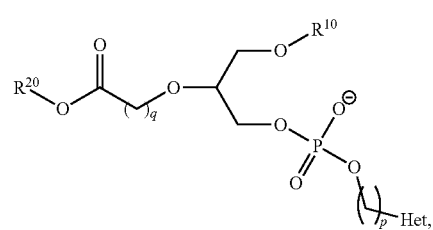

Formula 2 or a stereoisomer, a stereoisomeric mixture, or a salt thereof. Suitable $R^{10}$, $R^{20}$, p, q, and Het are those as defined herein for Formula 1. In some embodiments, the oxidized lipid having a structure according to Formula 2 has a zwittionic structure. In some embodiments, the oxidized lipid is an external salt (e.g., a pharmaceutically acceptable salt) of the compound having a structure according to Formula 2. In some embodiments, the compound according to Formula 2 has a structure according to Formula 2a or Formula 2b:

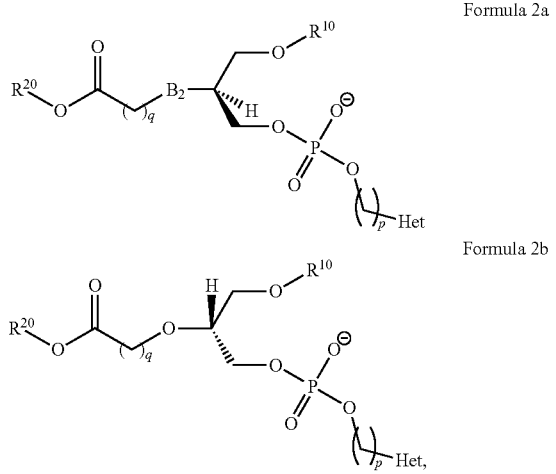

Formula 2a

Formula 2b or a salt thereof.

In some embodiments, the compound is a S-isomer having a structure according to Formula 2a, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In some embodiments, the compound is a R-isomer having a structure according to Formula 2b, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In some embodiments according to Formula 2, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl; $R^{20}$ is hydrogen or an alkyl, e.g., a $C_{1-4}$ alkyl (e.g., methyl, ethyl, propyl, isopropyl, n-butyl, sec-butyl, iso-butyl, or tert-butyl); q is an integer of 1-10, e.g., 1, 2, 3, 4, 5, 6, 7, 8, 9, or 10; p is an integer of 1-7, e.g., 1, 2, 3, 4, 5, 6, or 7; and Het is an unsubstituted pyridine, wherein the nitrogen atom of the pyridine is directly connected to the alkylene chain, i.e., —(CH$_2$)$_p$— in Formula 2, or Het is a substituted pyridine, wherein the nitrogen atom of the pyridine is directly connected to the alkylene chain, i.e., —(CH$_2$)$_p$— in Formula 2, wherein the pyridine is substituted by one to five (e.g., 1, 2, 3, 4, or 5) $R^{12}$ substituents, wherein each $R^{12}$ is independently as defined herein, e.g., a halogen (e.g., F, CO, a $C_{6-10}$ aryl (e.g., phenyl), a heteroaryl, or an alkyl (e.g., a $C_{1-10}$ alkyl, e.g., a $C_{1-4}$ alkyl (e.g., methyl, ethyl, propyl, isopropyl, n-butyl, sec-butyl, iso-butyl, tert-butyl). In some embodiments, Het is a substituted pyridine and the pyridine is substituted by one $R^{12}$ substituent at the 2-, 3-, or 4-position of the pyridine, wherein $R^{12}$ is as defined herein, for example, a halogen (e.g., F, Cl), a phenyl, or a methyl.

In some embodiments, an oxidized lipid of the invention is a compound having a structure according to Formula 3:

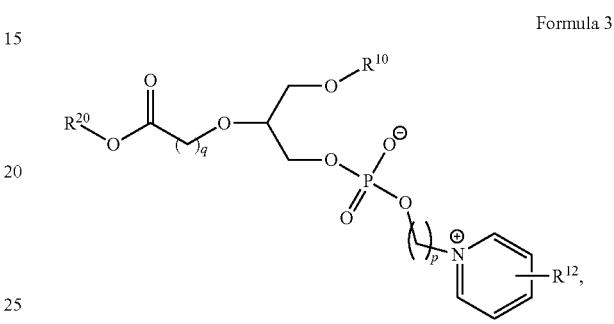

Formula 3 or a stereoisomer, a stereoisomeric mixture, or a salt thereof, wherein $R^{10}$, $R^{12}$, $R^{20}$, p, and q are as defined herein for Formula 1. In some embodiments, the oxidized lipid is a zwittionic structure according to Formula 3. In some embodiments, the oxidized lipid is an external salt (e.g., a pharmaceutically acceptable salt) of the compound having a structure according to Formula 3. In some embodiments, the oxidized lipid according to Formula 3 has a structure according to Formula 3a or Formula 3b:

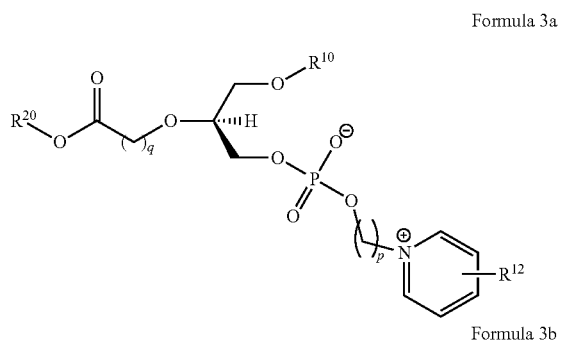

Formula 3a

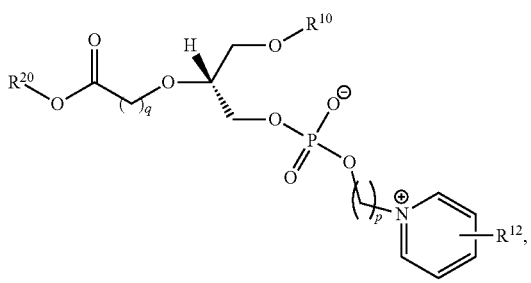

Formula 3b or a salt thereof.

In some embodiments, the compound is a S-isomer having a structure according to Formula 3a, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In some embodiments, the compound is a R-isomer having a structure according to Formula 3b, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In some embodiments according to Formula 3, $R^{10}$ is selected from the group consisting of hexadecyl, eicosanyl and (2'-octyl)dodecyl; $R^{20}$ is hydrogen or a $C_{1-4}$ alkyl (e.g., methyl, ethyl, propyl, isopropyl, n-butyl, sec-butyl, iso-butyl, or tert-butyl); q is an integer of 2-6, e.g., 2, 3, 4, 5, or 6; p is an integer of 2-5, e.g., 2, 3, 4, or 5; and the pyridine is substituted by 0 to 3 (e.g., 0, 1, 2, or 3) $R^{12}$ substituents, wherein each $R^{12}$ is independently as defined herein, e.g., a halogen (e.g., F, Cl), a $C_{6-10}$ aryl (e.g., phenyl), a heteroaryl, or a $C_{1-4}$ alkyl (e.g., methyl, ethyl, propyl, isopropyl, n-butyl, sec-butyl, iso-butyl, tert-butyl). In some embodiments, $R^{10}$ is selected from the group consisting of hexadecyl, eicosanyl and (2'-octyl)dodecyl; $R^{20}$ is hydrogen or methyl; q is 2, 3, 4, 5, or 6; p is 2, 3, 4, or 5; and the pyridine is substituted by 0 to 3 (e.g., 0, 1, 2, or 3) $R^{12}$ substituents, wherein each $R^{12}$ is independently is a halogen (e.g., F, Cl), a $C_{6-10}$ aryl (e.g., phenyl), a heteroaryl, or a $C_{1-4}$ alkyl (e.g., methyl, ethyl, propyl, isopropyl, n-butyl, sec-butyl, iso-butyl, ten-butyl). In some embodiments, $R^{10}$ is selected from the group consisting of hexadecyl, eicosanyl and (2'-octyl)dodecyl; $R^{20}$ is hydrogen or methyl; q is 4; p is 2; and the pyridine is substituted by 0, 1, or 2 $R^{12}$ substituents, wherein each $R^{12}$ is independently a halogen (e.g., F, Cl), a phenyl, or a methyl. In some embodiments according to Formulae 3, 3a, and 3b, $R^{10}$ is selected from the group consisting of hexadecyl, eicosanyl, and (2'-octyl)dodecyl. In some embodiments according to Formulae 3, 3a, and 3b, $R^{20}$ is a hydrogen or a $C_{1-4}$ alkyl. In some embodiments according to Formulae 3, 3a, and 3b, q is an integer of 2-6. In some embodiments according to Formulae 3, 3a, and 3b, p is an integer of 2-5. In some embodiments according to Formulae 3, 3a, and 3b, the pyridine is substituted by 0 to 3 (e.g., 0, 1, 2, or 3) $R^{12}$ substituents, wherein each $R^{12}$ is independently as defined herein, e.g., a halogen (e.g., F, Cl), a $C_{6-10}$ aryl (e.g., phenyl), a heteroaryl, or a $C_{1-4}$ alkyl (e.g., methyl, ethyl, propyl, isopropyl, n-butyl, sec-butyl, iso-butyl, tert-butyl). In some embodiments according to Formulae 3, 3a, and 3b, the pyridine ring is substituted by one, two, or three $R^{12}$ Substituents. In some embodiments according to Formulae 3, 3a, and 3b, the pyridine ring is substituted by one $R^{12}$ substituent, wherein the one $R^{12}$ substituent is a fluorine or a phenyl, e.g., the pyridine ring is 3-fluoro-pyridine or 3-phenyl-pyridine. In some embodiments according to Formulae 3, 3a, and 3b, $R^{10}$ is selected from the group consisting of hexadecyl, eicosanyl and (2'-octyl)dodecyl; $R^{20}$ is hydrogen or methyl; q is 4; p is 2; and the pyridine is 3-fluoro-pyridine or 3-phenyl-pyridine.

In some embodiments, an oxidized lipid of the invention is a compound having a structure according to Formula 4:

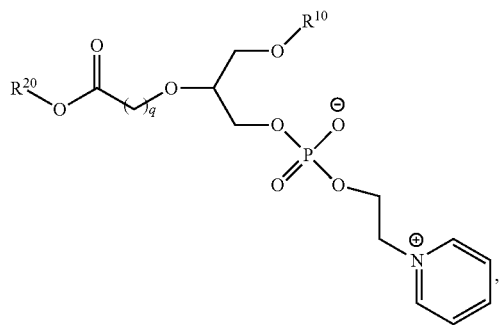

Formula 4 or a stereoisomer, a stereoisomeric mixture, or a salt thereof. Suitable $R^{10}$, $R^{20}$, and q are those as defined herein for Formula 1. In some embodiments, the oxidized lipid has a zwittionic structure according to Formula 4. In some embodiments, the oxidized lipid is an external salt (e.g., a pharmaceutically acceptable salt) of the compound having a structure according to Formula 4. In some embodiments, the oxidized lipid according to Formula 4 has a structure according to Formula 4a or Formula 4b:

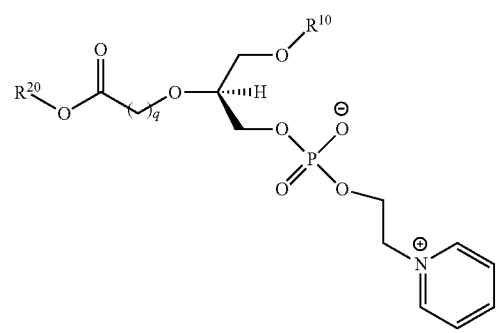

Formula 4a

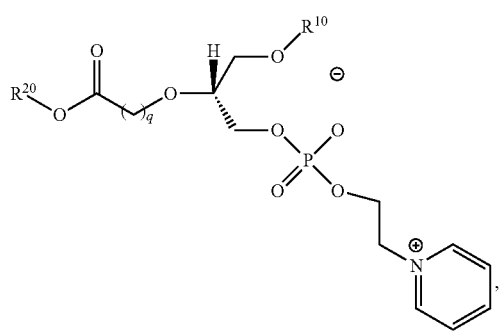

Formula 4b or a salt thereof.

In some embodiments, the compound is a S-isomer having a structure according to Formula 4a, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In some embodiments, the compound is a R-isomer having a structure according to Formula 4b, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about $0% ee to about 99.5% ee, about 85% ee to about 99.5% ee, about 90% ee to about 99.5% ee, about 95% ee to about 99.5%, or any range thereof.

In some embodiments according to Formula 4, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl. In some embodiments, le is hexadecyl. In some embodiments, $R^{10}$ is (2'-octyl)dodecyl. In some embodiments, $R^{10}$ is eicosanyl.

In some embodiments, $R^{20}$ is a hydrogen or an alkyl. In some embodiments, $R^{20}$ is hydrogen. In some embodiments, $R^{20}$ is an alkyl, e.g., a $C_{1-4}$ alkyl (e.g., methyl, ethyl, propyl, isopropyl, n-butyl, sec-butyl, iso-butyl, or tert-butyl). In some embodiments, $R^{20}$ is methyl.

In some embodiments, q is an integer of 1-10, e.g., 1, 2, 3, 4, 5, 6, 7, 8, 9, or 10. In some embodiments, q is 4.

In some embodiments, $R^{10}$ is selected from the group consisting of hexadecyl, eicosanyl, and (2'-octyl)dodecyl; $R^{20}$ is hydrogen or a $C_{1-4}$ alkyl (e.g., methyl, ethyl, propyl, isopropyl, n-butyl, sec-butyl, iso-butyl, or tert-butyl); and q is an integer of 2-6, e.g., 2, 3, 4, 5, or 6. In some embodiments, $R^{10}$ is selected from the group consisting of hexadecyl, eicosanyl and (2'-octyl)dodecyl; $R^{20}$ is hydrogen; and q is an integer of 2-6, e.g., 2, 3, 4, 5, or 6. In some embodiments, $R^{10}$ is selected from the group consisting of hexadecyl, eicosanyl, and (2'-octyl)dodecyl; $R^{20}$ is methyl; and q is an integer of 2-6, e.g., 2, 3, 4, 5, or 6.

In some embodiments, an oxidized lipid of the invention is a compound having a structure according to Formula 5,

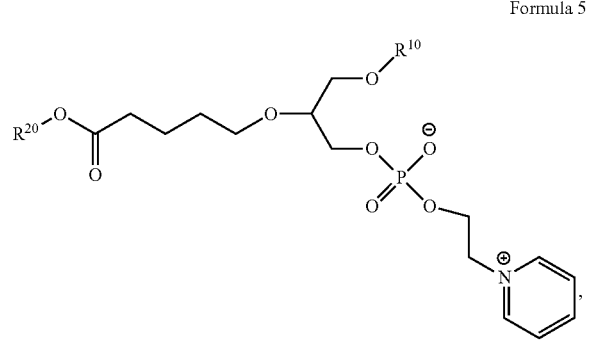

Formula 5 or a stereoisomer, a stereoisomeric mixture, or a salt thereof, wherein $R^{10}$ and $R^{20}$ are as defined herein for Formula 1. In some embodiments, the oxidized lipid has a zwittionic structure according to Formula 5. In some embodiments, the oxidized lipid is an external salt (e.g., a pharmaceutically acceptable salt) of the compound having a structure according to Formula 5. In some embodiments, the oxidized lipid is a compound according to Formula 5 has a structure according to Formula 5a or Formula 5b:

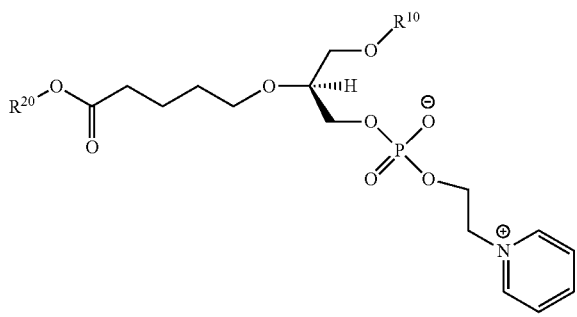

Formula 5a

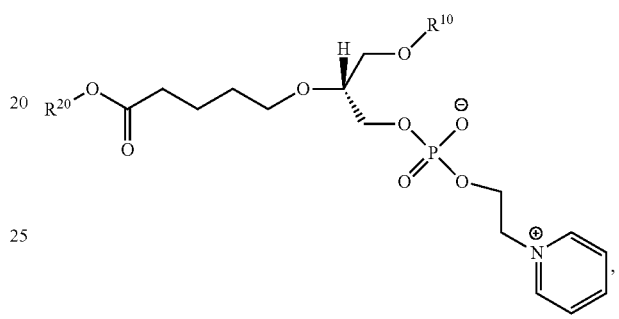

Formula 5b or a salt thereof.

In some embodiments, the compound is a S-isomer having a structure according to Formula 5a, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In some embodiments, the compound is a R-isomer having a structure according to Formula 5b, wherein the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In some embodiments according to Formula 5, $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl. In some embodiments, le is hexadecyl. In some embodiments, $R^{10}$ is (2'-octyl)dodecyl. In some embodiments, $R^{10}$ is eicosanyl.

In some embodiments, $R^{20}$ is a hydrogen or an alkyl. In some embodiments, $R^{20}$ is hydrogen. In some embodiments, $R^{20}$ is an alkyl, e.g., a $C_{1-4}$ alkyl (e.g., methyl, ethyl, propyl, isopropyl, n-butyl, sec-butyl, iso-butyl, or tert-butyl). In some embodiments, $R^{20}$ is methyl.

In some embodiments, an oxidized lipid of the invention is a compound having a structure of:

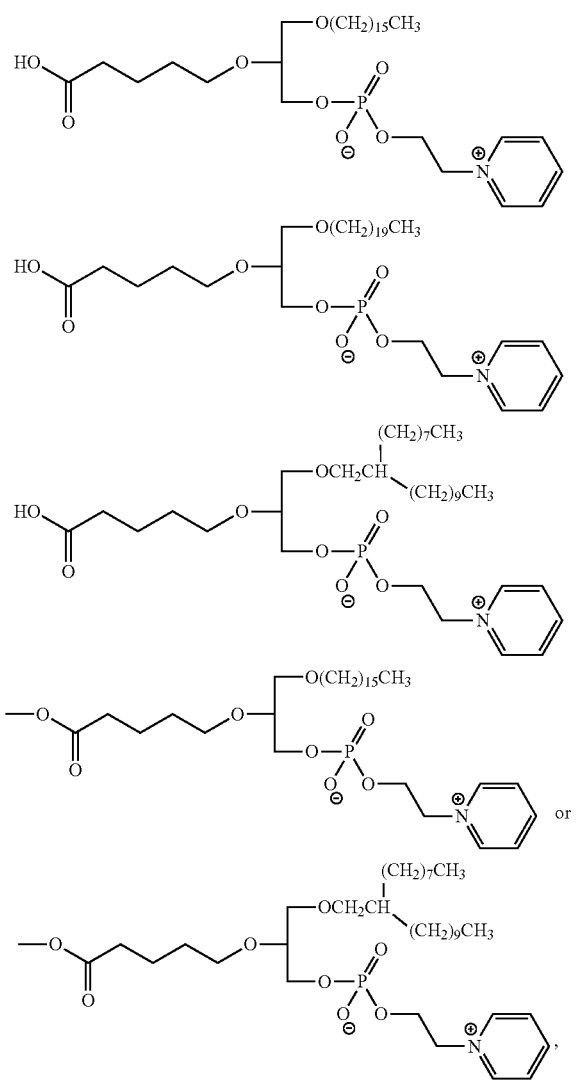

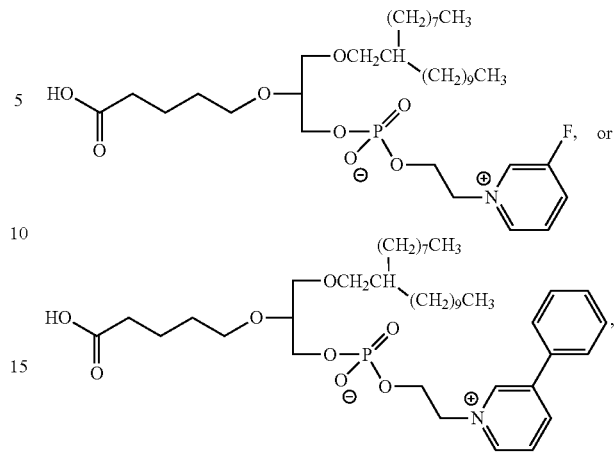

or a stereoisomer, a stereoisomeric mixture, or a salt thereof.

In some embodiments, the invention provides a compound selected from the group consisting of (R)-1-hexadecyl-2-(4'-carboxy)butyl-sn-glycero-3-phosphoric acid pyridiniumethyl ester (VB-701); (R)-1-eicosanyl-2-(4'-carboxy) butyl-sn-glycero-3-phosphoric acid pyridiniumethyl ester (VB-702); (R)-1-(2'-octyl)dodecyl-2-(4'-carboxy)butyl-sn-glycero-3-phosphoric acid pyridiniumethyl ester (VB-703); (R)-1-hexadecyl-2-(4'-carboxymethyl)butyl-sn-glycero-3-phosphoric acid pyridiniumethyl ester (VB-704); and (R)-1-(2'-octyl)dodecyl-2-(4'-carboxymethyl)butyl-sn-glycero-3-phosphoric acid pyridiniumethyl ester (VB-705). The prefix "(R)-" refers to the configuration of the C-2 carbon of the glycerol backbone. In some embodiments, the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more.

In some embodiments, an oxidized lipid of the invention is a compound having a structure of:

or a stereoisomer, a stereoisomeric mixture, or a salt thereof.

In some embodiments, the invention provides a compound selected from the group consisting of (R)-1-(2'-octyl) dodecyl-2-(4'-carboxy)butyl-glycero-sn-3-phosphoric acid 3-fluoro-pyridiniumethyl ester (VB-706) and (R)-1-(2'-octyl)dodecyl-2-(4'-carboxy)butyl-glycero-sn-3-phosphoric acid 3-phenyl-pyridiniumethyl ester (VB-707). The prefix "(R)-" refers to the configuration of the C-2 carbon of the glycerol backbone. In some embodiments, the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In other embodiments, an oxidized lipid compound of the invention treats or prevents fibrosis (e.g., liver fibrosis, kidney fibrosis, focal and segmental glomerulosclerosis, or any other fibrosis described herein) as well as, or better than, telmisartan. In other embodiments, an oxidized lipid compound of the invention reduces liver inflammation as well as, or better than, telmisartan. In other embodiments, an oxidized lipid compound of the invention reduces liver fibrosis as well as, or better than, telmisartan. In other embodiments, an oxidized lipid compound of the invention treats or prevents kidney fibrosis as well as, or better than, telmisartan. In other embodiments, an oxidized lipid compound of the invention treats or prevents focal and segmental glomerulosclerosis as well as, or better than, telmisartan.

In other embodiments, an oxidized lipid compound of the invention inhibits formation of ligand-induced phosphorylation of IKK, ERK, AKT, or p38 comparable to or more than VB-201 (1-hexadecyl-2-(4'-carboxy)butyl-glycero-3-phosphocholine or 1-hexadecyl-2-(4'-carboxybutyl)-glycerol-3-phosphocholine)) inhibits formation of ligand-induced phosphorylation of IKK, ERK, AKT, or p38. In other embodiments, an oxidized lipid compound of the invention inhibits ligand-induced cell migration comparable to or more than VB-201 inhibits ligand-induced cell migration. In other embodiments, the ligand is LPS, PGN, PAM3, or MCP1. In other embodiments, the cell migration is monocyte migration.

Methods of Synthesis

Other embodiments of the invention relate to methods of synthesizing oxidized lipids of the invention.

In some embodiments, the invention provides a method of synthesizing a compound of Formula 1,

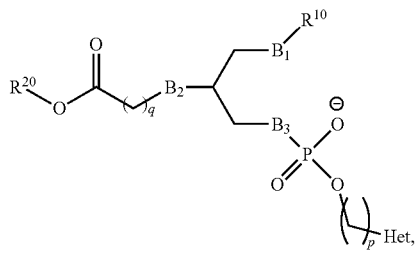

Formula 1 or a stereoisomer, a stereoisomeric mixture, or a salt thereof, wherein $B_1$, $B_2$, $B_3$, $R^{10}$, $R^{20}$, Het, p, and q are defined herein above for Formula 1, the method comprising a) reacting Intermediate 1

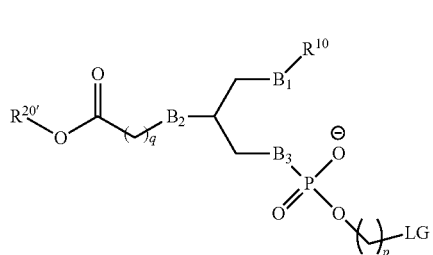

Intermediate 1 with Het to form the compound of Formula 1, wherein $B_1$, $B_2$, $B_3$, $R^{10}$, Het, p, and q are as defined above in Formula 1; and wherein LG is a leaving group. In some embodiments, $R^{20'}$ is the same as $R^{20}$. However, as described in the Examples section, when Intermediate 1 was heated in pyridine (e.g., at reflux temperature), conversion of —COOR$^{20'}$ into —COOH was also observed. Thus, in some embodiments, $R^{20}$ is H, $R^{20'}$ is selected from the group consisting of alkyl, alkenyl, alkynyl, cycloalkyl, aryl, and heteroaryl, the reacting of Intermediate 1 with Het (e.g., pyridine or substituted pyridine as defined herein) also converts —COOR$^{20'}$ into —COOH, or a salt thereof, to form the compound of Formula 1. In other embodiments, $R^{20}$ is H, $R^{20'}$ is selected from the group consisting of alkyl, alkenyl, alkynyl, cycloalkyl, aryl, and heteroaryl, the reacting of Intermediate 1 with Het is followed by a step of hydrolysis to convert —COOR$^{20'}$ into —COOH, or a salt thereof, to form the compound of Formula 1. In preferred embodiments, $R^{20}$ is H, $R^{20'}$ is methyl, the reacting of Intermediate 1 with Het (e.g., pyridine or substituted pyridine as defined herein) also converts —COOR$^{20'}$ into —COOH, or a salt thereof, to form the compound of Formula 1. In some embodiments, the LG is selected from the group consisting of halogen and oxygen containing leaving groups (e.g., as described herein).

In some embodiments, the Intermediate 1 can be synthesized by b) reacting Reactant 1

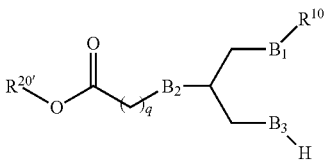

Reactant 1 with Reactant 2

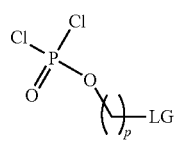

Reactant 2 to form a monochloro reaction product; and c) hydrolyzing the monochloro reaction product to form Intermediate 1, wherein $B_1$, $B_2$, $B_3$, $R^{10}$, $R^{20'}$, p, q, and LG are as defined above in Intermediate 1.

In other embodiments, the Intermediate 1 can be synthesized by b') reacting Reactant 1

Reactant 1 with POCl$_3$ to form a POCl$_3$ reaction product;

c') reacting Reactant 2A

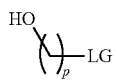

Reactant 2A with the POCl$_3$ reaction product to form a second reaction product; and d') hydrolyzing the second reaction product to form Intermediate 1, wherein $B_1$, $B_2$, $B_3$, $R^{10}$, $R^{20'}$, p, q, and LG are as defined above in Intermediate 1. In some embodiments, steps b') and c') can be performed in a one-pot fashion. In some embodiments, the POCl$_3$ reaction product is not isolated before reacting with Reactant 2A.

Suitable LGs for the methods of synthesis described herein include any leaving group known in the art. In some embodiments, LG is a halogen, such as F, Cl, Br, or I. In some embodiments, LG is an oxygen containing leaving group, such as a tosylate, a mesylate, a triflate, etc. In some embodiments, LG is Br. Oxygen containing leaving groups as used herein refer to leaving groups represented by formula

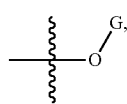

wherein G is typically an electron withdrawing group, e.g.,

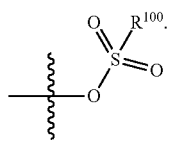

Examples of oxygen containing leaving groups include sulfonates such as nonaflate, triflate, fluorosulfonate, tosylate, mesylate or besylate. Other oxygen containing leaving groups such as acyloxy and aryloxy groups are known in the art.

In some embodiments, the LG is a leaving group selected from the group consisting of oxygen containing leaving groups represented by

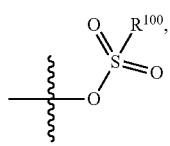

wherein $R^{100}$ is selected from the group consisting of alkyl, alkenyl, alkynyl, cycloalkyl, heteroalicycloalkyl, aryl, and heteroaryl, each of which is optionally substituted by one to five $R^{13}$, wherein each $R^{13}$ substituent is independently selected from the group consisting of alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy, and amino. In some embodiments, $R^{100}$ is p-tolyl, o-tolyl, phenyl, methyl, or trifluoromethyl. In some embodiments, $R^{100}$ is p-tolyl.

In some embodiments, all of $B_1$, $B_2$, and $B_3$ are O. In some embodiments, Het is an unsubstituted pyridine, wherein the nitrogen atom of the pyridine is directly connected to the alkylene chain, i.e., —$(CH_2)_p$— in Formula 1. In some embodiments, Het is 3-fluoro-pyridine or 3-phenyl-pyridine, wherein the nitrogen atom of the pyridine is directly connected to the alkylene chain, i.e., —$(CH_2)_p$— in Formula 1. In some embodiments, $R^{10}$ is selected from the group consisting of hexadecyl, eicosanyl and (2'-octyl) dodecyl. In some embodiments, $R^{20}$ is hydrogen or a $C_{1-4}$ alkyl (e.g., methyl, ethyl, propyl, isopropyl, n-butyl, sec-butyl, iso-butyl, or tert-butyl). In some embodiments, p is 2. In some embodiments, q is 4.

In some embodiments, the method described above is directed to synthesizing compounds having a structure according to Formulae 2, 3, 4, or 5 (e.g., as described herein). In such embodiments, all of $B_1$, $B_2$, and $B_3$ are O, and suitable $R^{10}$, $R^{11}$, $R^{12}$, $R^{20}$, Het, p, and q for the methods described above are those as defined herein for the respective Formulae 2, 3, 4, or 5. In some embodiments, $R^{20'}$ is the same as $R^{20}$. In some embodiments, $R^{20}$ is H, $R^{20'}$ is selected from the group consisting of alkyl, alkenyl, alkynyl, cycloalkyl, aryl, and heteroaryl, the reacting of Intermediate 1 with Het (e.g., pyridine or substituted pyridine as defined herein) also converts —$COOR^{20'}$ into —COOH, or a salt thereof, to form the compound of Formulae 2, 3, 4, or 5. In other embodiments, $R^{20}$ is H, $R^{20'}$ is selected from the group consisting of alkyl, alkenyl, alkynyl, cycloalkyl, aryl, and heteroaryl, the reacting of Intermediate 1 with Het is followed by a step of hydrolysis to convert —$COOR^{20'}$ into —COOH, or a salt thereof, to form the compound of Formulae 2, 3, 4, or 5. In preferred embodiments, $R^{20}$ is H in Formulae 2, 3, 4, or 5, $R^{20'}$ is methyl, the reacting of Intermediate 1 with Het (e.g., pyridine or substituted pyridine as defined herein) also converts —$COOR^{20'}$ into —COOH, or a salt thereof, to form the compound of Formulae 2, 3, 4, or 5.

Suitable solvents, reaction temperatures, as well as other reaction parameters for each of the process steps described herein can be ascertained by those skilled in the art based on the working Examples described herein.

Thus, in some embodiments, a compound having a structure according to Formula 1 (e.g., as described herein) can be synthesized by a method comprising the steps in Method A:

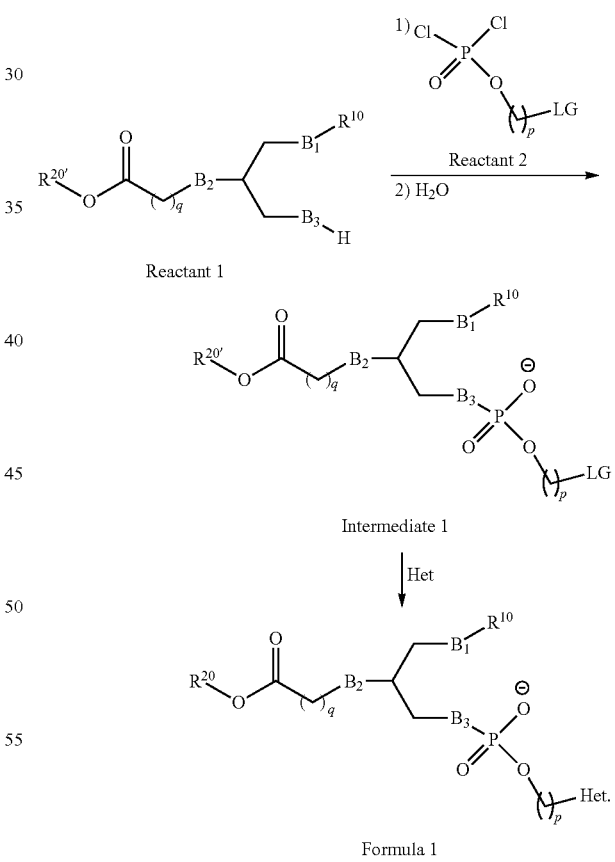

Suitable LGs include any leaving group known in the art. In some embodiments, LG is a halogen, such as F, Cl, Br, or I. In some embodiments, LG is an oxygen containing leaving group, such as a tosylate, a mesylate, a triflate, etc. In some embodiments, LG is Br. In some embodiments, LG is tosylate.

In some embodiments, a compound having a structure according to Formula 1 can also be synthesized by a method comprising the steps in Method B:

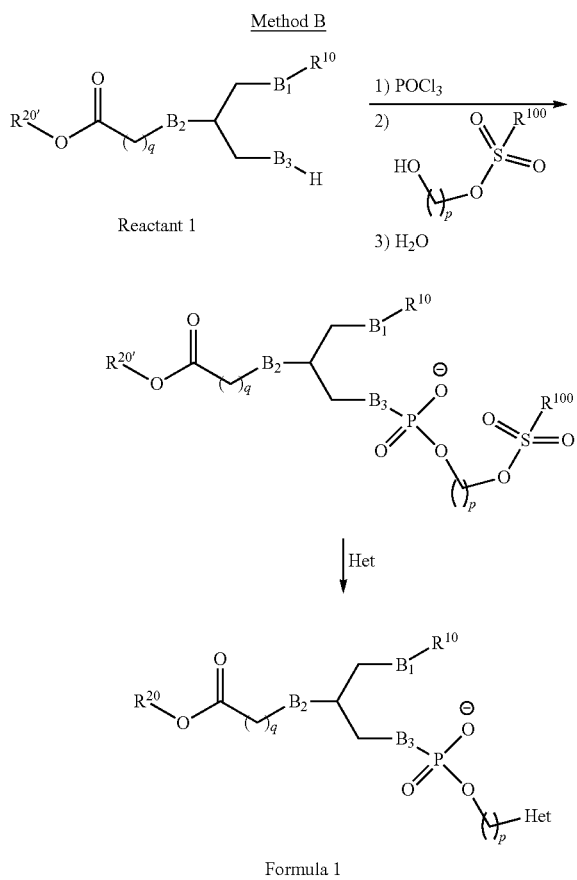

Suitable $R^{100}$ for Method B include alkyl, alkenyl, alkynyl, cycloalkyl, heteroalicycloalkyl, aryl, or heteroaryl, optionally substituted by one to five $R^{13}$, wherein each $R^{13}$ substituent is independently selected from the group consisting of alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy, and amino as described herein. In some embodiments, $R^{100}$ is a p-tolyl, o-tolyl, phenyl, methyl, or trifluoromethyl moiety. In some embodiments, $R^{100}$ is p-tolyl.

In some embodiments, the method for synthesizing a compound having a structure according to Formula 1 further comprises a step of hydrolysis to convert an ester into a carboxylic acid.

Suitable $B_1$, $B_2$, $B_3$, $R^{10}$, $R^{11}$, $R^{12}$, $R^{20}$, Het, p, and q for Method A or B are those as defined herein for Formula 1. In some embodiments, all of $B_1$, $B_2$, and $B_3$ are O. In some embodiments, Het is an unsubstituted pyridine, wherein the nitrogen atom of the pyridine is directly connected to the alkylene chain, i.e., —$(CH_2)_p$— in Formula 1. In some embodiments, $R^{10}$ is selected from the group consisting of hexadecyl, eicosanyl and (2'-octyl)dodecyl. In some embodiments, $R^{20}$ is hydrogen or a $C_{1-4}$ alkyl (e.g., methyl, ethyl, propyl, isopropyl, n-butyl, sec-butyl, iso-butyl, or tert-butyl). In some embodiments, p is 2. In some embodiments, q is 4. In some embodiments, $R^{20'}$ is the same as $R^{20}$. In some embodiments, $R^{20}$ is H, $R^{20'}$ is selected from the group consisting of alkyl, alkenyl, alkynyl, cycloalkyl, aryl, and heteroaryl, the reacting of Intermediate 1 with Het (e.g., pyridine or substituted pyridine as defined herein) also converts —$COOR^{20'}$ into —COOH, or a salt thereof, to form the compound of Formula 1. In other embodiments, $R^{20}$ is H, $R^{20'}$ is selected from the group consisting of alkyl, alkenyl, alkynyl, cycloalkyl, aryl, and heteroaryl, the reacting of Intermediate 1 with Het is followed by a step of hydrolysis to convert —$COOR^{20'}$ into —COOH, or a salt thereof, to form the compound of Formula 1. In preferred embodiments, $R^{20}$ is H, $R^{20'}$ is methyl, the reacting of Intermediate 1 with Het (e.g., pyridine or substituted pyridine as defined herein) also converts —$COOR^{20'}$ into —COOH, or a salt thereof, to form the compound of Formula 1.

Similarly, compounds having a structure according to Formulae 2, 3, 4, or 5 (e.g., as described herein) can be synthesized by any of the methods described above, e.g., by a method comprising the steps in Method A or the steps in Method B. In the synthesis of compounds having a structure according to Formulae 2, 3, 4, or 5 (e.g., as described herein), all of $B_1$, $B_2$, and $B_3$ are O, and suitable $R^{10}$, $R^{11}$, $R^{12}$, $R^{20}$, Het, p, p t and q for Method A or B are those as defined herein for the respective Formulae 2, 3, 4, or 5. In some embodiments, $R^{20'}$ is the same as $R^{20}$. In some embodiments, $R^{20}$ is H, $R^{20'}$ is selected from the group consisting of alkyl, alkenyl, alkynyl, cycloalkyl, aryl, and heteroaryl, the reacting of Intermediate 1 with Het (e.g., pyridine or substituted pyridine as defined herein) also converts —$COOR^{20'}$ into —COOH, or a salt thereof, to form the compound of Formulae 2, 3, 4, or 5. In other embodiments, $R^{20}$ is H, $R^{20'}$ is selected from the group consisting of alkyl, alkenyl, alkynyl, cycloalkyl, aryl, and heteroaryl, the reacting of Intermediate 1 with Het is followed by a step of hydrolysis to convert —$COOR^{20'}$ into —COOH, or a salt thereof, to form the compound of Formulae 2, 3, 4, or 5. In preferred embodiments, $R^{20}$ is H, $R^{20'}$ is methyl, the reacting of Intermediate 1 with Het (e.g., pyridine or substituted pyridine as defined herein) also converts —$COOR^{20'}$ into —COOH, or a salt thereof, to form the compound of Formulae 2, 3, 4, or 5.

In some embodiments, the invention provides a method of synthesizing a compound of Formula 1, or a stereoisomer, a stereoisomeric mixture, or a salt thereof, the method comprising
a) reacting Reactant 10

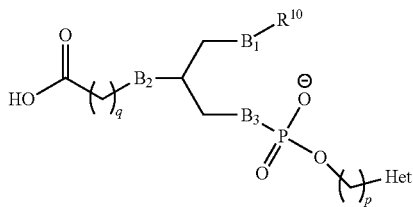

Reactant 10 with $R^{20}OH$ to form the compound of Formula 1, wherein $B_1$, $B_2$, $B_3$, $R^{10}$, Het, p, and q are defined above; and wherein $R^{20}$ is selected from the group consisting of alkyl, alkenyl, alkynyl, cycloalkyl, aryl, and heteroaryl. Preferably, $R^{20}$ is an alkyl (e.g., $C_{1-4}$ alkyl, e.g., methyl). In some embodiments, the reaction is catalyzed by an acid, e.g., HCl. Other known methods for forming an ester can also be used in step a).

In some embodiments, the method is directed to synthesizing compounds having a structure according to Formulae 2, 3, 4, or 5 (e.g., as described herein). In such embodiments, all of $B_1$, $B_2$, and $B_3$ are O, and suitable $R^{10}$, $R^{11}$, $R^{12}$, Het, p, and q for the methods described above are those as defined herein for the respective Formulae 2, 3, 4, or 5, wherein $R^{20}$ is selected from the group consisting of alkyl, alkenyl, alkynyl, cycloalkyl, aryl, and heteroaryl. Preferably, $R^{20}$ is an alkyl (e.g., $C_{1-4}$ alkyl, e.g., methyl).

Oxidized lipids of the invention (e.g., Formulae 1a, 1b, 2a, 2b, 3a, 3b, 4a, 4b, 5a, 5b) having certain enantiomeric purity (e.g., as described herein) can be obtained from racemic mixtures by techniques known in the art. Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

Oxidized lipids of the invention (e.g., Formulae 1a, 1b, 2a, 2b, 3a, 3b, 4a, 4b, 5a, 5b) having certain enantiomeric purity (e.g., as described herein) can also be synthesized by the general Methods A or B described herein using a starting material, or any synthetic intermediate, having certain enantiomeric purity, for example, (S)-1-(2'-octyl)dodecyl-2-(4'-carboxymethyl)butyl-glycerol, (S)-1-hexadecyl-2-(4'-carboxymethyl)butyl-glycerol, or (S)-1-eicosanyl-2-(4'-carboxymethyl)butyl-glycerol. The starting material, or any synthetic intermediate, having certain enantiomeric purity can be obtained by synthetic methods known in the art or by chiral separation from racemic mixtures as described herein.

In other embodiments, the present invention relates to a compound made by any of the methods of synthesis of the invention.

Pharmaceutical Compositions

Other embodiments of the invention relate to a pharmaceutical composition comprising an oxidized lipid of the invention. In some embodiments, the pharmaceutical composition comprises an oxidized lipid of the invention and a pharmaceutically acceptable vehicle. In other embodiments, the pharmaceutical composition comprises a therapeutically effective amount of the oxidized lipid. In some embodiments, the pharmaceutical composition comprises a therapeutically effective amount of the oxidized lipid and a pharmaceutically acceptable vehicle. As used herein, a therapeutically effective amount of an oxidized lipid is an amount effective to treat or prevent a disease or disorder of the present invention.

In other embodiments, the pharmaceutical compositions of the present invention can be orally administered.

In some embodiments, the pharmaceutical composition comprises a compound having a structure according to any of Formulae 1, 2, 3, 4, or 5 as described herein.

In other embodiments, the pharmaceutical composition comprises a compound having a structure of:

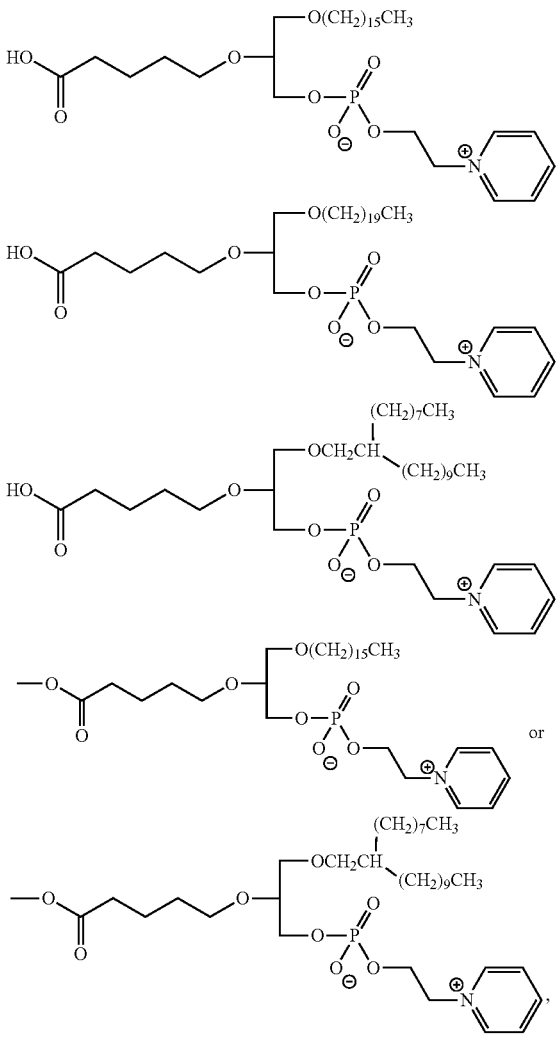

or a stereoisomer, a stereoisomeric mixture, or a salt thereof.

In some embodiments, the pharmaceutical composition comprises a compound selected from the group consisting of (R)-1-hexadecyl-2-(4'-carboxy)butyl-sn-glycero-3-phosphoric acid pyridiniumethyl ester (VB-701); (R)-1-eicosanyl-2-(4'-carboxy)butyl-sn-glycero-3-phosphoric acid pyridiniumethyl ester (VB-702); (R)-1-(2'-octyl)dodecyl-2-(4'-carboxy)butyl-sn-glycero-3-phosphoric acid pyridiniumethyl ester (VB-703); (R)-1-hexadecyl-2-(4'-carboxymethyl)butyl-sn-glycero-3-phosphoric acid pyridiniumethyl ester (VB-704); and (R)-1-(2'-octyl)dodecyl-2-(4'-carboxymethyl)butyl-sn-glycero-3-phosphoric acid pyridiniumethyl ester (VB-705). The prefix "(R)-" refers to the configuration of the C-2 carbon of the glycerol backbone. In some embodiments, the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In some embodiments, the pharmaceutical composition comprises a compound having a structure of:

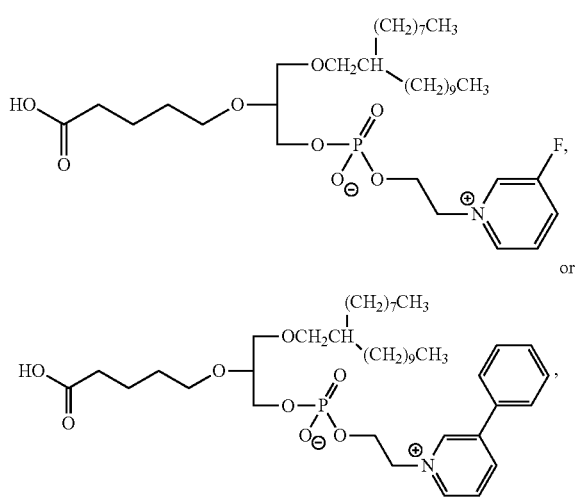

or a stereoisomer, a stereoisomeric mixture, or a salt thereof.

In some embodiments, the pharmaceutical composition comprises a compound selected from the group consisting of (R)-1-(2'-octyl)dodecyl-2-(4'-carboxy)butyl-glycero-sn-3-phosphoric acid 3-fluoro-pyridiniumethyl ester (VB-706) and (R)-1-(2'-octyl)dodecyl-2-(4'-carboxy)butyl-glycero-sn-3-phosphoric acid 3-phenyl-pyridiniumethyl ester (VB-707). The prefix "(R)-" refers to the configuration of the C-2 carbon of the glycerol backbone. In some embodiments, the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In other embodiments, the pharmaceutical composition treats or prevents fibrosis (e.g., liver fibrosis, kidney fibrosis, focal and segmental glomerulosclerosis, or any other fibrosis described herein) as well as, or better than, telmisartan. In other embodiments, the pharmaceutical composition reduces liver inflammation as well as, or better than, telmisartan. In other embodiments, the pharmaceutical composition reduces liver fibrosis as well as, or better than, telmisartan. In other embodiments, the pharmaceutical composition treats or prevents kidney fibrosis as well as, or better than, telmisartan. In other embodiments, the pharmaceutical composition treats or prevents focal and segmental glomerulosclerosis as well as, or better than, telmisartan.

In other embodiments, the pharmaceutical composition inhibits formation of ligand-induced phosphorylation of IKK, ERK, AKT or p38 comparable to or more than VB-201 (1-hexadecyl-2-(4'-carboxy)butyl-glycero-3-phosphocholine or 1-hexadecyl-2-(4'-carboxybutyl)-glycerol-3-phosphocholine)) inhibits formation of ligand-induced phosphorylation of IKK, ERK, AKT or p38. In other embodiments, the pharmaceutical composition inhibits ligand-induced cell migration comparable to or more than VB-201 inhibits ligand-induced cell migration. In other embodiments, the ligand is LPS, PGN, PAM3, or MCP1. In other embodiments, the cell migration is monocyte migration.

Methods of Treating or Preventing Fibrosis or Inflammatory Diseases or Disorders Embodiments of the invention relate to a method for treating or preventing fibrosis or an inflammatory disease or disorder comprising administering an oxidized lipid of the invention. In other embodiments, the invention relates to a method for treating or preventing an inflammatory disease or disorder. In other embodiments, the method comprises administering a therapeutically effective amount of an oxidized lipid of the invention to a subject in need thereof. In other embodiments, the method comprises administering a pharmaceutical composition of the invention.

The methods described herein can be used for treating or preventing all types fibrosis. In some embodiments of the methods of the invention, the fibrosis is pulmonary fibrosis, liver fibrosis, skin fibrosis or kidney fibrosis. In some embodiments of the methods of the invention, the fibrosis is heart fibrosis, bone marrow fibrosis, intestine fibrosis, joint fibrosis (knee, shoulder, or other joints), hand fibrosis, finger fibrosis, skeletal muscle fibrosis, neurofibrosis, and penis fibrosis. In other embodiments, the fibrosis is idiopathic pulmonary fibrosis (IPF), cystic fibrosis, progressive massive fibrosis, cirrhosis, steatohepatitis (fatty liver disease), nonalcoholic fatty liver disease (NAFLD), nonalcoholic steatohepatitis (NASH), endomyocardial fibrosis, myocardial infarction, atrial fibrosis, mediastinal fibrosis, myelofibrosis, retroperitoneal fibrosis, nephrogenic systemic fibrosis, keloid, Crohn's disease, scleroderma/systemic sclerosis, arthrofibrosis, Peyronie's disease, Dupuytren's contracture, adhesive capsulitis, or focal and segmental glomerulosclerosis. In some embodiments, the fibrosis is liver fibrosis. In some embodiments, the fibrosis is kidney fibrosis. In some embodiments, the subject in need of treatment or prevention of kidney fibrosis has a chronic kidney disease. In some embodiments, the fibrosis is focal and segmental glomerulosclerosis. In some embodiments, the subject in need of treatment or prevention of focal and segmental glomerulosclerosis has a chronic kidney disease.

In some embodiments, the fibrosis is a fibrosis that does not include idiopathic pulmonary fibrosis. In other embodiments, the fibrosis is a fibrosis that does not include cystic fibrosis. In other embodiments, the fibrosis is a fibrosis that does not include progressive massive fibrosis. In some embodiments, the fibrosis is a fibrosis that does not include cirrhosis. In some embodiments, the fibrosis is a fibrosis that does not include steatohepatitis (fatty liver disease). In some embodiments, the fibrosis is a fibrosis that does not include nonalcoholic fatty liver disease (NAFLD). In some embodiments, the fibrosis is a fibrosis that does not include nonalcoholic steatohepatitis (NASH). In some embodiments, the fibrosis is a fibrosis that does not include endomyocardial fibrosis. In some embodiments, the fibrosis is a fibrosis that does not include myocardial infarction. In some embodiments, the fibrosis is a fibrosis that does not include atrial fibrosis. In some embodiments, the fibrosis is a fibrosis that does not include medastinal fibrosis. In some embodiments, the fibrosis is a fibrosis that does not include myelofibrosis. In some embodiments, the fibrosis is a fibrosis that does not include retroperitoneal fibrosis. In some embodiments, the fibrosis is a fibrosis that does not include nephrogenic systemic fibrosis. In some embodiments, the fibrosis is a fibrosis that does not include keloid. In some embodiments, the fibrosis is a fibrosis that does not include Crohn's disease. In some embodiments, the fibrosis is a fibrosis that does not include scleroderma/systemic sclerosis. In some embodiments, the fibrosis is a fibrosis that does not include arthrofibrosis. In some embodiments, the fibrosis is a fibrosis that does not include Peyronie's disease. In some embodiments, the fibrosis is a fibrosis that does not include Dupuytren's contracture. In some embodiments, the fibrosis is a fibrosis that does not include adhesive capsulitis. In some embodiments, the fibrosis is a fibrosis that does not include focal and segmental glomerulosclerosis. In some embodiments, the fibrosis is a fibrosis that does not include fibrous lesions or plaques in the arteries.

In some embodiments, the oxidized lipid treats or prevents liver inflammation, but does not alter liver fibrosis. In other embodiments, the oxidized lipid treats or prevents liver fibrosis, but does not alter liver inflammation.

In other embodiments, the inflammatory disease or disorder is liver inflammation, atherosclerosis, rheumatoid arthritis, inflammatory bowel disease, ulcerative colitis, multiple sclerosis, or psoriasis.

In some embodiments, the inflammatory disease or disorder is an inflammatory cardiovascular disease or disorder, a cerebrovascular disease or disorder, or a peripheral vascular disease or disorder.

In some embodiments, the inflammatory disease or disorder is an inflammatory cardiovascular disease or disorder selected from the group consisting of occlusive diseases or disorders, atherosclerosis, cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune diseases or disorders, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

In some embodiments, the inflammatory disease or disorder is a cerebrovascular disease or disorder selected from the group consisting of stroke, cerebrovascular inflammation, cerebral hemorrhage, and vertebral arterial insufficiency.

In some embodiments, the inflammatory disease or disorder is a peripheral vascular disease or disorder is selected from the group consisting of gangrene, diabetic vasculopathy, ischemic bowel disease, thrombosis, diabetic retinopathy, and diabetic nephropathy.

In other embodiments, activity of TLR2, TLR4 and/or CD14 is inhibited in a treated cell. In some embodiments, activity of TLR2 and TLR4 is inhibited; activity of TLR4 and CD14 is inhibited; activity of TLR2 and CD14 is inhibited; or activity of TLR2, TLR4 and CD14 is inhibited.

In other embodiments, steatosis in a subject treated with an oxidized lipid of the invention is not reduced, compared to that in untreated or placebo-treated subjects. In other embodiments, liver lobular formation in a subject treated with an oxidized lipid of the invention is decreased, compared to that in untreated or placebo-treated subjects. In other embodiments, liver lobular formulation in a subject treated with an oxidized lipid of the invention is not decreased, compared to that in untreated or placebo-treated subjects. In other embodiments, steatosis in a subject treated with an oxidized lipid of the invention is not reduced and liver lobular formation in a subject treated with an oxidized lipid of the invention is decreased, compared to those in untreated or placebo-treated subjects, respectively. In other embodiments, steatosis in a subject treated with an oxidized lipid of the invention is not reduced and liver lobular formation in a subject treated with an oxidized lipid of the invention is not decreased, compared to those in untreated or placebo-treated subjects, respectively. In other embodiments, foam cell-like macrophages are decreased in a subject treated with an oxidized lipid of the invention, compared to that in untreated or placebo-treated subjects. In some embodiments, liver lobular formation and foam cell-like macrophages in a subject treated with an oxidized lipid of the invention are decreased, compared to those in untreated or placebo-treated subjects, respectively. In some embodiments, liver lobular inflammation in a subject treated with an oxidized lipid of the invention is decreased, compared to that in untreated or placebo-treated subjects. In some embodiments, liver lobular inflammation and foam cell-like macrophages in a subject treated with an oxidized lipid of the invention are decreased, compared to those in untreated or placebo-treated subjects, respectively. In some embodiments, liver lobular formation, liver lobular inflammation and foam cell-like macrophages in a subject treated with an oxidized lipid of the invention are decreased, compared to those in untreated or placebo-treated subjects, respectively. In some embodiments, liver lobular formation in a subject treated with an oxidized lipid of the invention is decreased by about 5% to about 50% (e.g., about 5%, about 10%, about 20%, about 30%, about 40%, about 50%, or any ranges between the specified values) compared to that in untreated or placebo-treated subjects. In some embodiments, the formation of foam cell-like macrophages in a subject treated with an oxidized lipid of the invention is decreased by about 5% to about 50% (e.g., about 5%, about 10%, about 20%, about 30%, about 40%, about 50%, or any ranges between the specified values) compared to that in untreated or placebo-treated subjects. In some embodiments, liver lobular inflammation in a subject treated with an oxidized lipid of the invention is decreased by about 5% to about 50% (e.g., about 5%, about 10%, about 20%, about 30%, about 40%, about 50%, or any ranges between the specified values) compared to that in untreated or placebo-treated subjects.

In some embodiments, the oxidized lipid is a compound having a structure according to any of Formulae 1, 2, 3, 4, or 5 as described herein.

In some embodiments, the oxidized lipid is a compound having a structure of:

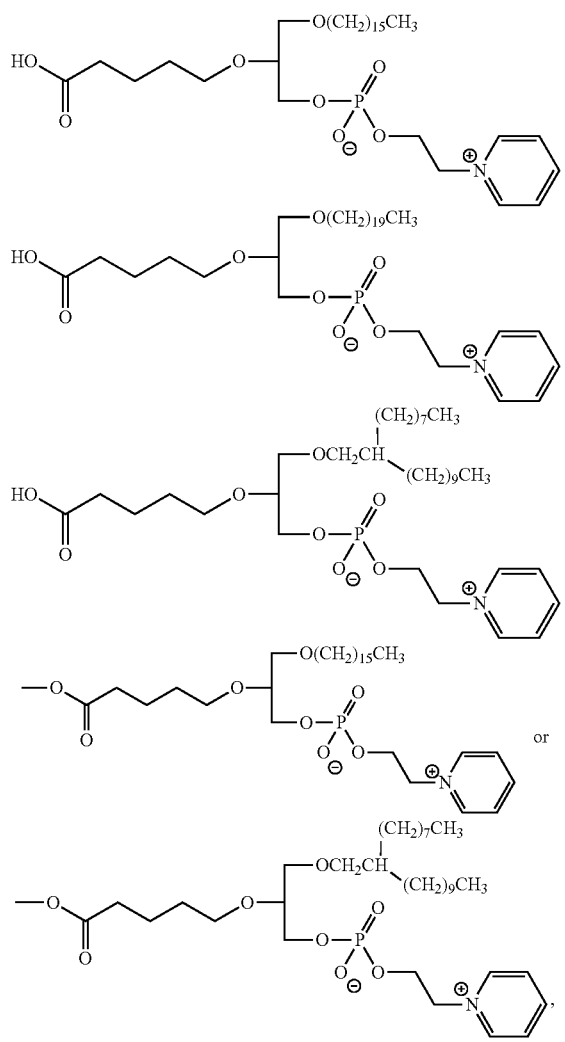

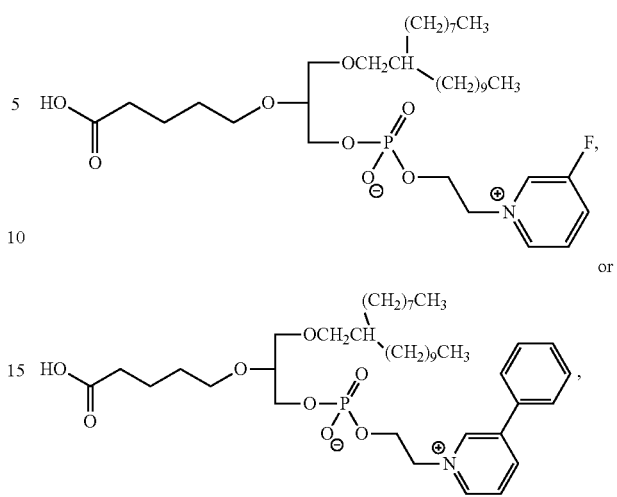

or a stereoisomer, a stereoisomeric mixture, or a salt thereof.

In some embodiments, the oxidized lipid is a compound selected from the group consisting of (R)-1-hexadecyl-2-(4'-carboxy)butyl-sn-glycero-3-phosphoric acid pyridiniumethyl ester (VB-701); (R)-1-eicosanyl-2-(4'-carboxy)butyl-sn-glycero-3-phosphoric acid pyridiniumethyl ester (VB-702); (R)-1-(2'-octyl)dodecyl-2-(4'-carboxy)butyl-sn-glycero-3-phosphoric acid pyridiniumethyl ester (VB-703); (R)-1-hexadecyl-2-(4'-carboxymethyl)butyl-sn-glycero-3-phosphoric acid pyridiniumethyl ester (VB-704); and (R)-1-(2'-octyl)dodecyl-2-(4'-carboxymethyl)butyl-sn-glycero-3-phosphoric acid pyridiniumethyl ester (VB-705). In some embodiments, the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In some embodiments, the oxidized lipid is a compound having a structure of:

or a stereoisomer, a stereoisomeric mixture, or a salt thereof.

In some embodiments, the oxidized lipid is a compound selected from the group consisting of (R)-1-(2'-octyl)dodecyl-2-(4'-carboxy)butyl-glycero-sn-3-phosphoric acid 3-fluoro-pyridiniumethyl ester (VB-706) and (R)-1-(2'-octyl)dodecyl-2-(4'-carboxy)butyl-glycero-sn-3-phosphoric acid 3-phenyl-pyridiniumethyl ester (VB-707). The prefix "(R)-" refers to the configuration of the C-2 carbon of the glycerol backbone. In some embodiments, the compound has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In other embodiments, the compound has an enantiomeric purity of from about 80% ee to about 100% ee, about 85% ee to about 100% ee, about 90% ee to about 100% ee, about 95% ee to about 100%, about 80% ee to about 99.5% ee, about 85% ee to about 99.5% ee, about 90% ee to about 99.5% ee, about 95% ee to about 99.5%, or any range thereof.

In other embodiments, the oxidized lipid compound treats or prevents fibrosis (e.g., liver fibrosis, kidney fibrosis, focal and segmental glomerulosclerosis, or any other fibrosis described herein) as well as, or better than, telmisartan. In other embodiments, the oxidized lipid compound reduces liver inflammation as well as, or better than, telmisartan. In other embodiments, the oxidized lipid compound reduces liver fibrosis as well as, or better than, telmisartan. In other embodiments, an oxidized lipid compound of the invention treats or prevents kidney fibrosis as well as, or better than, telmisartan. In other embodiments, an oxidized lipid compound of the invention treats or prevents focal and segmental glomerulosclerosis as well as, or better than, telmisartan.

In other embodiments, the oxidized lipid compound inhibits formation of ligand-induced phosphorylation of IKK, ERK, AKT, or p38 comparable to or more than VB-201 (1-hexadecyl-2-(4'-carboxy)butyl-glycero-3-phosphocholine or 1-hexadecyl-2-(4'-carboxybutyl)-glycerol-3-phosphocholine) inhibits formation of ligand-induced phosphorylation of IKK, ERK, AKT, or p38. In other embodiments, the compound inhibits ligand-induced cell migration comparable to or more than VB-201 inhibits ligand-induced cell migration. In other embodiments, the ligand is LPS, PGN, MCP1, or PAM3. In other embodiments, the cell migration is monocyte migration.

In other embodiments, the subject is a mammal or a human. In other embodiments, the human is a female. In other embodiments, the human is a male.

In some embodiments, an oxidized lipid of the invention is a compound having a structure according to Formula 6:

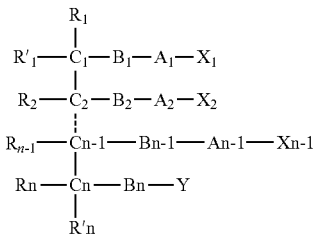

Formula 6 or a stereoisomer, a stereoisomeric mixture, or a salt thereof, wherein:

n is an integer from 1 to 6, wherein when n is 1, Cn, Bn, Rn, and Y are absent, and $C_1$ is attached to R'n;

each of $B_1, B_2, \ldots Bn-1$ and Bn is independently selected from the group consisting of oxygen, sulfur, nitrogen, phosphorus and silicon, wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy, and oxo;

each of $A_1, A_2, \ldots An-1$ and An is independently selected from the group consisting of CR"R'", C=O and C=S;

Y is a moiety having the general formula:

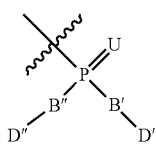

wherein:

each of U, B' and B" is independently selected from the group consisting of sulfur and oxygen; and each of D' and D" is independently selected from the group consisting of hydrogen, a negative charge, alkyl, amino substituted alkyl, heteroalicyclic substituted alkyl, heteroaryl substituted alkyl, cycloalkyl, phosphonate, and thiophosphonate; and each of $X_1, X_2, \ldots Xn-1$ is independently a saturated or unsaturated hydrocarbon having the general Formula 7:

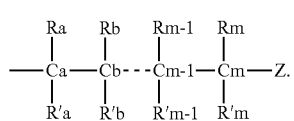

Formula 7 wherein m is an integer from 1 to 26; and

Z is selected from the group consisting of:

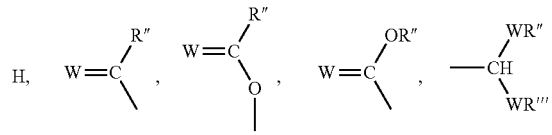

and —OR", wherein W is selected from the group consisting of oxygen and sulfur;

wherein at least one of $X_1, X_2, \ldots Xn-1$ comprises a Z other than hydrogen, and wherein:

each of $R_1, R'_1, R_2, \ldots Rn-1, Rn, R'n$, each of R" and R'" and each of Ra, R'a, Rb, R'b, ... Rm-1, R'm-1, Rm and R'm is independently selected from the group consisting of hydrogen, alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfonyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1, R'_1, R2, \ldots Rn-1, Rn$ and R'n and/or at least two of Ra, R'a, Rb, R'b, ... Rm-1, R'm-1, Rm and R'm form at least one four-, five- or six-membered aromatic, heteroaromatic, alicyclic or heteroalicyclic ring.

In some embodiments, an oxidized lipid of the invention is a compound having a structure according to Formula 6 as defined herein, or a stereoisomer, a stereoisomeric mixture, or a salt thereof, wherein Y is

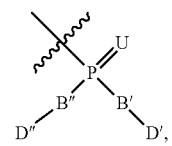

wherein:

n is 3;

each of U, B' and B" is oxygen; and wherein one of D' and D" is a heteroalicyclic substituted alkyl or heteroaryl substituted alkyl, and the other of D' and D" is hydrogen or a negative charge. In some embodiments, one of D' and D" is a heteroaryl substituted alkyl, and the other of D' and D" is hydrogen or a negative charge.

In some embodiments, the invention relates to deuterated analogs, prodrugs, hydrates, and solvates of any of the oxidized lipid described herein (e.g., having a structure according to Formulae 1-6).

EXAMPLES

Reference is now made to the following examples, which together with the above descriptions illustrate some embodiments of the invention in a non-limiting fashion.

Example 1

General Synthetic Procedures

Procedure A 1-alkyl-2-(4'-carboxymethyl)butyl-glycero-sn-3-phosphoric acid bromoethyl ester

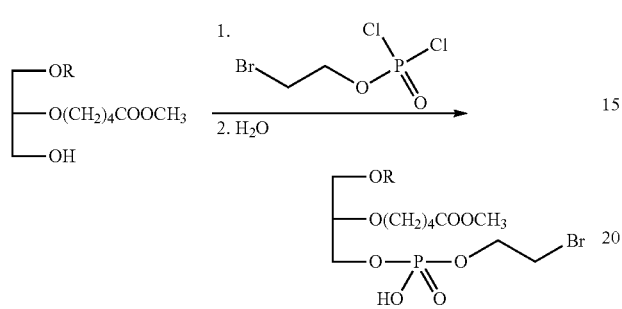

1-alkyl-2-(4'-carboxymethyl)butyl-glycerol was dried by azeotropic distillation from benzene. After cooling to room temperature under nitrogen, (2-bromoethyl)-phosphoryl-chloride (1.5 eq) was added and the mixture resulted was stirred at room temperature for 15 minutes. The reaction mixture was then cooled in an ice bath. Pyridine (anhydrous, 1.2 eq) was then added dropwise. The reaction mixture was then allowed to stir at room temperature overnight. After which, the solvent was removed under reduced pressure. Water was then added and the reaction mixture was refluxed for 1 hr. After cooling to room temperature, the reaction mixture was extracted with ether. The combined organic phase was washed with water, dried over sodium sulfate, and then concentrated under reduced pressure to yield 1-alkyl-2-(4'-carboxymethyl)butyl-glycero-sn-3-phosphoric acid bromoethyl ester.

1-alkyl-2-(4'-carboxy)butyl-glycero-sn-3-phosphoric acid pyridiniumethyl ester

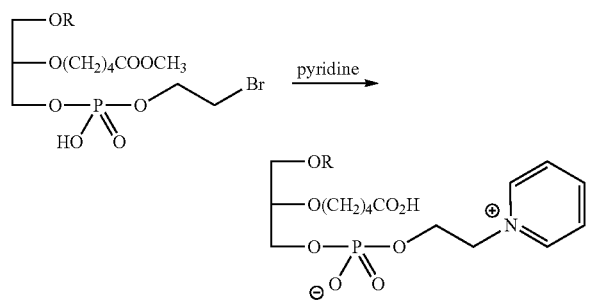

1-alkyl-2-(4'-carboxymethyl)butyl-glycero-sn-3-phosphoric acid bromoethyl ester was dissolved in pyridine (anhydrous). The reaction mixture resulted was refluxed for 22 hrs. After removal of the pyridine under reduced pressure, the residue was dissolved in methanol. Sodium bicarbonate (4.5 eq) was then added. The resulting mixture was refluxed for 1 hr and hot filtered. The residue obtained after washing of the filtrate with methanol and removal of solvent under reduced pressure was purified by chromatography on a column of silica gel. Elution with mixtures of CHCl$_3$:MeOH (5-20%, v/v), followed by CHCl$_3$:MeOH:H$_2$O (70:26:4, v/v/v).

Procedure B

O-tosyl Ethylene Glycol

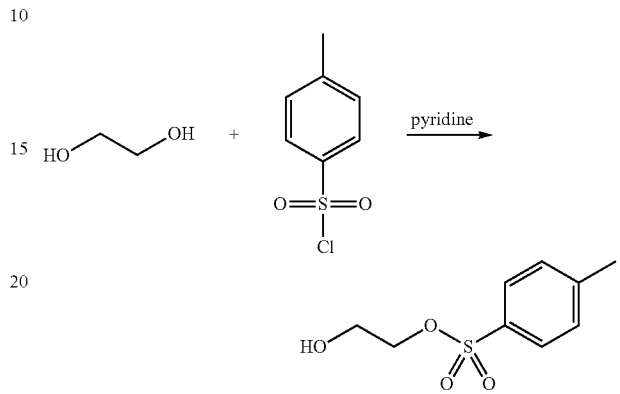

A solution of p-toluenesulfonyl chloride (7 g) in dichloromethane (anhydrous, 50 ml) was added dropwise at 0° C. to a stirred solution of ethylene glycol (anhydrous, 20 ml) in dichloromethane (anhydrous, 100 ml) and pyridine (anhydrous, 7 ml). The resulting mixture was stirred at room temperature overnight and then poured on ice and allowed to reach room temperature. The reaction mixture was extracted with dichloromethane (3×100 ml) and the combined organic phase was washed sequentially with water (150 ml), sulfuric acid (2%, 100 ml), water (150 ml), saturated sodium bicarbonate (150 ml) and again with water (150 ml). Removing the solvent under reduced pressure yielded O-tosyl ethylene glycol 7.74 g as a colorless oil.

1-alkyl-2-(4'-carboxymethyl)butyl-glycero-sn-3-phosphoric Acid Tosylethyl Ester

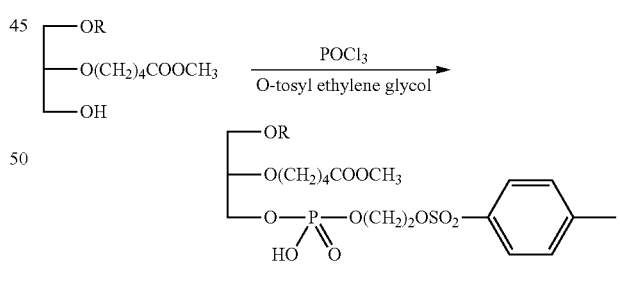

To a solution of 1-alkyl-2-(4'-carboxymethyl)butyl-glycerol (dried by azeotropic distillation with benzene) and triethylamine (3 eq) in dry THF, an ice cooled solution of Phosphorus oxychloride (1.2 eq) in dry THF was added dropwise (over 2 hrs). The reaction mixture was stirred at 0° C. for an additional 15 minutes and then at room temperature of 45 minutes. After which, the reaction mixture was cooled again to 0° C. A solution of O-tosyl ethylene glycol (1.1 eq, dried by azeotropic distillation from benzene) in dry THF was added dropwise over 30 min. The resulting mixture was stirred at room temperature for overnight, and then filtered. The solvent was removed under reduced pressure. The residue obtained was dissolved in water and was refluxed for 1 hr. After being cooled to room temperature, the reaction mixture was extracted with ether. The combined organic phase was washed with water and concentrated under reduced pressure. The residue resulted was purified by chromatography on silica gel. Elution with a mixture of CHCl$_3$:MeOH (5-20%, v/v), followed by removal of solvent under reduced pressure yielded 1-alky-2-(4'-carboxymethyl)butyl-glycero-sn-3-phosphoric acid tosylethyl ester.

1-alkyl-2-(4'-carboxy)butyl-glycero-sn-3-phosphoric Acid Pyridiniumethyl Ester

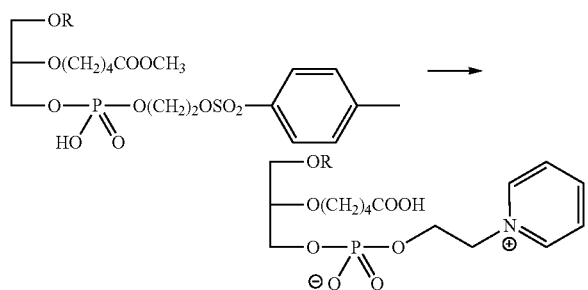

A solution of 1-alkyl-2-(4'-carboxymethyl)butyl-glycero-sn-3-phosphoric acid tosylethyl ester in pyridine was stirred and heated to 40° C. for 6 hrs. The solution was then cooled and stirred at room temperature overnight. After removing the solvent under reduced pressure, the residue obtained was purified by chromatography on silica gel. A mixture of CHCl$_3$:MeOH (5-20%, v/v) was used as initial eluent, which was followed by a mixture of CHCl$_3$:MeOH:H$_2$O (70:26:4, v/v/v). The fractions collected were concentrated under reduced pressure. The residue obtained was then dissolved in chloroform, which was dried over sodium sulfate. Removal of chloroform under reduced pressure then yielded purified 1-alkyl-2-(4'-carboxy)butyl-glycero-sn-3-phosphoric acid pyridiniumethyl ester.

The general procedures above are applicable for synthesis of the oxidized lipid described herein. For methyl ester methylation, there is an additional step in the procedure: methylation in methanol and HCl.

General Procedure for Methyl Ester Formation

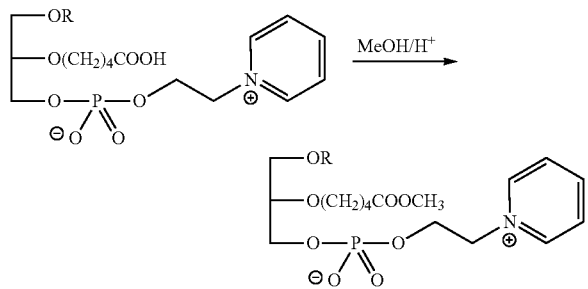

1-alkyl-2-(4'-carboxy)butyl-glycero-sn-3-phosphoric acid pyridiniumethyl ester was dissolved in methanol. Hydrochloric acid was added to the methanol solution and the mixture stirred at room temperature for 4 hrs. After which, water was added to the reaction mixture. The resulting mixture was extracted with CHCl$_3$. The organic phase was washed sequentially with water, saturated sodium bicarbonate and again with water, and then dried over sodium sulfate. Removal of the solvent under reduced pressure then yielded 1-alkyl-2-(4'-carboxymethyl)butyl-glycero-sn-3-phosphoric acid pyridiniumethyl ester.

Example 2

Synthesis of VB-703

VB-703 was synthesized by two synthetic procedures according to the general procedures described above.

Procedure A 1-(2'-octyl)dodecyl-2-(4'-carboxymethyl)butyl-glycero-sn-3-phosphoric Acid Bromoethyl Ester

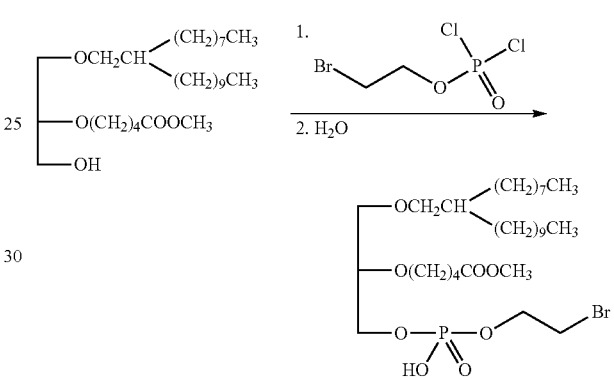

1-(2'-octyl)dodecyl-2-(4'-carboxymethyl)butyl-glycerol (13.75 g) was dissolved in benzene (100 ml) and dried by azeotropic distillation of 50 ml benzene. After cooling to room temperature under nitrogen, (2-bromoethyl)-phosphorylchloride (5.43 ml, 10.25 g) was added. The resulting mixture was stirred at room temperature for 15 minutes and then cooled to 0° C. Pyridine (anhydrous, 2.73 ml, 2.68 g) was added dropwise. The reaction mixture was stirred at room temperature overnight and then the solvent removed under reduced pressure. Water (100 ml) was added and the mixture refluxed for 1 hr. After cooling to room temperature, the reaction mixture was extracted with ether (3×100 ml) and washed with water (100 ml). Drying over sodium sulfate and removal of the solvent under reduced pressure yielded 15.06 g of 1-(2'-octyl)dodecyl-2-(4'-carboxymethyl)butyl-glycero-sn-3-phosphoric acid bromoethyl ester.

1-(2'-octyl)dodecyl-2-(4'-carboxy)butyl-glycero-sn-3-phosphoric Acid Pyridiniumethyl Ester

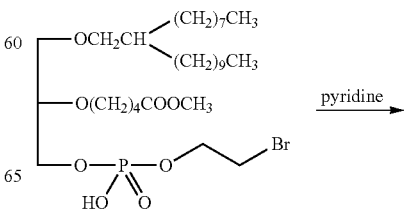

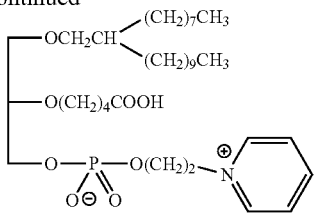

1-(2'-octyl)dodecyl-2-(4'-carboxymethyl)butyl-glycero-sn-3-3-phosphoric acid bromoethyl ester (15.06 g) was dissolved in pyridine (anhydrous, 50 ml) and the reaction mixture refluxed for 22 hrs. After removal of the solvent under reduced pressure, the residue was dissolved in methanol (100 ml) and sodium bicarbonate (10.68 g) was added. The resulting solution was refluxed for 1 hour (hr) and hot filtered. The residue obtained after washing of the filtrate with methanol (2×15 ml) and removal of solvent under reduced pressure was purified by chromatography on a column of silica gel (213 g). Elution with mixtures of CHCl$_3$:MeOH (5-20%, v/v) followed by CHCl$_3$:MeOH:H$_2$O (70:26:4, v/v/v). The solvent was removed under reduced pressure and the residue dissolved in chloroform. Drying of the solution over sodium sulfate, filtration and removal of the solvent under reduced pressure yielded 2.42 g 1-(2'-octyl)dodecyl-2-(4'-carboxy)butyl-glycero-sn-3-phosphoric acid pyridiniumethyl ester.

Procedure B 1-(2'-octyl)dodecyl-2-(4'-carboxymethyl)butyl-glycero-sn-3-phosphoric Acid Tosylethyl Ester

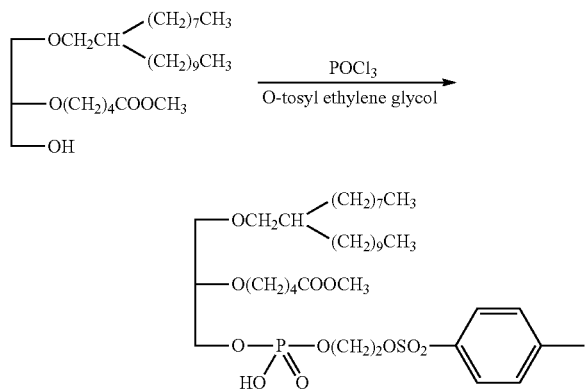

A solution of 1-(2'-octyl)dodecyl-2-(4'-carboxymethyl)butyl-glycerol (7.47 g, dried by azeotropic distillation with benzene) and triethylamine (7 ml) in dry THF (80 ml) was added dropwise for 2 hrs at 0° C. to a stirred solution of phosphorus oxychloride (2 ml) in dry THF (50 ml). The reaction mixture stirred at 0° C. for an additional 15 minutes and at room temperature for an additional 45 minutes. The reaction mixture was cooled again to 0° C. and a solution of O-tosyl ethylene glycol (3.65 g, dried by azeotropic distillation with benzene) in dry THF (50 ml) was added dropwise for 30 min. The resulting mixture was stirred at room temperature overnight, then filtered, and the solvent removed under reduced pressure. The residue was dissolved in water (100 ml), refluxed for 1 hr, then cooled and extracted with ether (2×100 ml). The combined organic phase was washed with water (100 ml) and the solvent removed under reduced pressure. The residue (9.62 g) was purified by chromatography on a column of silica gel (250 g). Elution with mixtures of CHCl$_3$:MeOH (5-20%, v/v) and removal of solvent under reduced pressure yielded 6.90 g of 1-(2'-octyl)dodecyl-2-(4'-carboxymethyl)butyl-glycero-sn-3-phosphoric acid tosylethyl ester.

1-(2'-octyl)dodecyl-2-(4'-carboxy)butyl-glycero-sn-3-phosphoric Acid Pyridiniumethyl Ester

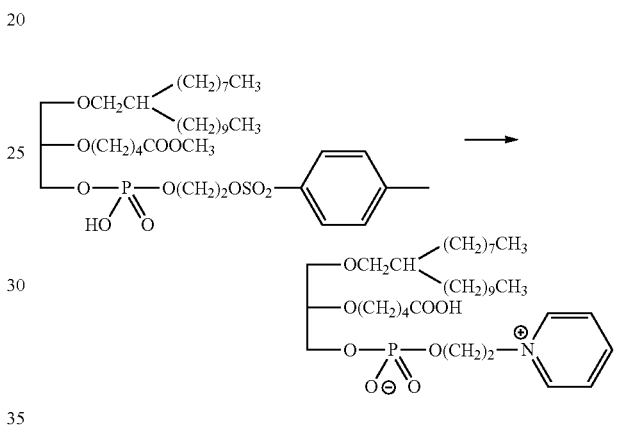

A solution of 1-(2'-octyl)dodecyl-2-(4'-carboxymethyl)butyl-glycero-sn-3-phosphoric acid tosylethyl ester (2.20 g) in pyridine (30 ml) was stirred and heated to 40° C. for 6 hrs, then cooled and stirred at room temperature overnight. After removing the solvent under reduced pressure, the residue was purified by chromatography on column of silica gel (95 g). Elution was done with mixtures of CHCl$_3$:MeOH (5-20%, v/v) followed by CHCl$_3$:MeOH:H2O (70:26:4, v/v/v). The solvent was removed under reduced pressure and the residue dissolved in chloroform. Drying of the solution over sodium sulfate, filtration and removal of the solvent under reduced pressure yielded 0.4 g of 1-(2'-octyl)dodecyl-2-(4'-carboxy)butyl-glycero-sn-3-phosphoric acid tosylethyl ester.

Mass spectrometry (MS): Calculated for $C_{35}H_{64}NO_8P$ 657. Found (ESI+) 658 [M+H]$^+$, 680 [M+Na]$^+$ and 696 [M+K]$^+$.

$^1$H-NMR (700 MHz, CDCl$_3$, TMS ref.): δ 0.88 (t, 6H, 2 CH3), 1.24-1.29 (m, 32H, 16 CH2), 1.53 (m, 1H, CH), 1.59 (tt, 2H, CH2), 1.69 (m, 1H, CH2), 2.34 (t, 2H, CH2), 3.29 (dt, 2H, CH2), 3.41 (m, 1H, CH2), 3.46 (m, 1H, CH2), 3.55 (m, 1H, CH2), 3.60 (m, 1H, CH), 3.66 (m, 1H, CH2), 3.77 (m, 1H, CH2), 3.88 (br s, 1H, CH2), 4.33 ((br, 2H, CH2), 4.87 ((br, 2H, CH2), 8.07 (t, 2H, meta-aromatic), 8.49 (t, 1H, para-aromatic), 9.03 (d, 2H, ortho-aromatic).

$^{13}$C-NMR: δ 14.17, 22.07, 22.85, 26.99, 27.01, 29.50, 29.54, 29.83, 29.84, 29.88, 30.29, 31.42, 31.46, 32.11, 34.09, 38.35, 62.41, 63.86, 65.99, 70.20, 71.16, 75.20, 78.29 (CH), 128.35 (meta aromatic), 145.66 (para aromatic), 145.75 (ortho aromatic), 176.67 (CO2H).

Example 3

Synthesis of VB-701

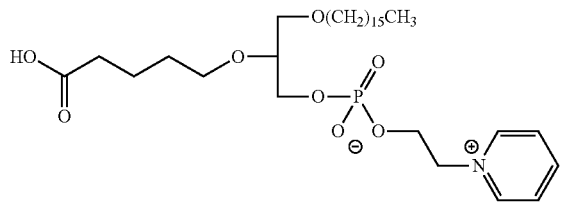

1-hexadecyl-2-(4'-carboxy)butyl-glycero-sn-3-phosphoric acid pyridiniumethyl ester (VB-701) was synthesized by following the general procedure A as described in Example 1. Mass spectrometry (MS): Calculated for $C_{31}H_{56}NO_8P$ 601 Found (ESI+) 602 $[M+H]^+$ and 624 $[M+Na]^+$.

Example 4

Synthesis of VB-702

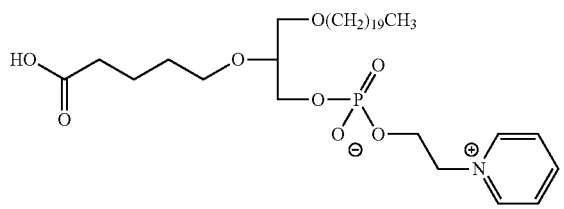

1-eicosanyl-2-(4'-carboxy)butyl-glycero-sn-3-phosphoric acid pyridiniumethyl ester (VB-702) was synthesized by following the general procedure A as described in Example 1. Mass spectrometry (MS): Calculated for $C_{35}H_{64}NO_8P$ 657.4. Found (ESI+) 658.5 $[M+H]^+$ and 680.5 $[M+Na]^+$.

$^1$H-NMR (700 MHz, CDCl$_3$, TMS ref.): δ 089 (t, 3H, CH3), 1.27-1.32 (m, 34H, 17 CH2), 1.54 (tt, 2H, CH2), 1.60 (m, 2H, CH2), 1.66 (m, 1H, CH2), 1.73 (m, 1H, CH2), 2.31 (br, t, 2H, CH2), 3.41 (m, 1H, CH2), 3.42 (m, 1H, CH2), 3.47 (m, 1H, CH2), 3.56 (m, 1H, CH), 3.58 (m, 1H, CH2), 3.65 (m, 1H, CH2), 3.80 (m, 1H, CH2), 3.88 (m, 1H, CH2), 4.38 ((br, 2H, CH2), 4.95 ((br, 2H, CH2), 8.10 (t, 2H, aromatic), 8.52 (t, 1H, aromatic), 9.10 (br, 2H, aromatic).
$^{13}$C-NMR: δ 14.22, 22.41, 22.99, 29.68, 29.85, 29.98-30.02, 32.26, 35.24, 62.51, 64.24, 66.02, 70.39, 70.56, 72.17, 78.27 (CH), 128.47 (aromatic), 145.72 (aromatic), 146.09 (aromatic), 179.08 (CO2H).

Example 5

Synthesis of VB-704

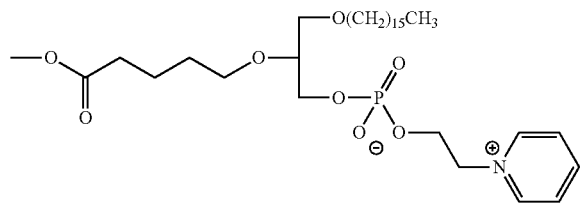

1-hexadecyl-2-(4'-carboxymethyl)butyl-glycero-sn-3-phosphoric acid pyridiniumethyl ester (VB-704) was synthesized by following the general procedure for methyl ester formation as described in Example 1. Mass spectrometry (MS): Calculated for $C_{32}H_{58}NO_8P$ 615. Found (ESI+) 616 $[M+H]^+$ and 638 $[M+Na]^+$.

Example 6

Synthesis of VB-705

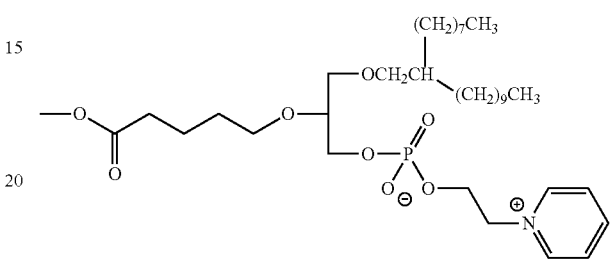

1-(2'-octyl)dodecyl-2-(4'-carboxymethyl)butyl-glycero-sn-3-phosphoric acid pyridiniumethyl ester (VB-705) was synthesized by following the general procedure for methyl ester formation as described in Example 1. Mass spectrometry (MS): Calculated for $C_{36}H_{66}NO_8P$ 671. Found (ESI+) 672 $[M+H]^+$ and 694 $[M+Na]^+$.

Example 7

Synthesis of VB-706

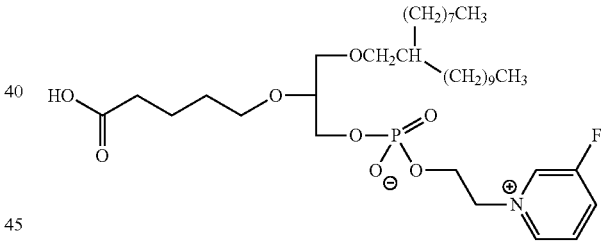

1-(T-octyl)dodecyl-2-(4'-carboxy)butyl-glycero-sn-3-phosphoric acid 3-fluoro-pyridiniumethyl ester (VB-706) was synthesized by following the general procedure B as described in Example 1. Mass spectrometry (MS): Calculated for $C_{35}H_{63}FNO_8P$ 675.43. Found (ESI+) 676.58 $[M+H]^+$ and 698.57 $[M+Na]^+$.

$^1$H-NMR (700 MHz, CDCl$_3$, TMS ref.): δ 088 (t, 6H, 2 CH3), 1.26-1.30 (m, 32H, 16 CH2), 1.53 (m, 1H, CH), 1.60 (tt, 2H, CH2), 1.69 (m, 1H, CH2), 2.31 (t, 2H, CH2), 3.30 (dt, 2H, CH2), 3.42 (m, 1H, CH2), 3.46 (m, 1H, CH2), (3.55 (m, 1H, CH2), 3.60 (m, 1H, CH2), 3.68 (m, 1H, CH2), 3.76 (m, 1H, CH2), 3.89 (m, 1H, CH2), 4.31 (br, 2H, CH2), 4.88 ((br, 2H, CH2), 8.14 (br, 1H, meta-aromatic), 8.35 (t, 1H, para-aromatic), 8.96 (d, 1H, ortho-aromatic), 9.25 (s, 1H, ortho-aromatic).
$^{13}$C-NMR: δ 14.18, 22.39, 22.88, 27.02, 27.04, 29.50-30.30, 31.44, 31.48, 32.14, 35.00, 38.37, 63.08, 63.66, 66.08, 70.30, 75.24, 78.37 (CH), 129.65 (meta aromatic), 133.36 (para aromatic), 135.79 (ortho-aromatic), 143.05 (ortho aromatic); 160.81 (CF), 178.16 (CO2H).
$^{19}$F NMR (376.4 MHz)−111.55.

Example 8

Synthesis of VB-707

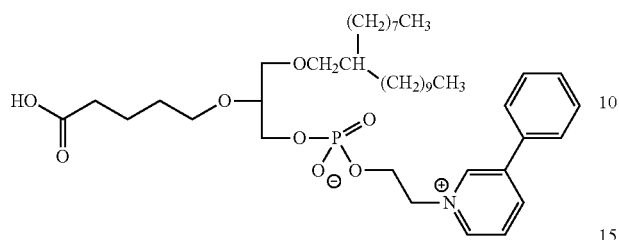

1-(2'-octyl)dodecyl-2-(4'-carboxy)butyl-glycero-sn-3-phosphoric acid 3-phenyl-pyridiniumethyl ester (VB-707) was synthesized by following the general procedure B as described in Example 1. Mass spectrometry (MS): Calculated for $C_{41}H_{68}NO_8P$ 733. Found (ESI+) 734 $[M+H]^+$ and 756 $[M+Na]^+$.

Example 9

VB-701 Inhibits LPS (TLR4)-Induced Signaling in Human Monocytes (Primary CD14+)

Methods and Materials
Isolation of Monocytes

Venous blood samples were obtained from healthy male donors in compliance with the Institutional Review Board at the Sheba Medical Center, Ramat Gan, Israel. PBMCs were isolated on Ficoll-Paque PLUS (GE Healthcare, Uppsala, Sweden) using 50 ml Leucosep tubes (Greiner Bio-One, Frickenhausen, Germany). Cells were washed in PBS (Kibbutz Beit Haemek, Israel) and incubated at 4° C. for 15 minutes in a buffer containing PBS and 0.5% bovine serum albumin (BSA) with human CD14 microbeads (Miltenyi Biotec, Bergisch Gladbach, Germany).

Activation of Cells and Western Blotting

Cells ($10^6$/ml) were pretreated for 20 min with VB-201 (1-hexadecyl-2-(4'-carboxy)butyl-glycero-3-phosphocholine or 1-hexadecyl-2-(4'-carboxybutyl)-glycerol-3-phosphocholine) or VB-701 at the doses indicated in FIG. 2, or with solvent (Sol), followed by 15 min activation with 100 ng/ml lipopolysaccharide (LPS) or were untreated (Unt). Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk or BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-p38 (Cat. No. 4511; 1:1000) and p-IKK (Cat. No. 2697; 1:1000) were from Cell Signaling Technology (Danvers, Mass., USA). p-ERK1/2 (Cat. No. M8159; 1:10 000) was purchased from Sigma (Israel). αTubulin (Tub) served as a loading control.

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.

Results

FIG. 2 shows that VB-701 and VB-201 inhibit formation of p-IKK, p-ERK and p-p38 induced by LPS in human monocytes. Accordingly, VB-701 and VB-201 inhibit LPS (TLR4)-induced signaling in human monocytes (primary CD14+).

Example 10

VB-701 Inhibits PGN (TLR2)-Induced Signaling in Human Monocytes (THP-1 Cell Line)

Methods and Materials
Activation of Cells and Western Blotting

The monocytic THP-1 cell line was purchased from the American Type Tissue Culture Collection (ATCC Cat. No. TIB-202). Cells ($10^6$/ml) were pretreated for 20 min with VB-201 or VB-701 at the doses indicated in FIG. 3, or with solvent, followed by activation with 20 μg/ml peptidoglycan (PGN) (InvivoGen, San Diego, Calif.) for 15 minutes, or were untreated ("Unt"). Cells were washed and resuspended in lysis buffer containing 1:100 dithiothreitol (DTT), phosphatase and protease inhibitor (Thermo Scientific). Samples were loaded onto a precast Criterion TGX gel (Bio-Rad, Hemel Hempstead, UK) and transferred onto nitrocellulose membrane. Blots were blocked with 5% milk or BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-p38 (Cat. No. 4511; 1:1000) and p-IKK (Cat. No. 2697; 1:1000) were from Cell Signaling Technology (Danvers, Mass., USA). p-ERK1/2 (Cat. No. M8159; 1:10000) was purchased from Sigma (Israel). αTubulin served as a loading control.

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.

Results

FIG. 3 shows that VB-701 and VB-201 inhibit formation of p-IKK, p-ERK and p-p38 induced by PGN in THP-1 cells. Accordingly, VB-701 and VB-201 inhibit PGN (TLR2)-induced signaling.

Example 11

VB-701 Inhibits MCP-1-Induced Signaling in Human Monocytes (THP-1 Cell Line)

Methods and Materials
Activation of Cells and Western Blotting

Figure 4:
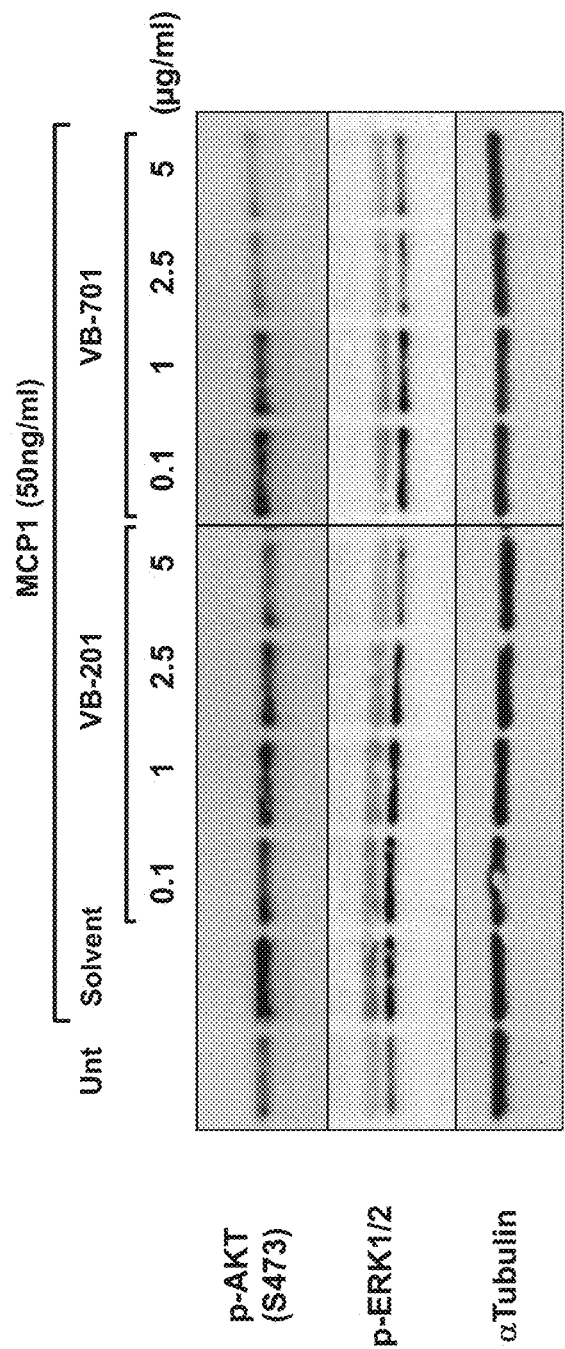
FIG. 4 shows VB-701 inhibits MCP-1-induced signaling in human monocytes (THP-1 cell line).

THP-1 cells ($10^6$/ml) were pretreated for 20 min with VB-201 or VB-701 at the doses indicated in FIG. 4, or with solvent, followed by activation with 50 ng/ml MCP1, or were untreated ("Unt"). Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk dr BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-ERK1/2 (Cat. No. M8159; 1:10000) was purchased from Sigma (Israel). p-AKT (Cat. No. 4060; 1:1000) was purchased from Cell Signaling Technology (Danvers, Mass.). αTubulin served as a loading control and was purchased from Sigma (Israel).

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.
Results FIG. 4 shows that VB-701 and VB-201 inhibit formation of p-AKT and p-ERK induced by MCP1 in THP-1 cells. Accordingly, VB-701 and VB-201 inhibit MCP1-induced signaling.

Example 12

VB-701 Inhibits Chemokine-Induced Migration of Human Monocytes (Primary CD14+)

Methods and Materials
Isolation of Monocytes

Venous blood samples were obtained from healthy male donors in compliance with the Institutional Review Board at the Sheba Medical Center, Ramat Gan, Israel. PBMCs were isolated on Ficoll-Paque PLUS (GE Healthcare, Uppsala, Sweden) using 50 ml Leucosep tubes (Greiner Bio-One, Frickenhausen, Germany). Cells were washed in PBS (Kibbutz Beit Haemek, Israel) and incubated at 4° C. for 15 minutes in a buffer containing PBS and 0.5% bovine serum albumin (BSA) with human CD14 microbeads (Miltenyi Biotec, Bergisch Gladbach, Germany).
Activation of Cells and Cell Migration Trans-Well Assay Cells ($10^6$/ml) were pretreated for 20 min with VB-201 or VB-701 at the doses indicated in FIG. 5, or with solvent (Sol).

Figure 5:
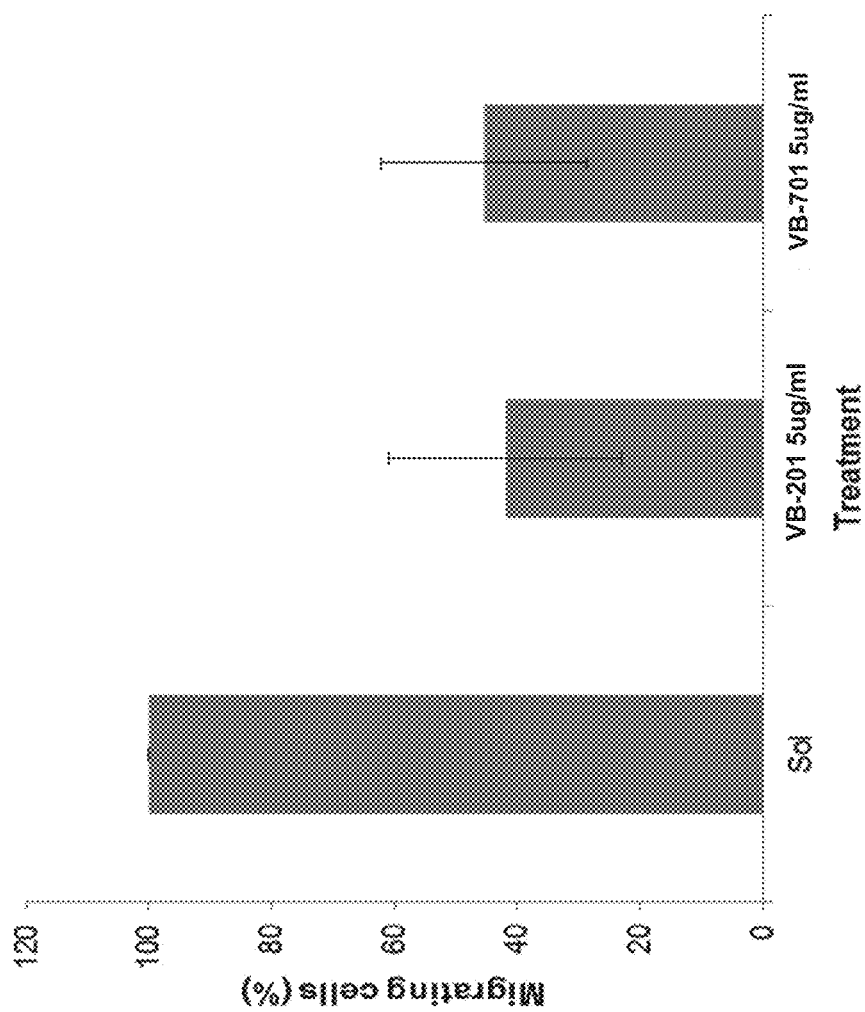
FIG. 5 shows VB-701 inhibits chemokine-induced migration of human monocytes (primary CD14+).

To test for chemokine-induced cell migration, RANTES (100 ng/ml; Cat. No. 300-06, PeproTech, Israel) and MCP-1 (50 ng/ml; Cat. No. 300-04, PeproTech, Israel) were dissolved in RPMI-1640 medium supplemented with 0.5% fetal bovine serum (FBS) and placed at the lower chamber of QCM 24-well, 5 mm pore, migration assay plates (Corning-Costar, Corning, N.Y.). Cells ($3\times10^5$) were seeded in the upper chamber and incubated for 2-4 hours. Subsequently, the number of cells which migrated to the lower compartment was determined by fluorescence-activated cell sorting (FACS).
Results FIG. 5 shows that VB-701 and VB-201 inhibit chemokine-induced migration of human monocytes (primary CD14+).

Example 13

VB-702 Inhibits LPS (TLR4)-Induced Signaling in Human Monocytes (Primary CD14+)

Figure 6:
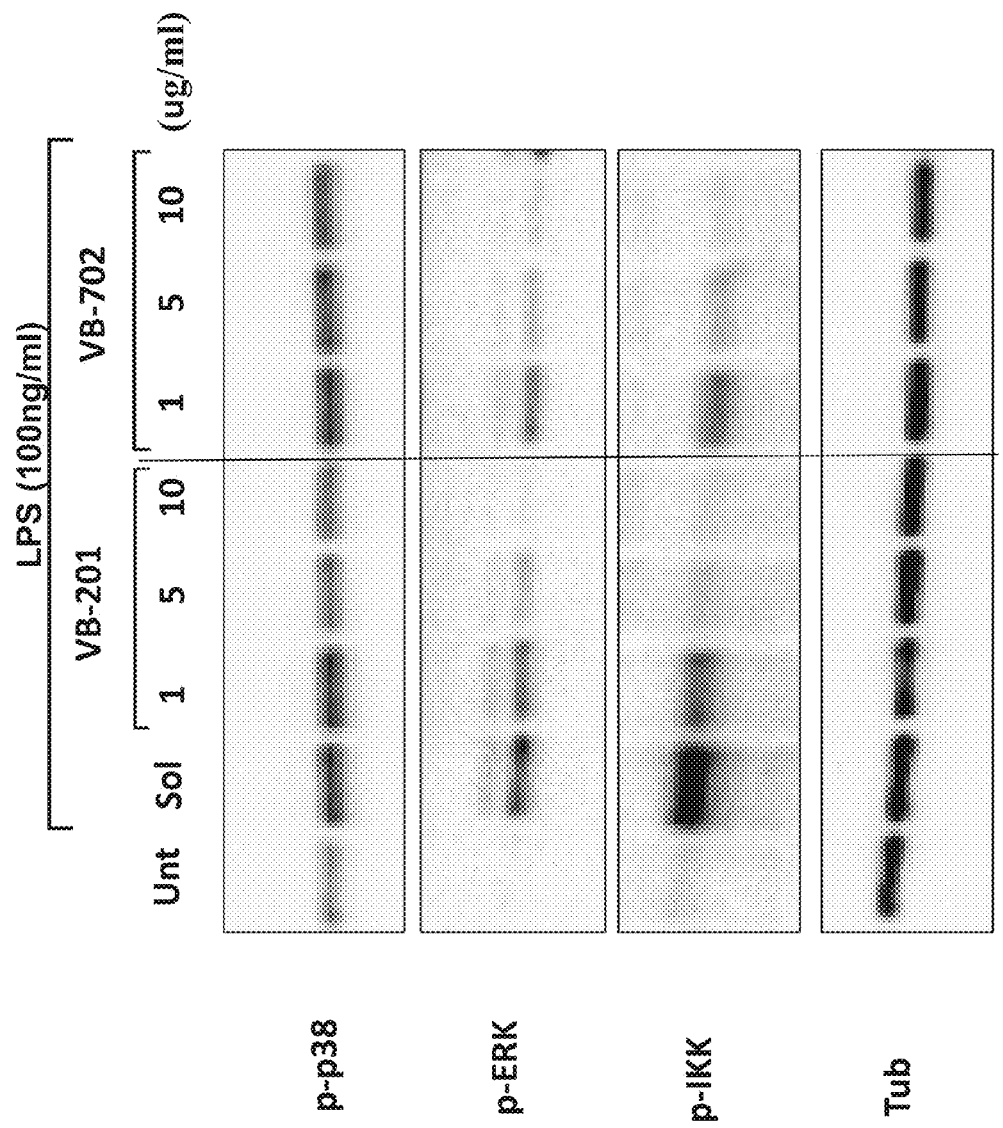
FIG. 6 shows VB-702 inhibits LPS (TLR4)-induced signaling in human monocytes (primary CD14+).

Human monocytes were obtained, treated and analyzed by western blot as described in Example 9 and FIG. 6. FIG. 6 shows that VB-702 and VB-201 inhibit formation of p-IKK, p-ERK and p-p38 induced by LPS in human monocytes. Accordingly, VB-702 and VB-201 inhibit LPS (TLR4)-induced signaling in human monocytes (primary CD14+).

Example 14

VB-702 Inhibits RANTES-Induced Signaling in Human Monocytes (Primary CD14+)

Figure 7:
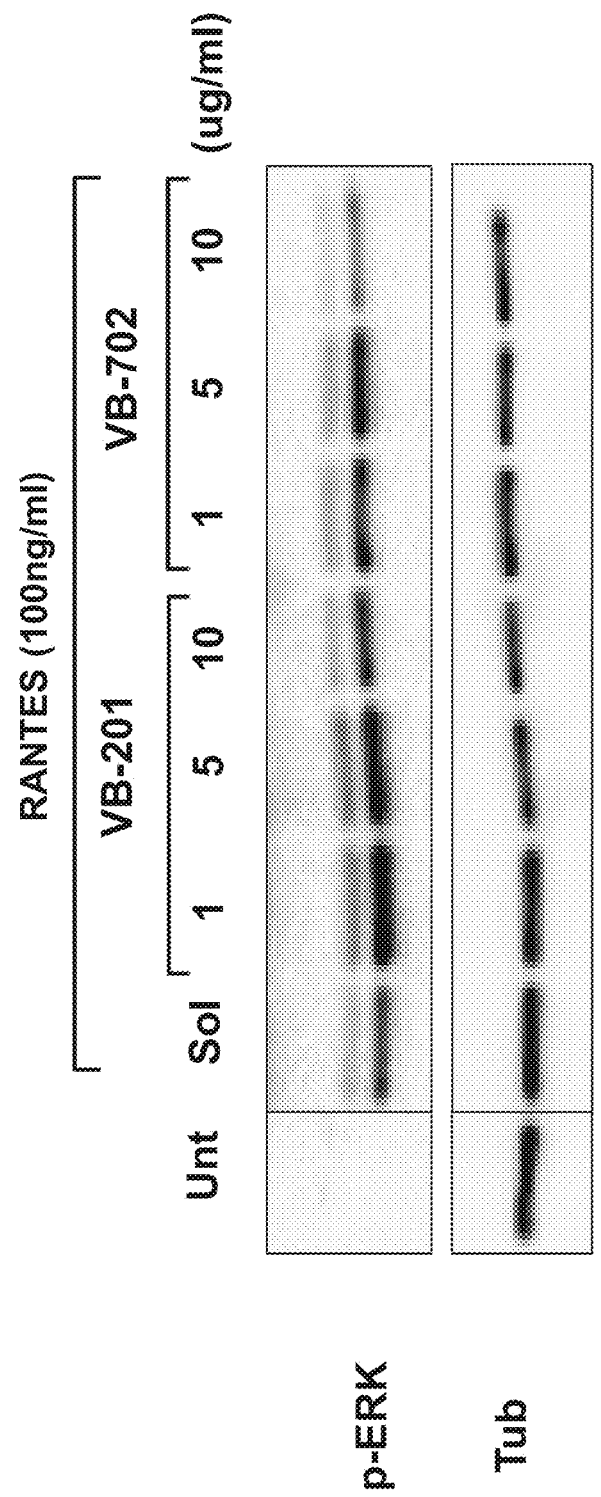
FIG. 7 shows VB-702 inhibits RANTES-induced signaling in human monocytes (primary CD14+).

Human monocytes were obtained, treated and analyzed by western blot as described in Example 9 and FIG. 7, except that cells were induced with RANTES (100 ng/ml; Cat. No. 300-06, PeproTech, Israel) for 15 minutes. FIG. 7 shows that VB-702 and VB-201 inhibit formation of p-ERK induced by RANTES in human monocytes. Accordingly, VB-702 and VB-201 inhibit RANTES-induced signaling in human monocytes (primary CD14+).

Example 15

VB-702 Inhibits Chemokine-Induced Migration of Human Monocytes (Primary CD14+)

Human monocytes were obtained, treated and analyzed for cell migration by trans-well assay as described in Example 12 and FIG. 8. FIG. 8 shows that VB-702 and VB-201 inhibit chemokine-induced migration of human monocytes (primary CD14+).

Example 16

VB-701 and VB-702 Inhibit IL-12p40 Levels in Human Monocytes (Primary CD14+) Stimulated with LPS (Via TLR4) or Pam3CSK4 (TLR2-Stimulated)

Methods and Materials

Human monocytes were obtained as described in Example 9 and FIG. 9A-9B. Human monocytes were seeded ($10^6$/ml) and pretreated for 1 hour with VB-201, VB-701 or VB-702, followed by 24 hour activation with 100 ng/ml LPS from *Escherichia coli* strain 055:B5 (Sigma, Israel) (FIG. 9A) or 300 ng/ml Pam3CSK4 (InvivoGen, San Diego, Calif., USA) (FIG. 9B) to induce cytokine production. IL-12/23p40 concentration in the supernatant was then measured by ELISA (R&D systems, Cat. No. DY1240). Cells activated with solvent (0.5% ethanol in PBS) were used as a control.
Results FIGS. 9A-9B show that VB-201, VB-701 and VB-702 inhibit IL-12p40 levels in human monocytes (primary CD14+) LPS (TLR4)- and Pam3CSK4 (TLR2)-stimulated.

Example 17

VB-703 Inhibits LPS (TLR4)-Induced Signaling, LPS Binding, Liver Inflammation and Fibrosis Methods and Materials
Isolation of Monocytes Venous blood samples were obtained from healthy male donors in compliance with the Institutional Review Board at the Sheba Medical Center, Ramat Gan, Israel. PBMCs were isolated on Ficoll-Paque PLUS (GE Healthcare, Uppsala, Sweden) using 50 ml Leucosep tubes (Greiner Bio-One, Frickenhausen, Germany). Cells were washed in PBS (Kibbutz Beit Haemek, Israel) and incubated at 4° C. for 15 minutes in a buffer containing PBS and 0.5% bovine serum albumin (BSA) with human CD14 microbeads (Miltenyi Biotec, Bergisch Gladbach, Germany).

Activation of Cells and Western Blotting

Cells ($10^6$/ml) were pretreated for 20 min with VB-201 or VB-703 followed by 15 min activation with 100 ng/ml LPS. Cells were washed and resuspended in lysis buffer containing 1:100 dithiothreitol (DTT), phosphatase and protease inhibitors (Thermo Scientific). Samples were loaded onto a precast Criterion TGX gel (Bio-Rad, Hemel Hempstead, UK) and transferred onto nitrocellulose membrane. Blots were blocked with 5% milk or BSA in Tris buffered saline and Tween 20 (TBST) for 1 h, followed by incubation with primary and secondary antibodies. Membranes were developed using an ECL kit (Thermo Scientific). The following antibodies were used for immunoblotting:

Primary antibodies: p-p38 (Cat. No. 4511; 1:1000) and p-IKK (Cat. No. 2697; 1:1000) were from Cell Signaling Technology (Danvers, Mass., USA). p-ERK1/2 (Cat. No. M8159; 1:10 000) was purchased from Sigma (Israel). Heat shock protein (HSP) 90 (Cat. No. 13119; 1:500) was from Santa Cruz Biotechnology (Santa Cruz, Calif., USA).

Secondary antibodies: HRP donkey anti-rabbit (1:5000) and HRP goat anti-mouse (1:3000) were from Jackson ImmunoResearch (West Grove, Pa., USA). HRP donkey anti-goat (1:5000) was from Santa Cruz Biotechnology.

LPS Binding Inhibition Assay

To assess interference with lipopolysaccharide (LPS) binding, VB-201 or VB-703 were incubated for 20 min with cells ($10^6$/ml) after which 100 ng/ml of biotin-LPS (InvivoGen) was added for an additional 15 minutes, all at 4° C. Cells were washed, resuspended in FACS buffer and analyzed on a FACS-Calibur device.

Induction of NASH and Liver Fibrosis

Neonatal male mice exposed to low-dose streptozotocin (STZ) develop liver steatosis with diabetes. Continuous high fat diet (HFD) increases lobular inflammation with foam cell-like macrophages, showing nonalcoholic steatohepatitis (NASH) pathology. NASH was induced in 40 male mice by a single subcutaneous injection of 200 µg per mouse of STZ two days after birth and feeding HFD [57 kcal % fat]) from four weeks of age. Vehicle, VB-703 (4 mg/kg), or telmisartan (10 mg/kg) as positive control, were administered once daily for three weeks, starting from six weeks of age. Mice were sacrificed at nine weeks of age.

Steatohepatitis and Fibrosis Evaluation

Liver pathology was used to determine the effect of VB-703 on liver inflammation and fibrosis. Histology slides were stained with hematoxylin/eosin (H&E) to assess inflammation. The inflammation score was determined as follows:

0—no inflammatory foci
1—<2 inflammatory foci
2—2-4 inflammatory foci
3—>4 inflammatory foci Histology slides were stained with Sirius red to determine collagen content as a marker for the extent of fibrosis.

Q-PCR

RNA was prepared from livers from normal mice and NASH-induced mice treated with vehicle, VB-703, or telmisartan, using RNeasy mini kit (Qiagen). For cDNA preparation, 2 µg of RNA was combined with qScript reaction mix and qScript Reverse Transcriptase (Quanta BioSciences) for 5 min at 22° C. and then; for 30 min at 42° C. Reaction was ended by incubation for an additional 5 min at 85° C. All real time PCR reactions were performed using the 7300 Real Time PCR System (Applied Biosystems). Q-PCR with mouse ready set of probe with primer was used for IL-1β, IL-12/23p40 and MCP-1 (Applied Biosystems). GAPDH was used to normalize RNA levels.

Results

Effect of VB-703 and VB-201 on TLR4-Mediated Signaling Events

To determine the effect of VB-201 and VB-703 on TLR4-mediated signaling pathways, isolated human primary monocytes were preincubated with VB-201 or VB-703 and then activated with LPS. FIG. 10A shows that VB-703 inhibited inflammatory cell signaling molecules phosphorylated ERK kinase (p-ERK), phosphorylated p38 (p-p38) and phosphorylated IKK kinase (p-IKK) in a dose dependent manner. Moreover, VB-703 had at least a 10-fold higher efficacy in inhibiting TLR4-driven protein phosphorylation than VB-201. The effect of VB-703 on the binding of LPS to the TLR4 complex was then tested. FIG. 10B shows that VB-703 inhibited the binding of LPS with an IC50 of ~0.5 µg/ml, more than a 10-fold lower IC50 than that of VB-201 (~7 µg/ml).

VB-703 Inhibits Liver Fibrosis

The effect of VB-703 on liver inflammation and fibrosis in a NASH mouse model was tested. Treatment with VB-703 significantly decreased fibrosis by 58% compared to vehicle treated mice (FIGS. 11A-11B) This effect was greater than of the positive control telmisartan (47%). However, VB-703 did not appear to significantly alter steatosis (FIGS. 12A-12B).

VB-703 Inhibits Expression of Inflammation Mediators

FIGS. 21A-21C show that the expression of two pro-inflammatory cytokines, IL-1β and IL-12/23p40, and the chemokine MCP-1 were significantly inhibited in livers taken from NASH-induced mice that were treated with VB-703.

Example 18

VB-703 Inhibits PGN (TLR2)-Induced Signaling in Human Monocytes (THP-1 Cell Line)

THP-1 cells were obtained, treated and analyzed by western blot as described in Example 10 and FIG. 13. FIG. 13 shows that VB-703 and VB-201 inhibit formation of p-IKK, p-ERK and p-p38 induced by PGN THP-1 cells. Accordingly, VB-703 and VB-201 inhibit PGN (TLR2)-induced signaling in human monocytes (THP-1 cell line).

Example 19

VB-703 Inhibits IL-6 Secretion in LPS (TLR4)-Stimulated Monocyte-Derived Dendritic Cells (Mo-Derived DCs)

Methods and Materials

To generate monocyte-derived DC (Mo-DCs), CD14+ monocytes were counted, washed and seeded ($10^6$/ml) in medium containing RPMI-1640, L-glutamine, β-mercaptoethanol, 10% fetal calf serum (FCS), sodium pyruvate, non-essential amino acids, 0.01 M HEPES, antibiotics (penicillin, streptomycin), 50 ng/ml human granulocyte-macrophage colony-stimulating factor (GMCSF) and 20 ng/ml human IL-4 (both from PeproTech Asia, Israel). Medium was replaced every 2-3 days. Mo-DCs were collected 5-6 days post-culture, counted and seeded ($10^6$/ml). Cells were pretreated for 1 hour with VB-201 or VB-703, followed by 24 hours activation with 100 ng/ml LPS from *Escherichia coli* strain 055:B5 (Sigma, Israel) to induce cytokine production. IL-6 concentration (FIG. 14) and IL-12/23p40 (FIG. 15) concentration in supernatant were measured by ELISA (R&D systems, Cat. No. DY1240 and Cat. No.

DY206, respectively). Cells activated with solvent (0.5% ethanol in PBS) were used as a control.
Results
FIGS. 14 and 15 show VB-703 and VB-201 inhibit IL-6 (FIG. 14) and IL-12p40 (FIG. 15) secretion in LPS (TLR4) stimulated Mo-Derived DCs.

Example 20

VB-704 does not Inhibit LPS-Biotin Binding to Human Monocytes (Primary CD14+)

Figure 16:
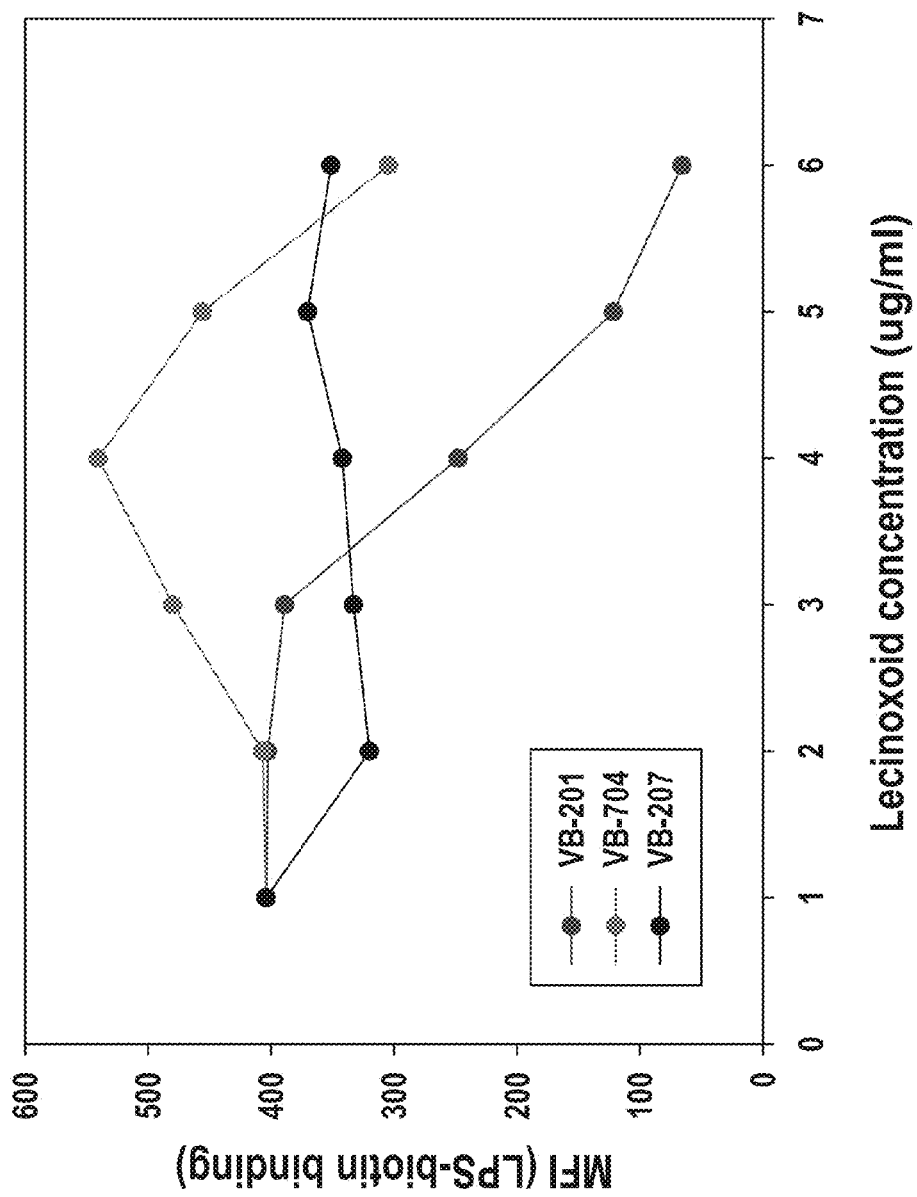
FIG. 16 shows VB-704 does not inhibit LPS-biotin binding to human monocytes (primary CD14+).

Human monocytes were obtained, treated and analyzed by LPS binding inhibition assay as described in Example 17 and FIG. 16. FIG. 16 shows that VB-704 does not inhibit LPS-biotin binding to human monocytes (primary CD14+).

Example 21

VB-704 Inhibits Chemokine-Induced Migration in Human Monocytes (Primary CD14+)

Figure 17:
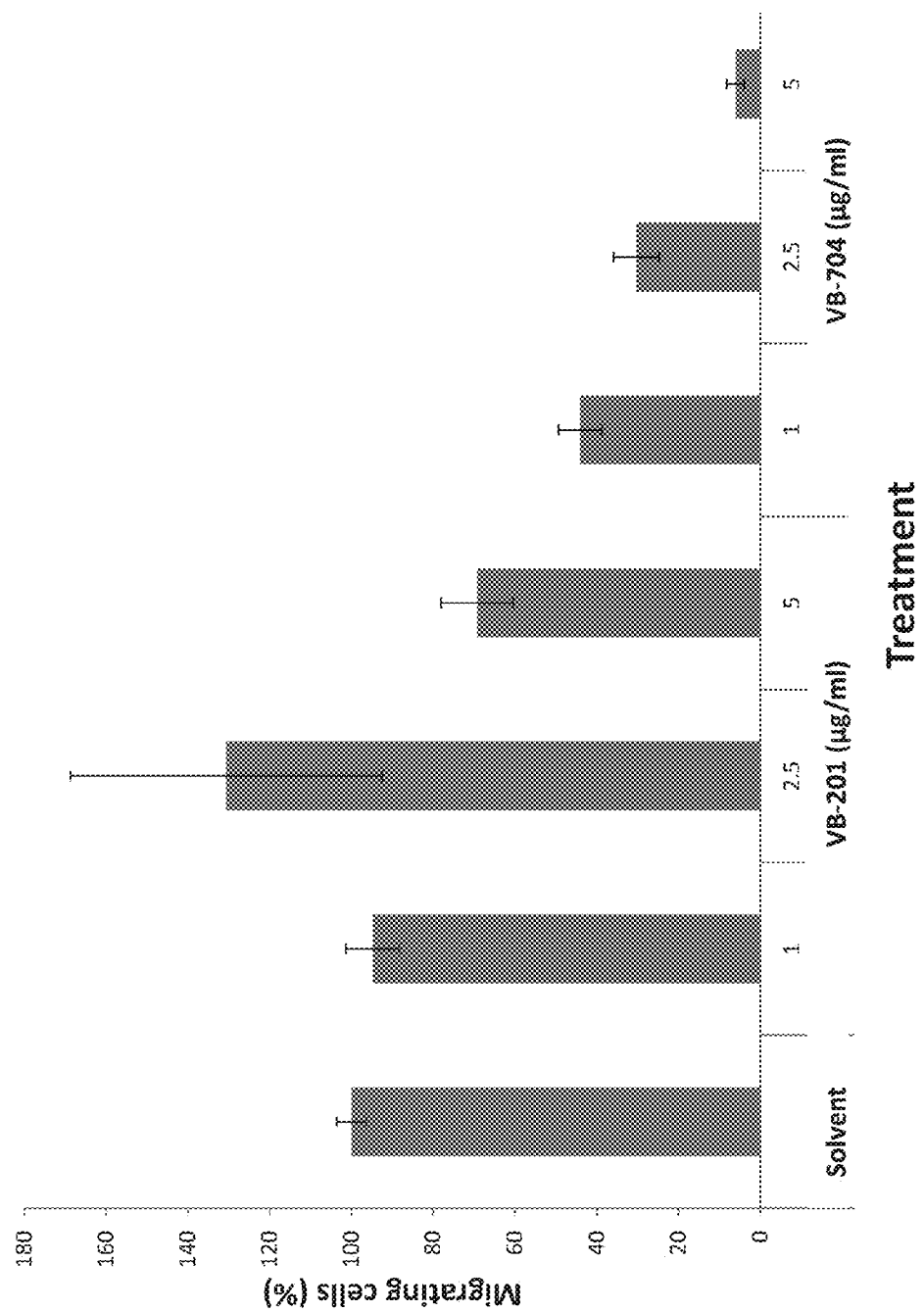
FIG. 17 shows VB-704 inhibits chemokine-induced cell migration of human monocytes (primary CD14+).

Human monocytes were obtained, treated and analyzed for cell migration by trans-well assay as described in Example 12 and FIG. 17. FIG. 17 shows that VB-704 inhibits chemokine-induced migration in human monocytes (primary CD14+).

Example 22

VB-705 Inhibits TLR4 Mediated Signaling in Human Monocytes (Primary CD14+)

Figure 18:
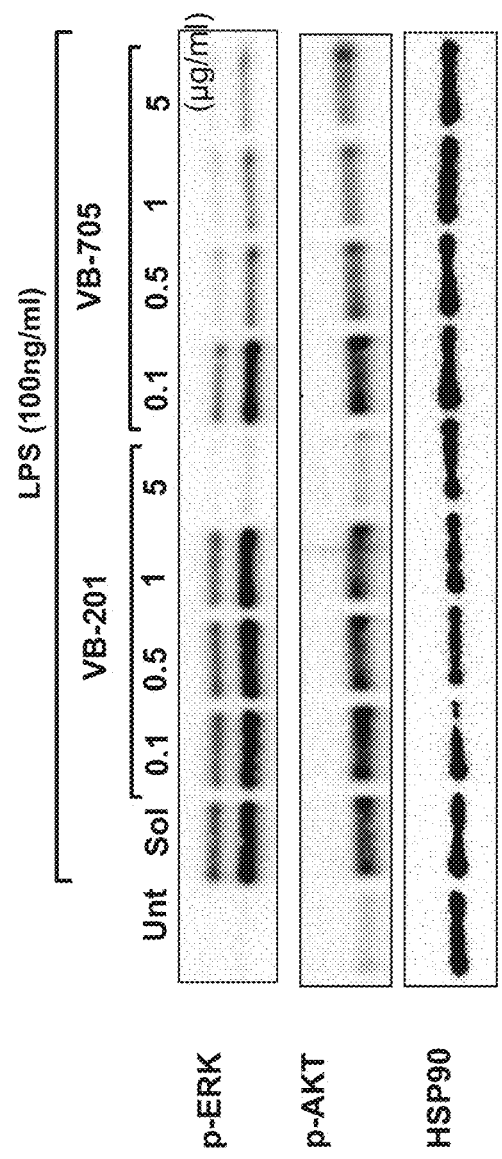
FIG. 18 shows VB-705 and VB-201 inhibit TLR4-induced signaling in human monocytes (primary CD14+).

Human monocytes were obtained, treated and analyzed by western blot as described in Example 9 and FIG. 18. FIG. 18 shows that VB-705 and VB-201 inhibit formation of p-ERK and p-AKT induced by LPS in human monocytes. Accordingly, VB-705 and VB-201 inhibit LPS (TLR4)-induced signaling in human monocytes (primary CD14+).

Example 23

VB-705 Inhibits LPS Binding in Human Monocytes (Primary CD14+)

Human monocytes were obtained, treated and analyzed With an LPS binding inhibition assay as described in Example 17 and FIG. 19. FIG. 19 shows that VB-705 inhibits LPS-biotin binding to human monocytes (primary CD14+).

Example 24

VB-705 does not Inhibit SDF1-Induced Migration of Human Monocyte (THP-1 Cells)

Methods and Materials
THP-1 cells ($10^6$/ml) were pretreated for 20 min with VB-201 or VB-705 at 5 μg/ml, or with solvent (Sol). To test for chemokine-induced cell migration, RANTES (100 ng/ml, Cat. No. 300-06) (PeproTech, Israel) and MCP-1 (50 ng/ml, Cat. No. 300-04) (PeproTech, Israel) were dissolved in RPMI-1640 medium supplemented with 0.5% fetal bovine serum (FBS) and placed at the lower chamber of QCM 24-well, 5 mm pore, migration assay plates (Corning-Costar, Corning, N.Y.). Cells ($3 \times 10^5$) were seeded in the upper chamber and incubated for 2-4 hours. Subsequently, the number of cells which migrated to the lower compartment was determined by fluorescence-activated cell sorting (FACS).
Results
FIG. 20 shows VB-705 does not inhibit SDF1-induced migration of human monocytes (THP-1 cell line).

Example 25

VB-703 and Focal and Segmental Glomerulosclerosis

Methods and Materials
Animals and Experimental Protocol
Male Sprague Dawley (SD) Rats (Harlan Laboratories, Israel with an initial weight of 200 g were housed 2-3 per cage in IVC cages in dedicated HVAC (heat, ventilation, air conditioning animal facility at a temperature of 22±2° C. and RH (relative humidity) of 55±15%). Temperature and humidity were monitored continuously. The facility had no exposure to outside light and was maintained on automatic alternating cycles of 12 hours of light and 12 hours of dark. Animals were provided with a commercial rodent diet (Harlan Teklad TRM Rat/Mouse Diet) ad libitum and allowed free access to autoclaved water, supplied to each cage via polysulphone bottles with stainless steel sipper tubes. All animal work was approved by the Animal Care and Use Committee of Israel (IL-13-03-027).
Induction of Chronic Renal Disease by 5/6 Nephrectomy
Rats were divided into three groups: (1) Healthy rats (n=3) in group A, (2) Sham group—subjected to chirurgical process but without kidney mass reduction (n=3) in group B, and (3) the rest were induced with chronic renal failure (n=32). Chronic renal failure was induced by a two stage (5/6) nephrectomy (Nx), with subtraction firstly of about ⅔ of the left kidney by left flank incision and, one week later, complete removal of the right kidney. General anesthesia consisted of intraperitoneal injection of ketamine 100 mg/kg and xylazine 20 mg/kg (0.85 ml ketamine+0.15 ml xylazine for each ml preparation; 1 μl/g BW was injected I.P).
Experimental Groups
One week following the second surgery, rats were randomly assigned to the following experimental groups:
Healthy, orally administered with vehicle—PBS 0.5% Ethanol (n=3);
Sham-operated, orally administered with vehicle—PBS 0.5% Ethanol (n=3);
Nephrectomized, orally administered with vehicle—PBS 0.5% Ethanol (n=8); Nephrectomized, orally administered with VB-703 4 mg/kg (n=8); and Nephrectomized, orally administered with telmisartan 10 mg/kg as positive control (n=8).
Body weight (BW) was monitored throughout the study and its were treated by oral gavage according to their body weight for 7 weeks. Rats were sacrificed by $CO_2$ inhalation 8 weeks from removal of the right kidney ($2^{nd}$ surgery).
Blood Analysis, Albuminuria, and Creatinine Clearance
Proteinuria and albuminuria was determined in urine specimens, collected during a 24-hour period, from animals housed in cages at 4 weeks (3w of treatment) and 8 weeks (7w of treatment) after the subtotal nephrectomy ($2^{nd}$ surgery). Urine samples were analyzed for: glucose, urea, sodium, potassium, creatinine, total protein, and albumin.
Serum was collected at 8 weeks after the subtotal nephrectomy ($2^{nd}$ surgery). The serum collected was also analyzed for glucose, urea, sodium, potassium, creatinine, total protein, albumin, and globulin.

Kidney Collection

Upon sacrifice, at 8 weeks, kidneys were collected, weighed and fixed in 4% formaldehyde.

Renal Morphology and Morphometric Analysis

For light microscopy, paraffin-embedded tissue slides of 4 μm were stained with Periodic Acid-Schiff (PAS) reagent, Masson's Trichrome and Hemataxylin & Eosin.

Glomerular Sclerosis Index.

Glomerulosclerosis was assessed by PAS-stained sections using a semiquantitative scoring system. The extent of glomerulosclerosis was evaluated by examining mostly 100 randomly selected glomeruli at magnification of ×400 and applying a score system according to the percentage of sclerosed glomerular area. The score was graded from 0 to 4: (0=0% area; 1=1-25%; 2=26-50%, 3=51-75%, 4=76% and above). The mean of all scored glomeruli was presented. Moreover, the extent of global and segmental glomerulosclerosis was evaluated in the same glomeruli, where <80% sclerosis was referred to as segmental and >80% was referred to as global.

Glomerular Area.

The glomerular area of mostly 100 randomly selected glomeruli at a magnification of ×100 was quantitated by counting squares covered by glomeruli area using a grid and the mean glomeruli area was calculated.

Immunohistochemistry

Renal tissues were fixed in 4% formaldehyde and embedded in paraffin. The paraffin-embedded tissues were then cut to form tissue slides of 4 μm. Immunohistochemistry of the paraffin-embedded tissue slides was analyzed using antibodies in the following concentration: monoclonal mouse anti rat CD-68 (ED-1, Serotec MCA341) 1:25. For quantitation of interstitial CD68+ staining, the number of positive cells was counted in 20 randomly selected non-overlapping fields per animal, and the mean value was presented.

Real-Time PCR

Kidney RNA was extracted with an RNeasy Fibrous Tissue Mini kit (Qiagen) and after DNAse I treatment, single-stranded cDNA was synthesized from 2 μg total RNA using the qScript cDNA Synthesis Kit (Quanta Biosciences) and diluted for real-time PCR. The expression of collagen 4α, fibronectin and TGFβ was quantified using the 7300 Real Time PCR System (Applied Biosystems). The assay was performed according to manufacturer instructions using the primers (Assay ID) represented at the table below supplied by Applied Biosystems. Data were normalized to the reference gene TATA box Binding Protein (TBP) and presented as relative mRNA levels compared with Sham PBS 0.5% Eth treatment (Table 1).

TABLE 1

Gene Expression references

| Assay ID | Gene Symbol | Gene Name |
|---|---|---|
| Rn01482927_m1 | Col IVα1 | Collagen; type IV; alpha 1 |
| Rn00572010_m1 | TGFβ1 | Transforming growth factor; beta 1 |
| Rn00569575_m1 | Fn1 | Fibronectin 1 |
| Rn01455646_m1 | TBP | TATA box binding protein |

Statistics

Data are expressed as means±SEM. Statistical significance was determined by one-way ANOVA or Student's t-test where appropriate. Statistical analyses were performed using Sigma Stat software.

Results

VB-703 Treatment Effect on Physiological Parameters

Figure 22:
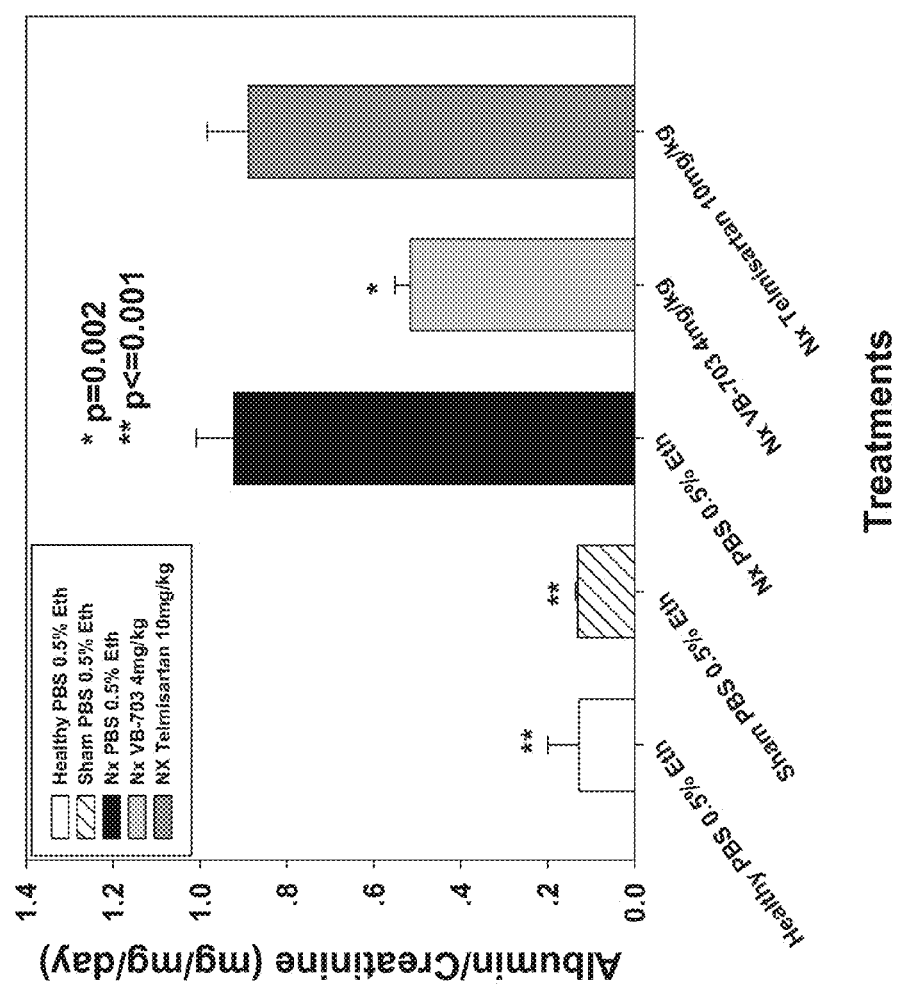
FIG. 22 presents bar graphs showing the effect of VB-703 on albumin/creatinine (mg/mg/day). Albumin/Creatinine/Day in healthy rats (n=3) (white bar), sham operated rats (n=3) (white bar with stripes), nephrectomized rats treated with solvent control (0.5% ethanol/PBS) (black bar) (n=7), nephrectomized rats VB-703 4 mg/kg treated (n=7) (light gray bar) or nephrectomized rats telmisartan 10 mg/kg treated (n=8) (dark gray bar) were evaluated at 8 weeks. Statistical data vs. nephrectomized rats treated with solvent control (0.5% ethanol/PBS) is presented as follows: * represents p=0.002; and ** represents p≤0.001. Abbreviations are: Nx, nephrectomized; Eth, ethanol.

VB-703 treatment significantly improved urinary albumin/creatinine/day ratio at the termination of the study (FIG. 22).

VB-703 Treatment Effect on Glomerular Damage

Glomeruli were evaluated for their fibrosis extent by scoring and by calculation of the percent of glomeruli having segmental sclerosis, global sclerosis and the sum of global and segmental sclerotic glomeruli. Moreover, the area of the glomeruli Was calculated and the percent of hypertrophied glomeruli was calculated. Damaged glomeruli included hypertrophied (at least ×1.5 from normal area) and or sclerotic glomeruli.

Figure 23:
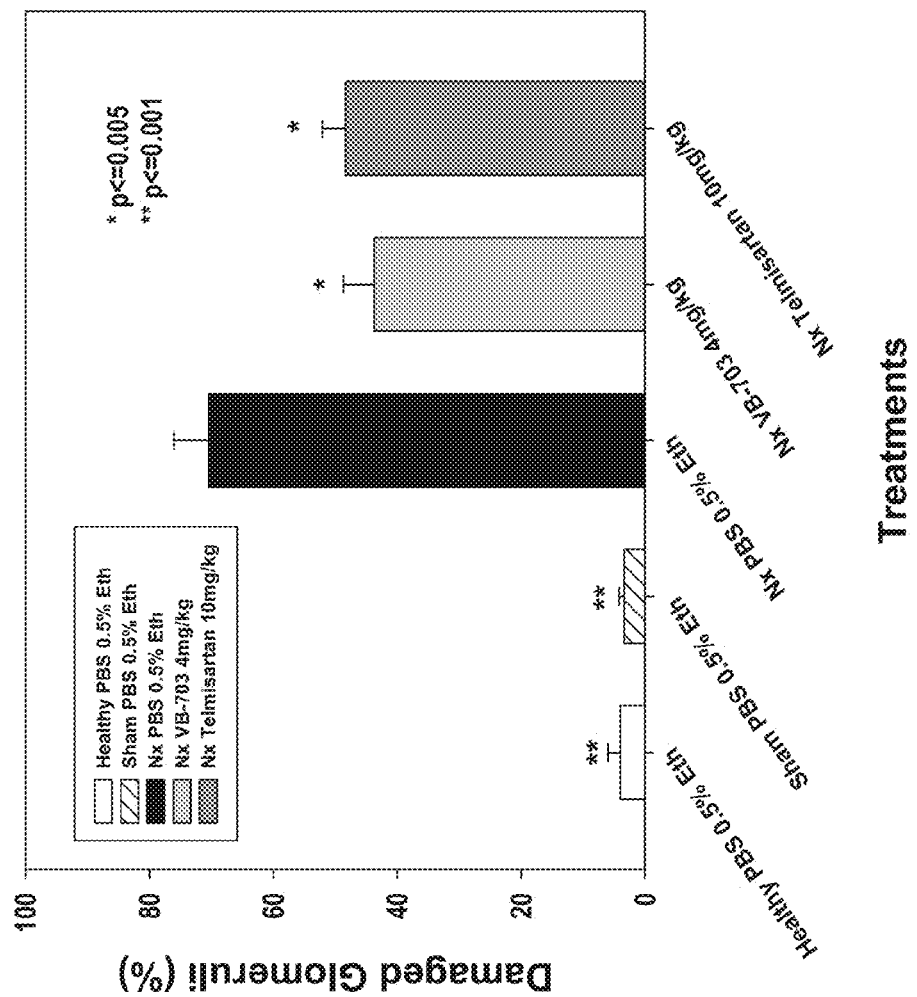
FIG. 23 presents bar graphs showing the effect of VB-703 in reducing the number of damaged glomeruli (%). Damaged glomeruli (%) in healthy rats (n=3) (white bar), sham operated rats (n=3) (white bar with stripes), nephrectomized rats treated with solvent control (0.5% ethanol/PBS) (black bar) (n=7), nephrectomized rats VB-703 4 mg/kg treated (n=7) (light gray bar) or nephrectomized rats telmisartan 10 mg/kg treated (n=8) (dark gray bar) were evaluated at 8 weeks. Statistical data vs. nephrectomized rats treated with solvent control (0.5% ethanol/PBS) is presented as follows: * represents p≤0.005; and ** represents p≤0.001. Abbreviations are: Nx, nephrectomized; Eth, ethanol.
Figure 24:
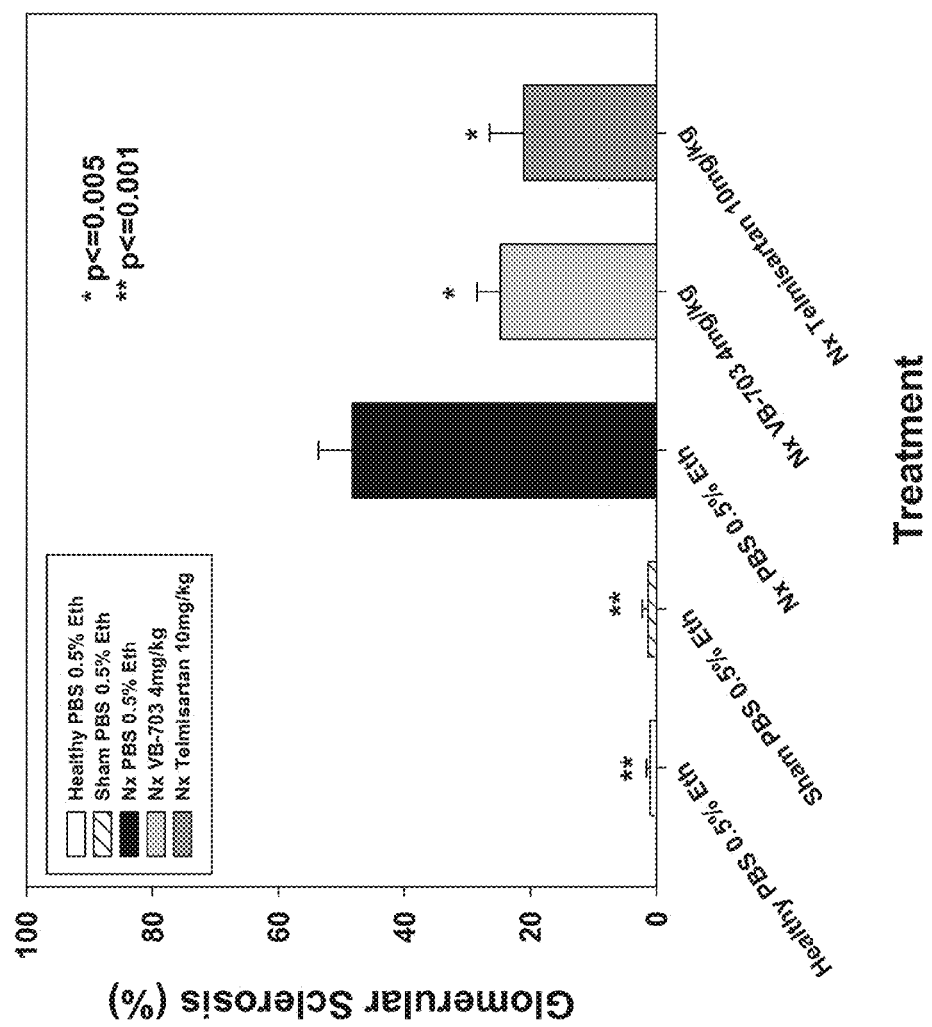
FIG. 24 presents bar graphs showing the effect of VB-703 in reducing glomerular sclerosis (%). Glomerular sclerosis (%) in healthy rats (n=3) (white bar), sham operated rats (n=3) (white bar with stripes), nephrectomized rats treated with solvent control (0.5% ethanol/PBS) (black bar) (n=7), nephrectomized rats VB-703 4 mg/kg treated (n=7) (light gray bar) or nephrectomized rats telmisartan 10 mg/kg treated (n=8) (dark gray bar) were evaluated at 8 weeks. Statistical data vs. nephrectomized rats treated with solvent control (0.5% ethanol/PBS) is presented as follows: * represents p≤0.005; and ** represents p≤0.001. Abbreviations are: Nx, nephrectomized; Eth, ethanol.

VB-703 and telmisartan treatment significantly reduced the damaged glomeruli percent by 38% (p≤0.005) and 31% (p≤0.005) respectively (FIG. 23). This effect was partially contributed by the reduction in glomeruli hypertrophy. The major contribution to the reduction in glomeruli damage was due to the reduction in sclerotic glomeruli. VB-703 and telmisartan treatment resulted in a 49% (p≤0.005) and 57% (p≤0.005) reduction of sclerotic glomeruli, respectively (FIG. 24, Table 2).

TABLE 2

Effect of VB-201 on Glomerular sclerosis (Mean ± S.E)*

| | Treatment | | | | |
|---|---|---|---|---|---|
| Glomerular sclerosis | Healthy PBS 0.5% Eth | Sham PBS 0.5% Eth | Nx PBS 0.5% Eth | Nx VB-703 4 mg/kg | Nx Telmisartan 10 mg/kg |
| Segmental % | 1.0 ± 0.58 (n = 3) p ≤ 0.001 | 1.3 ± 0.88 (n = 3) p ≤ 0.001 | 41.0 ± 4.81 (n = 7) | 22.9 ± 2.83 (n = 7) P < 0.01 | 19.1 ± 4.30 (n = 8) P = 0.005 |
| Global % | 0.0 ± 0.00 (n = 3) n.s | 0.0 ± 0.00 (n = 3) n.s | 7.1 ± 4.39 (n = 7) | 1.9 ± 1.55 (n = 7) n.s | 1.9 ± 1.60 (n = 8) n.s |
| Global & Segmental % | 1.0 ± 0.58 (n = 3) p ≤ 0.001 | 1.3 ± 0.88 (n = 3) p ≤ 0.001 | 48.3 ± 5.38 (n = 7) | 24.7 ± 3.77 (n = 7) P < 0.005 | 21.0 ± 5.45 (n = 8) P < 0.005 |

*Number of animals tested per group and p value versus Nx PBS 0.5% Eth group is presented.

Figure 25:
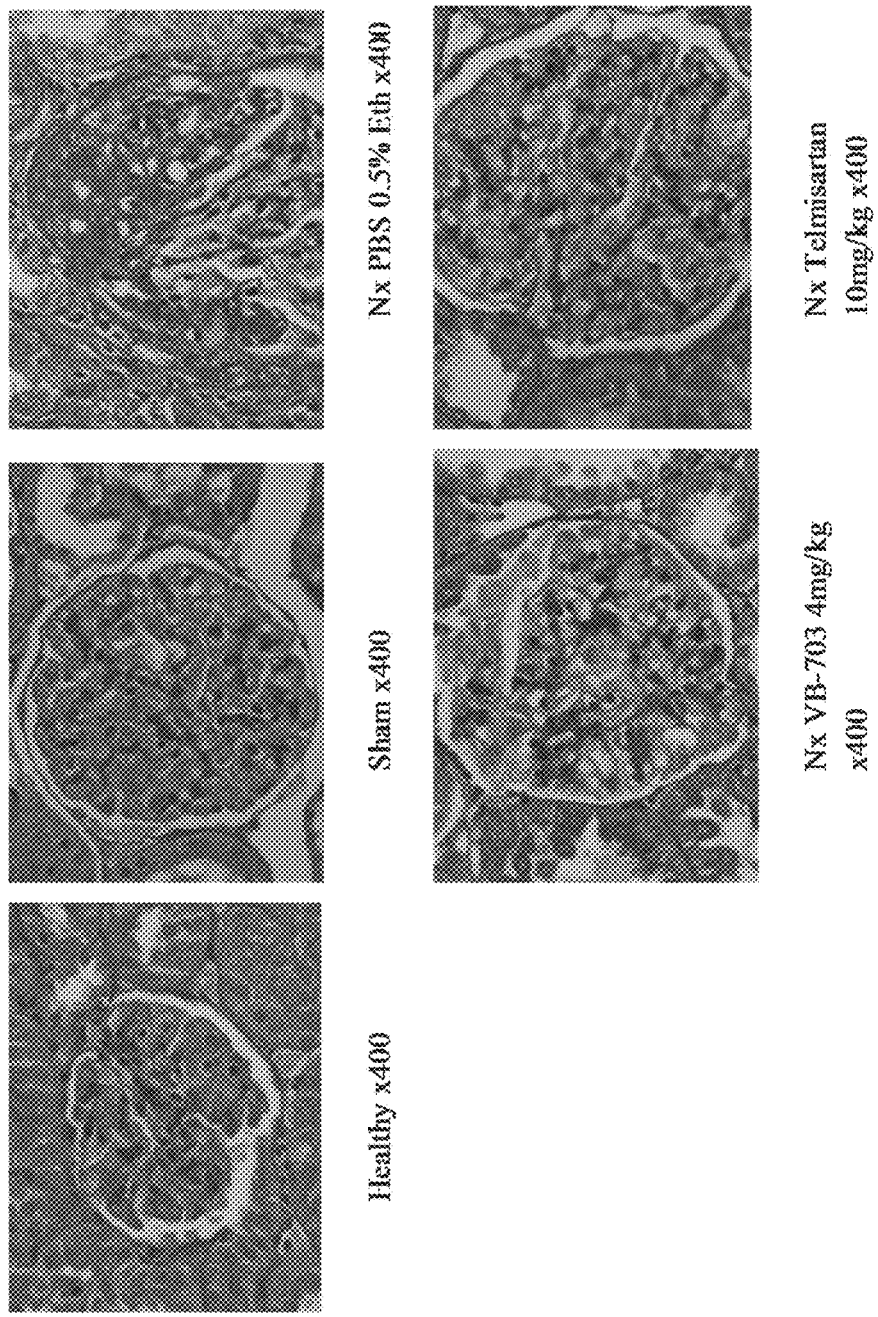
FIG. 25 presents PAS staining images (×400) showing the effect of VB-703 in reducing glomerular sclerosis. Renal morphology was assessed by light microscope in PAS stained sections of healthy rats (Healthy×400), sham operated rats (Sham×400), nephrectomized rats treated with solvent control (0.5% ethanol/PBS) (Nx PBS 0.5% Eth× 400), nephrectomized rats VB-703 4 mg/kg treated (Nx VB-703 4 mg/kg×400) or nephrectomized rats telmisartan 10 mg/kg treated (Nx Telmisartan 10 mg/kg×400) at 8 weeks following the first surgery. Abbreviations are: Nx, nephrectomized; Eth, ethanol, PAS, Periodic Acid-Schiff.

FIG. 25 shows typical sclerotic changes in glomeruli (PAS staining) of vehicle treated nephrectomized animals in contrast with healthy or sham operated animals or with VB-703 treated animals, or telmisartan treated animal.

VB-703 Treatment Effect on Pro-Fibrotic Markers

The mRNA expression of Collagen IV was increased by 7 of 8 fold respectively in vehicle treated nephrectomized rats (7.5±1.51) in contrast with healthy (1.1±0.12) or sham operated animals (1.0±0.32). VB-703 treatment significantly (p<0.05) reduced Collagen IV expression by 51% (3.7±0.52) compared to those observed for Nx PBS 0.5% Eth treatment. A 41% reduction in Collagen IV expression was observed in the telmisartan treated nephrectomized rats (4.4±0.23) compared to those observed for Nx PBS 0.5% Eth treatment, with marginal significance (p=0.064) (FIG. 26A).

The mRNA expression of fibronectin was increased by 16 or 13 fold respectively in vehicle treated nephrectomized rats (12.7±1.01) in contrast with healthy (0.8±0.08) or sham operated animals (1.0±0.31). VB-703 treatment significantly (p<0.005) reduced fibronectin expression by 47% (6.7±0.98) compared to those observed for Nx PBS 0.5% Eth treatment. Telmisartan treatment moderately reduced fibronectin expression by 23% (9.8±2.09); however this reduction was not statistically significant (FIG. 26B).

The mRNA expression of TGF-β was increased by 10 or 8 fold respectively in vehicle treated nephrectomized rats (8.4±0.49) in contrast with healthy (0.9±0.24) or sham operated animals (1.0±0.23) (p≤0.001). VB-703 and telmisartan treatment significantly (p≤0.001) reduced TGF-β expression by 42% (4.8±0.32), and by 44% (4.7±0.52), respectively, compared to those observed for Nx PBS 0.5% Eth treatment (FIG. 26C).

Figure 27A:
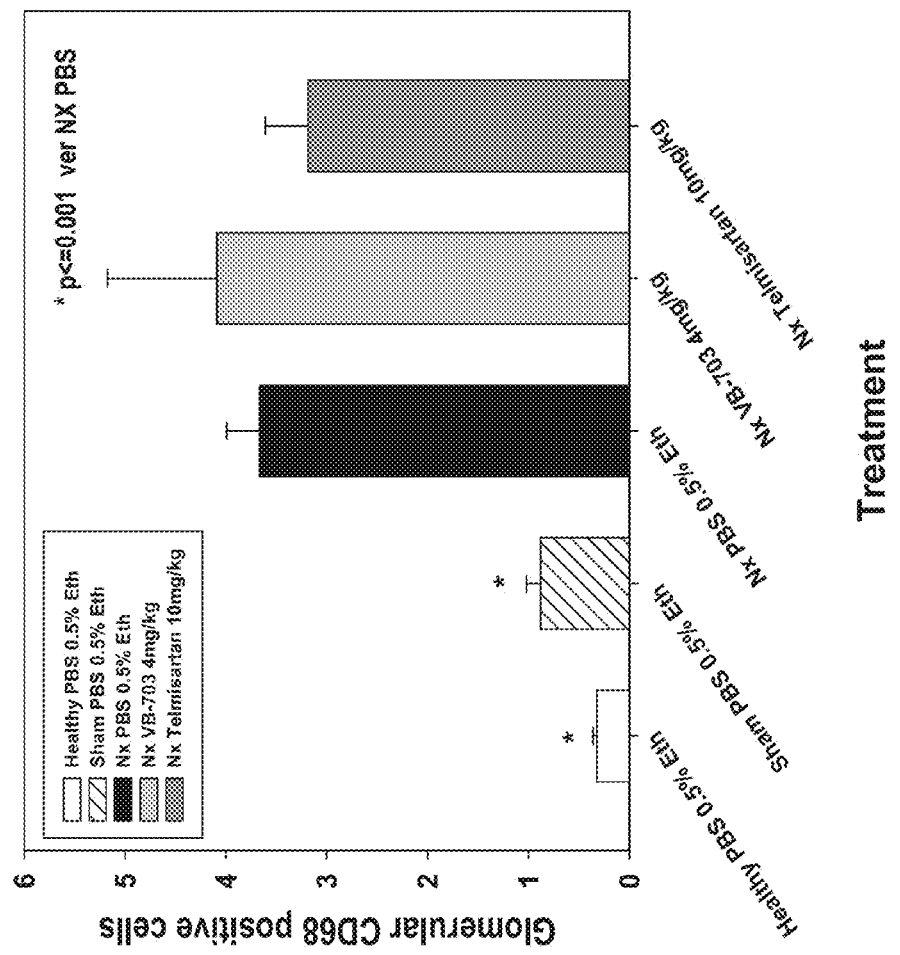
FIGS. 27A-27B show the output of an experiment evaluating the effect of VB-703 on monocyte/macrophage cell infiltration in the glomeruli (FIG. 27A) or in the interstitium (FIG. 27B). CD68 positive cells in the glomeruli (cells/glomeruli) and in the interstitium (cells/mm$^2$) were evaluated in healthy rats (n=3) (white bar), sham operated rats (n=3) (white bar with stripes), nephrectomized rats treated with solvent control (0.5% ethanol/PBS) (black bar) (n=7), nephrectomized rats VB-703 4 mg/kg treated (n=7) (light gray bar), or nephrectomized rats telmisartan 10 mg/kg treated (n=8) (dark gray bar) at 8 weeks. Abbreviations are: Nx, nephrectomized; Eth, ethanol.
Figure 27B:
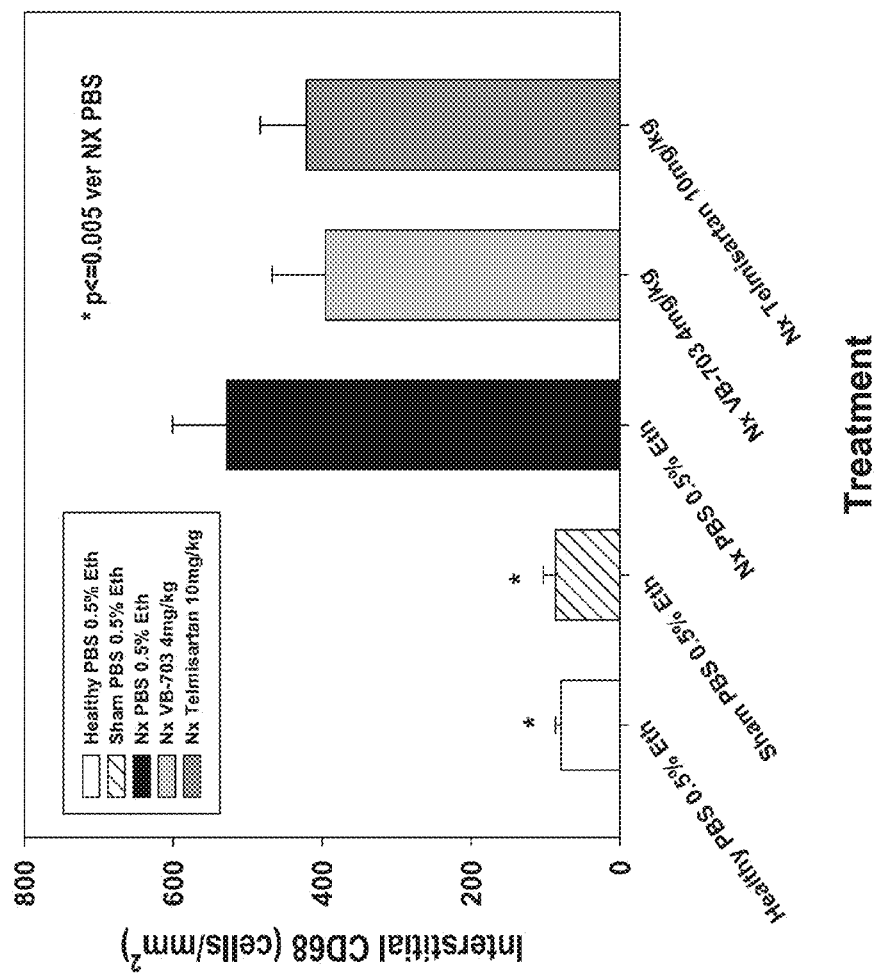

VB-703 Treatment Effect on Glomerular and Interstitial Monocyte/Macrophage Infiltration FIGS. 27A-27B show the effect of VB-703 on monocyte/macrophage cell infiltration in the glomeruli (FIG. 27A) or in the interstitium (FIG. 27B). In this experiment, VB-703 and telmisartan did not produce a significant effect on reducing glomerular and interstitial monocyte/macrophage infiltration.

All publications, patents and patent applications mentioned in this application are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having a structure according to Formula 1,

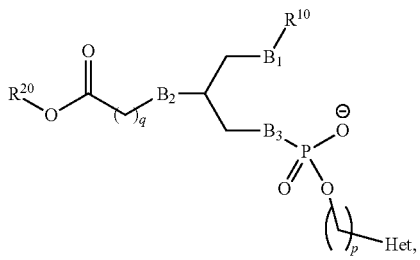

Formula 1 or a stereoisomer, a stereoisomeric mixture, or a salt thereof;
wherein each of $B_1$, $B_2$, and $B_3$ is independently selected from the group consisting of oxygen, sulfur, nitrogen, phosphorus, and silicon; wherein each of said nitrogen, phosphorus and silicon is optionally substituted by one or more substituents selected from the group consisting of alkyl, halo, cycloalkyl, aryl, hydroxy, thiohydroxy, alkoxy, aryloxy, thioaryloxy, thioalkoxy, and oxo;
wherein $R^{10}$ is a $C_{2-28}$ alkyl optionally substituted by one to five $R^{11}$ substituents, wherein each $R^{11}$ is independently selected from the group consisting of alkyl, alkenyl, alkynyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy, and amino;
wherein p is an integer selected from 1-10;
wherein q is an integer selected from 1-26;
wherein $R^{20}$ is selected from the group consisting of hydrogen, alkyl, alkenyl, alkynyl, cycloalkyl, aryl, and heteroaryl;
wherein Het is an optionally substituted heteroalicyclic or a heteroaryl.

2. The compound of claim 1, having a structure according to Formula 2,

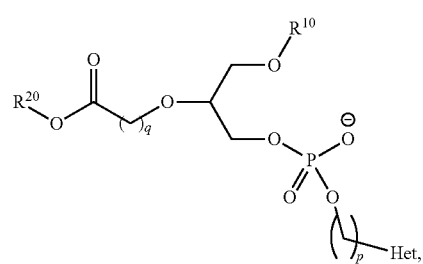

Formula 2 wherein Het is a pyridine and wherein the nitrogen atom of the pyridine is directly connected to the alkylene chain —(CH$_2$)$_p$—;
wherein the pyridine is unsubstituted or substituted by one to five $R^{12}$ substituents; and
wherein $R^{12}$ is a halogen, a $C_{6-10}$ aryl, a heteroaryl, or an alkyl.

3. The compound of claim 2, having a structure according to Formula 3,

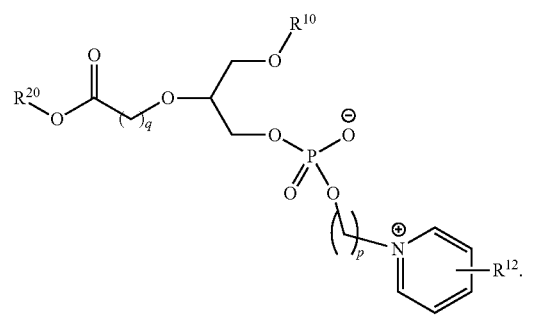

Formula 3

4. The compound of claim 3, wherein $R^{10}$ is selected from the group consisting of hexadecyl, eicosanyl, and (2'-octyl) dodecyl.

5. The compound of claim 3, wherein $R^{20}$ is a hydrogen or a $C_{1-4}$ alkyl.

6. The compound of claim 3, wherein q is an integer of 2-6.

7. The compound of claim 3, wherein p is an integer of 2-5.

8. The compound of claim 2, wherein the pyridine is substituted by one, two, or three $R^{12}$ substituents.

9. The compound of claim 8, wherein each $R^{12}$ is independently a halogen, an aryl, or a $C_{1-4}$ alkyl.

10. The compound of claim 9, wherein the pyridine is substituted by one $R^{12}$ substituent, wherein the one $R^{12}$ substituent is a fluorine or a phenyl.

11. The compound of claim 10, wherein the pyridine is 3-fluoro-pyridine or 3-phenyl-pyridine.

12. The compound of claim 2, having a structure according to Formula 4,

Formula 4

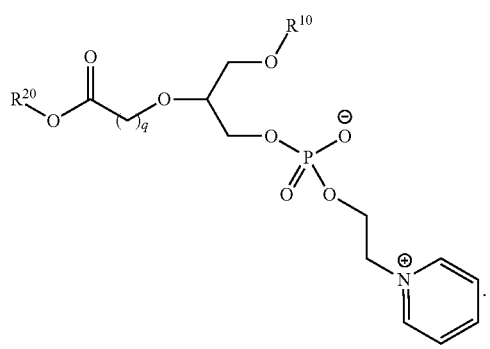

13. The compound of claim 12, wherein $R^{10}$ is selected from the group consisting of hexadecyl, dodecyl, octadecyl, octyl, eicosanyl, cis-9-hexadecenyl, (2'-octyl)dodecyl, and (15'-carboxy)pentadecyl.

14. The compound of claim 12, wherein $R^{20}$ is a hydrogen or an alkyl.

15. The compound of claim 12, having a structure according to Formula 5,

Formula 5

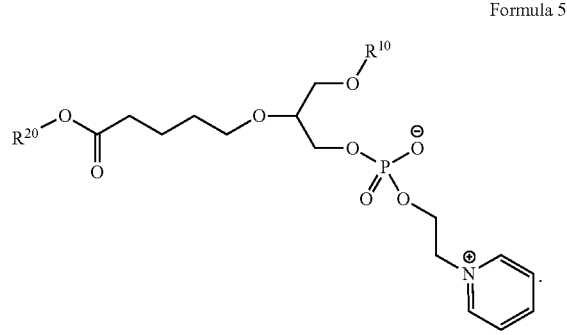

16. The compound of claim 15, wherein $R^{10}$ is selected from the group consisting of hexadecyl, eicosanyl, and (2'-octyl)dodecyl.

17. The compound of claim 15, wherein $R^{20}$ is a hydrogen or a $C_{1-4}$ alkyl.

18. The compound of claim 1, having a structure selected from the group consisting of:

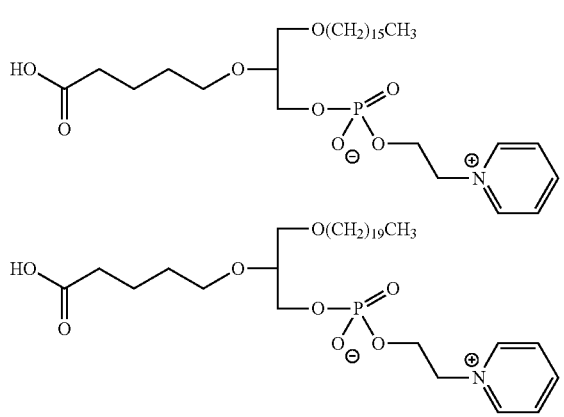

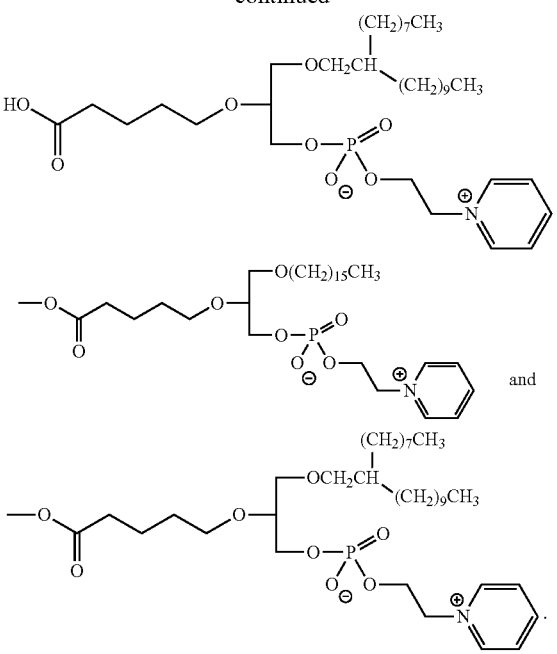

19. The compound of claim 18, selected from the group consisting of (R)-1-hexadecyl-2-(4'-carboxy)butyl-sn-glycero-3-phosphoric acid pyridiniumethyl ester (VB-701); (R)-1-eicosanyl-2-(4'-carboxy)butyl-sn-glycero-3-phosphoric acid pyridiniumethyl ester (VB-702); (R)-1-(2'-octyl)dodecyl-2-(4'-carboxy)butyl-sn-glycero-3-phosphoric acid pyridiniumethyl ester (VB-703); (R)-1-hexadecyl-2-(4'-carboxymethyl)butyl-sn-glycero-3-phosphoric acid pyridiniumethyl ester (VB-704); and (R)-1-(2'-octyl)dodecyl-2-(4'-carboxymethyl)butyl-sn-glycero-3-phosphoric acid pyridiniumethyl ester (VB-705).

20. The compound of claim 18, which is (R)-1-(2'-octyl)dodecyl-2-(4'-carboxy)butyl-sn-glycero-3-phosphoric acid pyridiniumethyl ester (VB-703).

21. The compound of claim 1, selected from the group consisting of

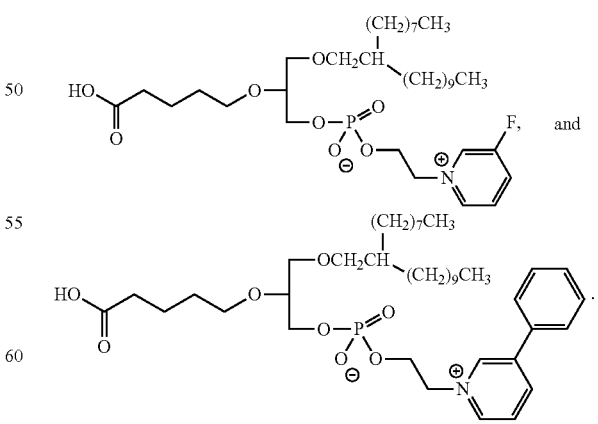

22. The compound of claim 21, selected from the group consisting of (R)-1-(2'-octyl)dodecyl-2-(4'-carboxy)butyl-glycero-sn-3-phosphoric acid 3-fluoro-pyridiniumethyl ester (VB-706) and (R)-1-(2'-octyl)dodecyl-2-(4'-carboxy)butyl-glycero-sn-3-phosphoric acid 3-phenyl-pyridiniumethyl ester (VB-707).

23. The compound of claim 1, in the form of a stereoisomer, a stereoisomeric mixture, or a salt.

24. A pharmaceutical composition comprising the compound of claim 1 and a pharmaceutically acceptable vehicle.

25. The compound of claim 18, having the structure of:

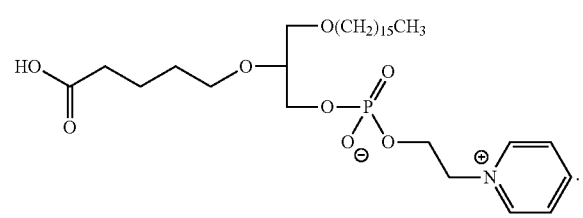

26. The compound of claim 18, having the structure of:

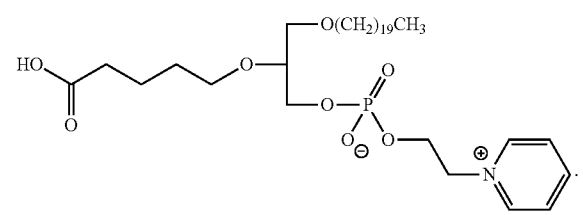

27. The compound of claim 18, having the structure of:

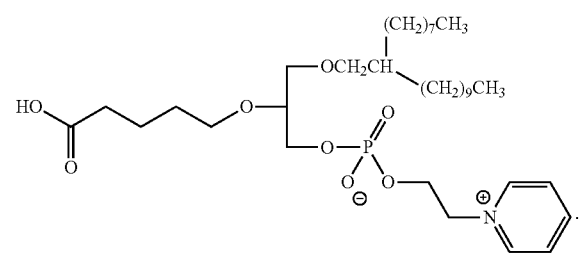

28. The compound of claim 18, having the structure of:

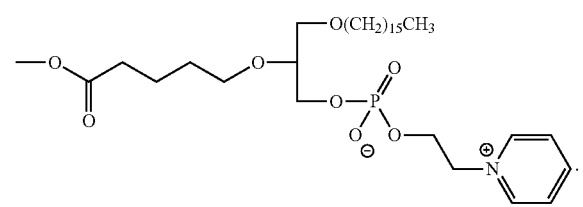

29. The compound of claim 18, having the structure of:

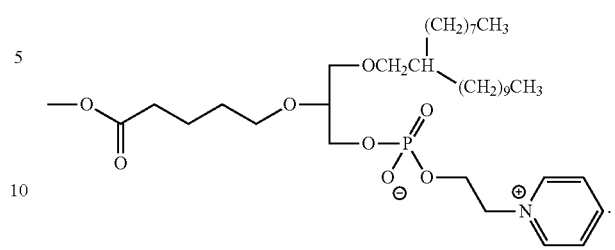

30. The compound of claim 21, having the structure of:

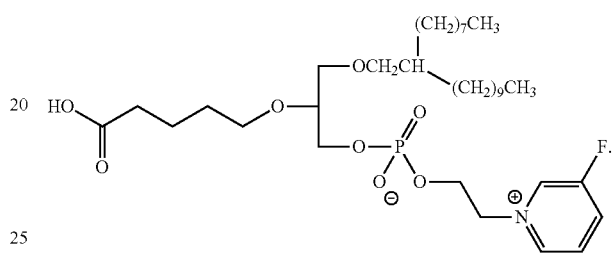

31. The compound of claim 21, having the structure of:

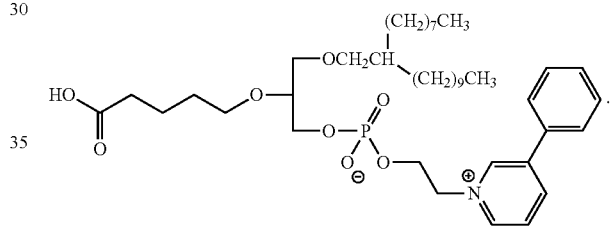

32. The compound of claim 19, which is (R)-1-hexadecyl-2-(4'-carboxy)butyl-sn-glycero-3-phosphoric acid pyridiniumethyl ester (VB-701).

33. The compound of claim 19, which is (R)-1-eicosanyl-2-(4'-carboxy)butyl-sn-glycero-3-phosphoric acid pyridiniumethyl ester (VB-702).

34. The compound of claim 19, which is (R)-1-hexadecyl-2-(4'-carboxymethyl)butyl-sn-glycero-3-phosphoric acid pyridiniumethyl ester (VB-704).

35. The compound of claim 19, which is (R)-1-(2'-octyl)dodecyl-2-(4'-carboxymethyl)butyl-sn-glycero-3-phosphoric acid pyridiniumethyl ester (VB-705).

36. The compound of claim 22, which is (R)-1-(2'-octyl)dodecyl-2-(4'-carboxy)butyl-glycero-sn-3-phosphoric acid 3-fluoro-pyridiniumethyl ester (VB-706).

37. The compound of claim 22, which is (R)-1-(2'-octyl)dodecyl-2-(4'-carboxy)butyl-glycero-sn-3-phosphoric acid 3-phenyl-pyridiniumethyl ester (VB-707).

* * * * *

UNITED STATES PATENT AND TRADEMARK OFFICE
CERTIFICATE OF CORRECTION

PATENT NO. : 9,771,385 B2
APPLICATION NO. : 14/952827
DATED : September 26, 2017
INVENTOR(S) : Ishai et al.

Page 1 of 1

It is certified that error appears in the above-identified patent and that said Letters Patent is hereby corrected as shown below:

Claim 1, Column 62, Lines 4-5, please replace "wherein Het is an optionally substituted heteroalicyclic or a heteroaryl" with -- wherein Het is an optionally substituted heteroalicyclic or an optionally substituted heteroaryl --.

Signed and Sealed this
Fifth Day of December, 2017

Joseph Matal
*Performing the Functions and Duties of the
Under Secretary of Commerce for Intellectual Property and
Director of the United States Patent and Trademark Office*